United States Patent
Ishihara et al.

(10) Patent No.: US 8,169,470 B2
(45) Date of Patent: May 1, 2012

(54) OPTICAL IMAGING DEVICE HAVING ILLUMINATION LIGHT FILTER SECTION

(75) Inventors: Yasushige Ishihara, Hachioji (JP); Atsushi Okawa, Hachioji (JP); Daisuke Akiyama, Hino (JP); Katsuichi Imaizumi, Hachioji (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 1511 days.

(21) Appl. No.: 11/511,203

(22) Filed: Aug. 28, 2006

(65) Prior Publication Data

US 2007/0046778 A1  Mar. 1, 2007

(30) Foreign Application Priority Data

Aug. 31, 2005 (JP) .................. 2005-252517
Jun. 19, 2006 (JP) .................. 2006-169356

(51) Int. Cl.
*H04N 7/18* (2006.01)
(52) U.S. Cl. .......................... 348/70; 348/68
(58) Field of Classification Search .................. 356/317; 359/359; 348/61, 68, 70
See application file for complete search history.

(56) References Cited

U.S. PATENT DOCUMENTS

| | | | |
|---|---|---|---|
| 4,663,657 A | 5/1987 | Nagasaki et al. | |
| 4,821,117 A | 4/1989 | Sekiguchi | |
| 5,749,830 A | 5/1998 | Kaneko et al. | |
| 6,635,011 B1 * | 10/2003 | Ozawa et al. | 600/178 |
| 6,809,589 B2 * | 10/2004 | Manganaro | 330/260 |
| 7,050,224 B2 * | 5/2006 | Kawamata et al. | 359/359 |
| 7,062,311 B1 * | 6/2006 | Sendai et al. | 600/407 |
| 7,330,749 B1 * | 2/2008 | Bhunachet | 600/476 |
| 7,453,568 B2 * | 11/2008 | Kawamata et al. | 356/317 |
| 2002/0072678 A1 | 6/2002 | Komachi et al. | |
| 2003/0040668 A1 | 2/2003 | Kaneko et al. | |

FOREIGN PATENT DOCUMENTS

| | | |
|---|---|---|
| JP | 08-224208 | 9/1996 |
| JP | 07-155285 | 6/1999 |
| JP | 11-244220 | 9/1999 |
| JP | 2002-301009 | 10/2002 |
| JP | 2004-294109 | 10/2004 |
| JP | 2005-058618 | 3/2005 |
| WO | WO 2005/001450 A1 | 1/2005 |

OTHER PUBLICATIONS

Japanese Office Action dated Nov. 1, 2011 in counterpart Japanese Patent Application No. 2006-169356.

* cited by examiner

*Primary Examiner* — Allen Wong
(74) *Attorney, Agent, or Firm* — Scully, Scott, Murphy & Presser, P.C.

(57) ABSTRACT

An optical imaging device of the present invention comprises: a light source device; a light guide and illumination lens, provided in an insertion section that can be inserted into a body cavity, for constituting an illumination light path for guiding an illumination light from the light source device to a subject; an objective lens for receiving return lights from the subject; an image capturing section for acquiring a visible light band image from the return light; an excitation light cut filter and image capturing section for acquiring a fluorescent image from the return lights; and an illumination light filter, provided on the illumination light path, for decreasing light in a band overlapping with the band of light of which image is captured by the image capturing section from the illumination light incident on.

9 Claims, 48 Drawing Sheets

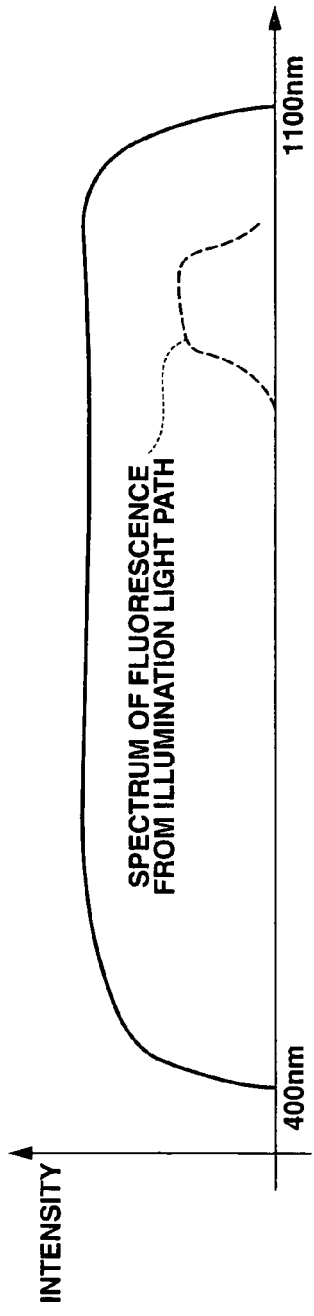
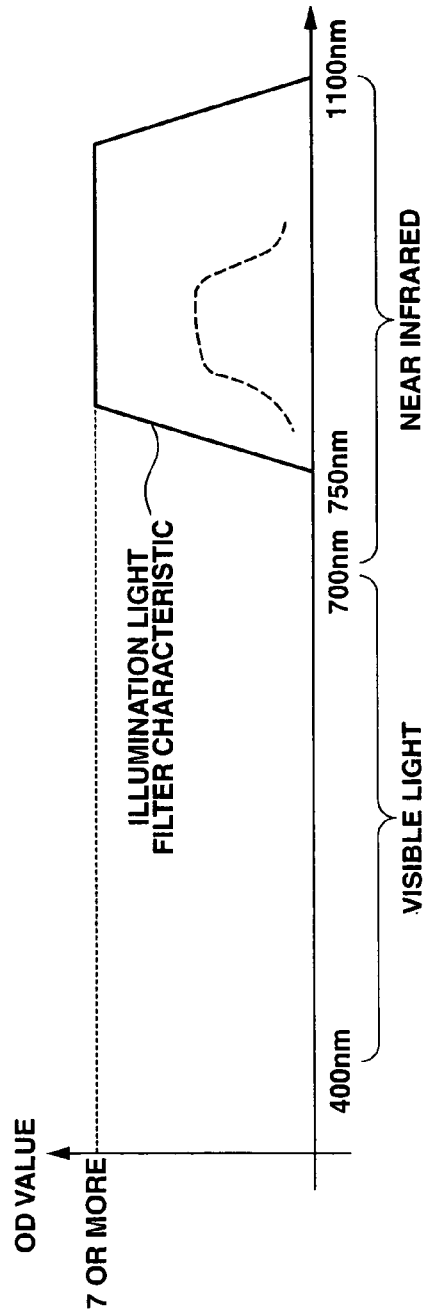

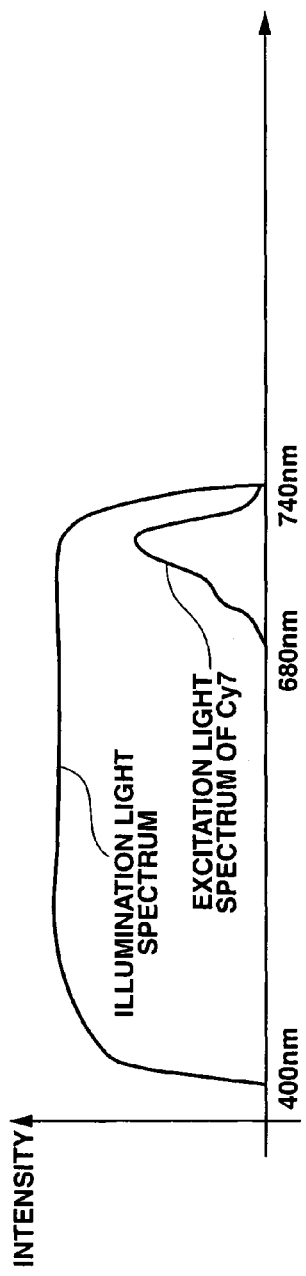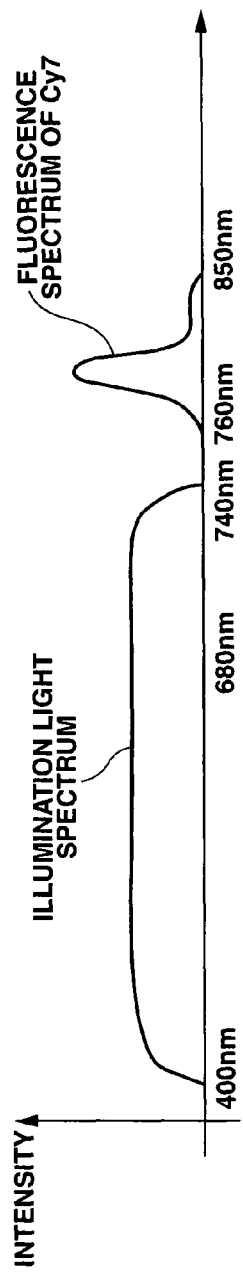

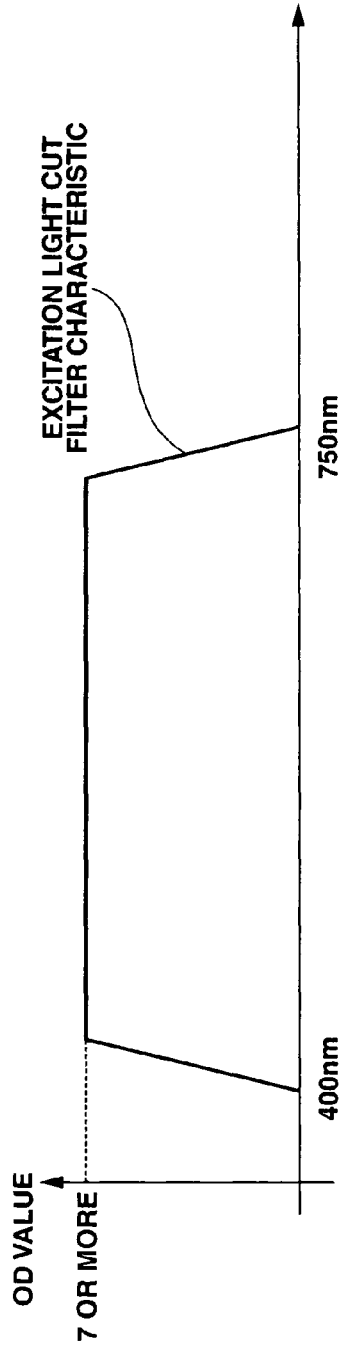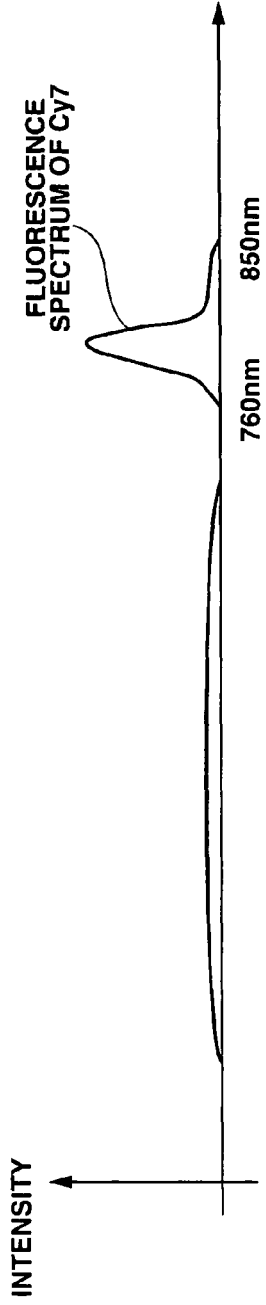

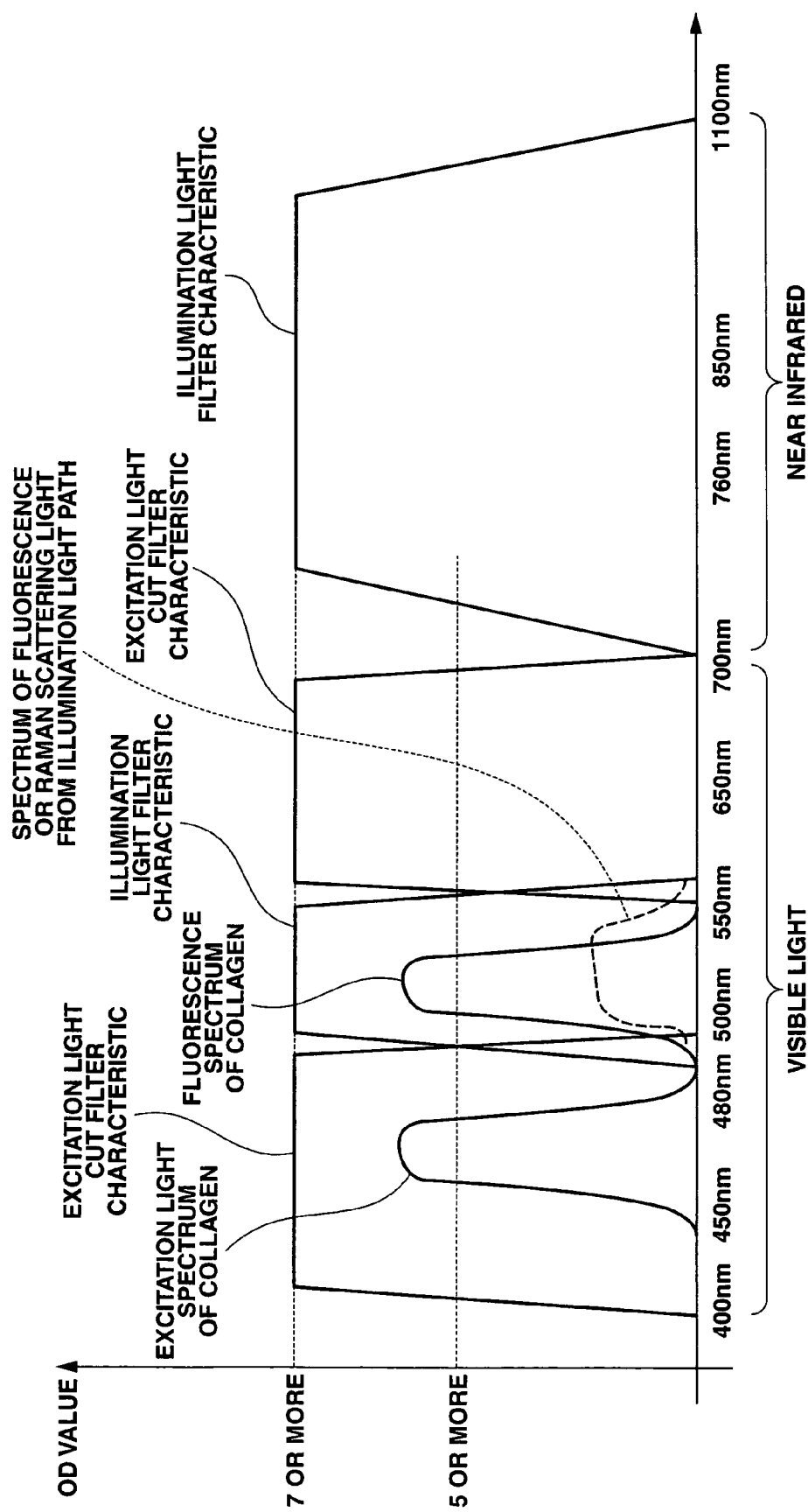

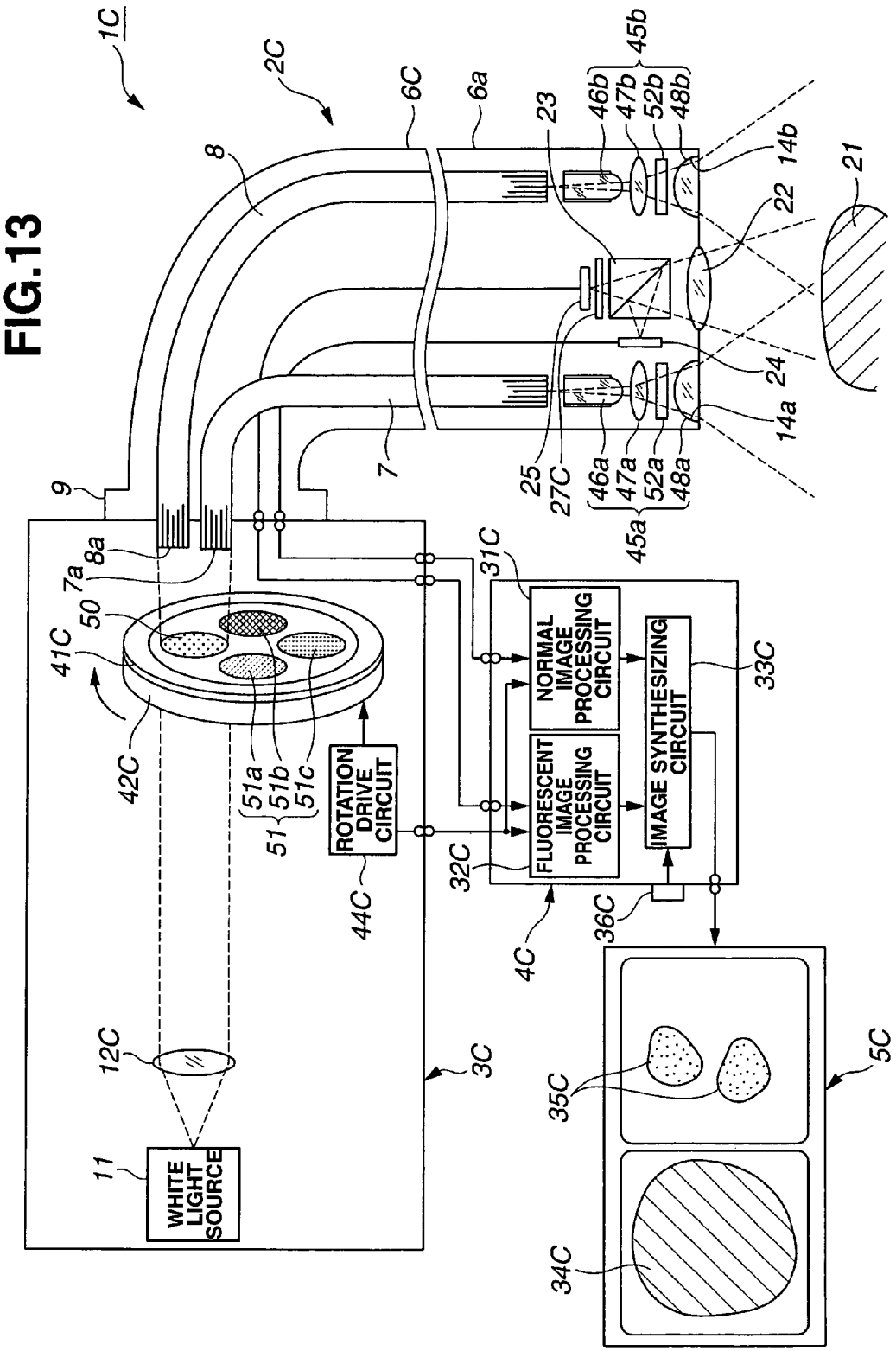

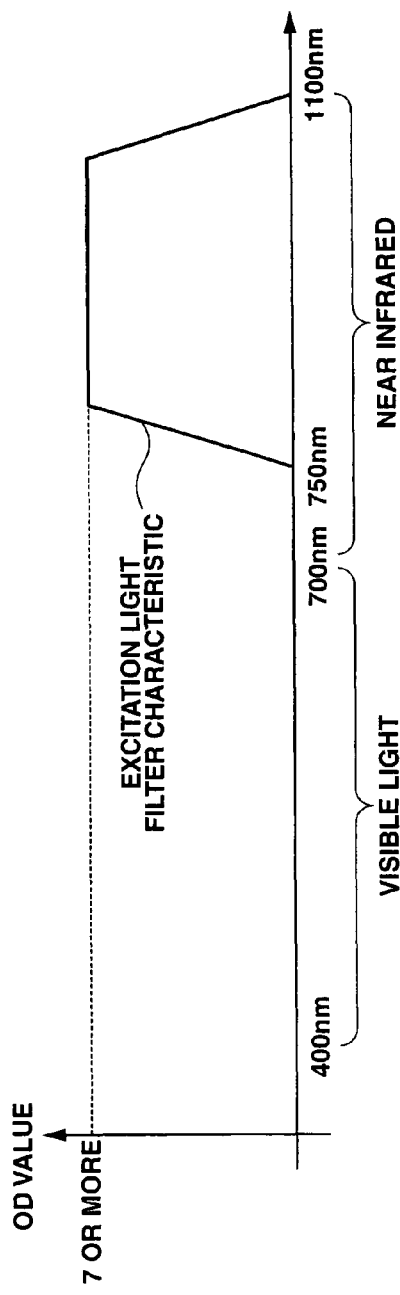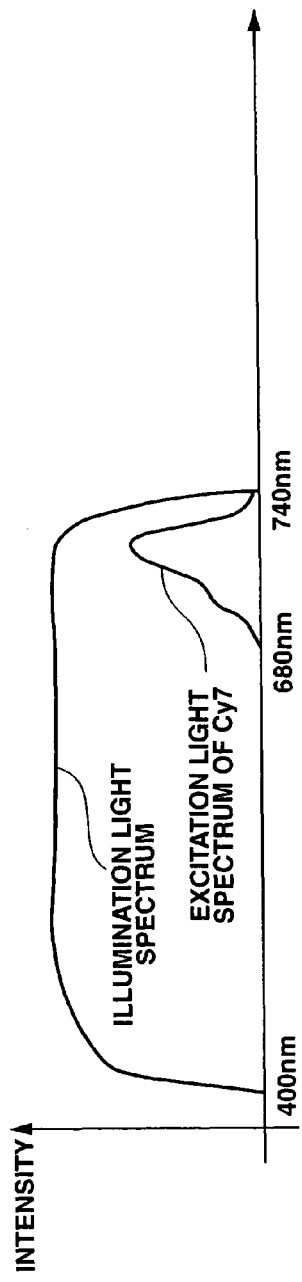

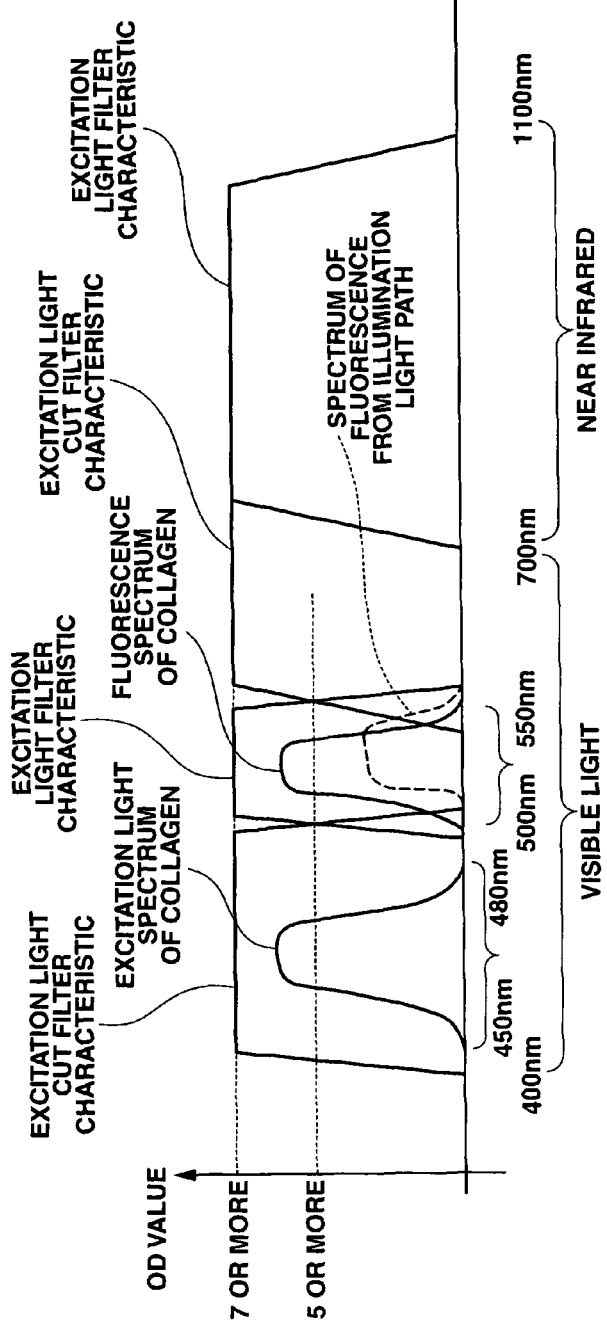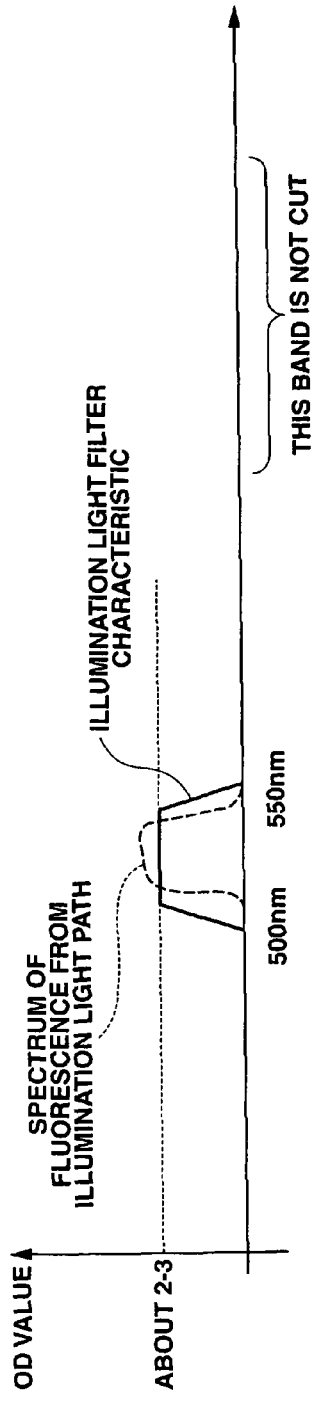

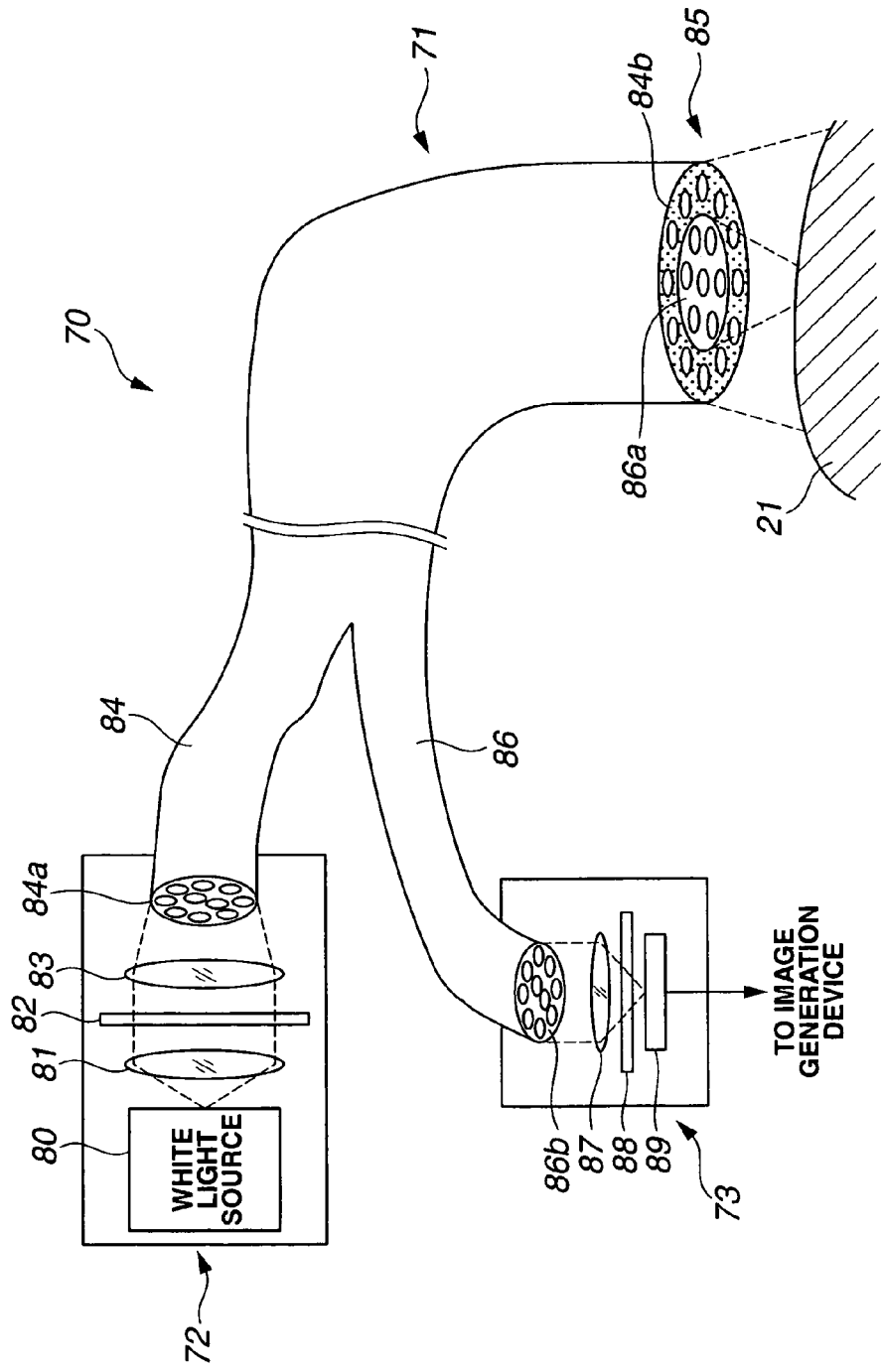

OPTICAL IMAGING DEVICE HAVING ILLUMINATION LIGHT FILTER SECTION

This application claims benefit of Japanese Application No. 2005-252517 filed in Japan on Aug. 31, 2005, and Japanese Application No. 2006-169356 filed in Japan on Jun. 19, 2006, the contents of which are incorporated by this reference.

BACKGROUND OF THE INVENTION

1. Field of the Invention

The present invention relates to an optical imaging device which allows fluorescence observation in which excitation light is irradiated and fluorescence is received from the subject.

2. Description of the Related Art

Endoscope apparatuses have been widely used in medical and other fields. Endoscope apparatuses in the medical field in particular are used for the inspection and observation of a living body, which is the subject.

Such endoscopic observation includes not only normal visible light observation, but also fluorescence observation in which excitation lights are irradiated onto a living body, and fluorescence from a lesioned part is received and converted into an image. To perform this fluorescence observation, a fluorescent substance, such as nematoporplyrin which has an affinity with a lesioned part, such as cancer, is administered into the body of the patient. After a predetermined time elapses after administering the fluorescent substance, excitation lights are irradiated onto the living body, than the fluorescence emitted from the fluorescent substance accumulated in the lesioned part is received and generated into a fluorescent image, and based on this fluorescent image, the status of the lesioned part is judged.

Examples of an endoscope apparatus as an optical imaging device that can acquire such a fluorescent image are disclosed in Japanese Patent Application Laid-Open No. H7-155285, No. H8-224208, No. H11-244220 and No. 2005-58618.

The endoscope apparatuses disclosed in the above mentioned Japanese Patent Application Laid-Open No. H7-155285 and No. H8-224208 are configured such that an optical filter for shielding lights other than fluorescence in the return lights from a subject, which receives irradiated excitation lights, is installed in the previous stage of an image capturing element, so as to acquire the fluorescent image.

The endoscope apparatus disclosed in the above mentioned Japanese Patent Application Laid-Open No. H11-244220 is configured such that a cap, having an optical filter for shielding excitation light in the return lights from the subject, which receives irradiated excitation light, is installed at the distal portion of the endoscope, so as to acquire a fluorescent image.

The endoscope apparatus disclosed in the above mentioned Japanese Patent Application Laid-Open No. 2005-58618 is configured such that a desired cap, out of a cap having an optical filter for transmitting only excitation lights and a cap having an optical filter for shielding only the excitation lights, is installed at the distal portion of the endoscope, and a fluorescent image is acquired when the optical filter for transmitting only the excitation lights is installed at the distal portion.

On the other hand, in Japanese Patent Application Laid-Open No. 2004-294109, for example, a Raman scattering measurement device for measuring Raman scattering lights from the subject is disclosed. This Raman scattering measurement device is configured such that an optical filter for decreasing the Raman scattering lights, generated in the excitation light path, is installed at the tip of the probe.

In these conventional endoscope apparatuses as optical imaging devices, optical elements constructing the illumination light path, such as the lenses in the light source device, light guide and illumination lenses in the insertion section, and the adhesive securing these elements, may generate a slight amount of fluorescence or Raman scattering lights.

In such a case, in a conventional endoscope apparatus, the fluorescence or Raman scattering lights from the illumination light path are mixed into illumination lights which are irradiating the subject as excitation lights, reflected by the subject and enter the endoscope apparatus. If the fluorescence or Raman scattering lights from the illumination light path are included in the transmission wavelength band of the optical filter, in a conventional endoscope apparatus, these fluorescence and Raman scattering lights from the illumination light path are captured by the image capturing element along with the fluorescence generated by the subject.

Particularly, in the case when the positional relationship of the illumination light, subject and light receiving optical system is the positional relationship where the portions satisfy regular reflection conditions, the above mentioned fluorescence and Raman scattering lights from the illumination light path generate brighter images, which makes it difficult to identify whether the light is from fluorescence which comes from the subject or fluorescence or Raman scattering lights which comes from the illumination light path, and interferes with smooth observation.

Generally the intensity of fluorescence generated from the subject is extremely small, compared with the intensity of normal reflected light. Therefore in a conventional endoscope apparatus, it may become difficult to detect only fluorescence which comes from the subject if the reflected light of the fluorescence and Raman scattering lights mix in.

The Raman scattering lights measurement device according to the above mentioned Japanese Patent Application Laid-Open No. 2004-294109, on the other hand, is a device for measuring the spectrum intensity of the Raman scattering lights from the subject (in other words, a device for one-dimensionally measuring the Raman scattering lights), and is not intended to measure fluorescence and white lights other than Raman scattering lights, and particularly is not intended to perform normal endoscopic observation and fluorescent image observation by acquiring two-dimensional images. Therefore this Raman scattering lights measurement device cannot perform normal endoscopic observation and fluorescent image observation simultaneously.

In the case of the endoscope apparatus according to the above mentioned Japanese Patent Application Laid-Open No. 2005-58618, when the cap is attached, lights other than excitation lights are blocked at the distal end of the endoscope, so both normal endoscopic observation and fluorescent image observation cannot be performed in this status. In order to perform both normal endoscopic observation and fluorescent image observation, the endoscope must be extracted from the subject once, the cap is removed, then the endoscope is inserted again into the subject for observation. Therefore this endoscope apparatus is not intended to observe a white reflected light image and a fluorescent image approximately at the same time.

SUMMARY OF THE INVENTION

It is an object of the present invention to provide an optical imaging device that can be used for both fluorescence observation and normal endoscopic observation, and can decrease unnecessary lights that could affect fluorescence observation.

The present invention is an optical imaging device, comprising: a light source for emitting lights including excitation lights and lights in at least a part of the visible light band; an insertion section that can be inserted into a body cavity; a light transmission section which is provided in the insertion section and guides light from the light source to a subject in the body cavity; a light receiving optical system which is provided at a distal portion of the insertion section and receives return lights, from the subject, of the lights guided to the subject by the light transmission section; a reflected light image capturing section for acquiring a reflected light image related to lights in the visible light band in the return lights received by the light receiving optical system; a fluorescent image capturing section for acquiring a fluorescent image related to fluorescence in the return lights received by the light receiving optical system; and an illumination light filter section which is provided in at least one of an optical path of the lights transmitted by the light transmission section and a light emitting end side of the light transmission section, and decreases from the lights transmitted by the light transmission section and guided to the subject, at least light in a band overlapping with the band of lights of which image is captured by the fluorescent image capturing section.

The above and other objects, features and advantages of the invention will become more clearly understood from the following description referring to the accompanying drawings.

BRIEF DESCRIPTION OF THE DRAWINGS

FIG. 3 is a graph depicting the wavelength characteristic of the lights which are transmitted through the light guide in FIG. 2 and have been incident on the illumination lens;

FIG. 4 is a graph depicting the filter characteristic of the illumination light filter in FIG. 2;

FIG. 5 is a graph depicting the wavelength characteristic of the lights which are transmitted through the illumination light filter in FIG. 2 and irradiated onto the subject;

FIG. 6 is a graph depicting the wavelength characteristic of the return lights from the subject in FIG. 2;

FIG. 7 is a graph depicting the filter characteristic of the excitation light cut filter in FIG. 2;

FIG. 8 is a graph depicting the wavelength characteristic of the lights transmitted through the excitation light cut filter in FIG. 2;

FIG. 12 is a graph depicting the wavelength characteristic of the optical imaging device in FIG. 11;

FIG. 13 is a diagram depicting an entire configuration of the optical imaging device according to Embodiment 3;

FIG. 14 is a graph depicting the filter characteristic of the excitation light filter in FIG. 13;

FIG. 15 is a graph depicting the wavelength characteristic of the lights which are transmitted through the excitation light filter in FIG. 13;

FIG. 28 is a graph depicting the filter characteristic of the excitation light filter and excitation light cut filter in FIG. 27;

FIG. 29 is a graph depicting the filter characteristic of the illumination light filter in FIG. 27;

FIG. 51 is a diagram depicting an entire configuration of the optical probe device constituting the optical imaging device according to Embodiment 6;

DESCRIPTION OF THE PREFERRED EMBODIMENTS

Embodiments of the present invention will now be described with reference to the drawings.

Embodiment 1

Figure 1:
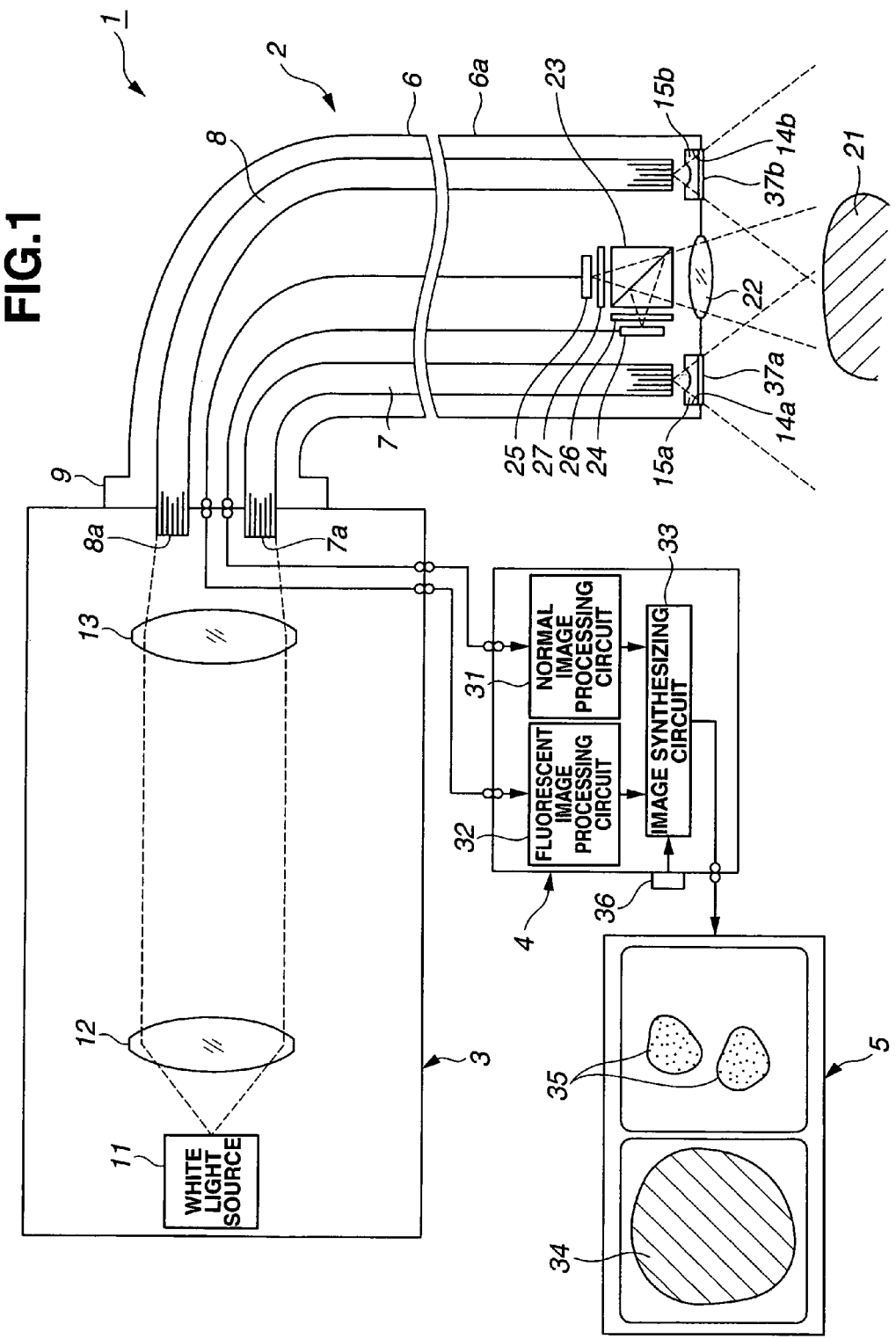
FIG. 1 is a diagram depicting an entire configuration of the optical imaging device according to Embodiment 1.
Figure 2:
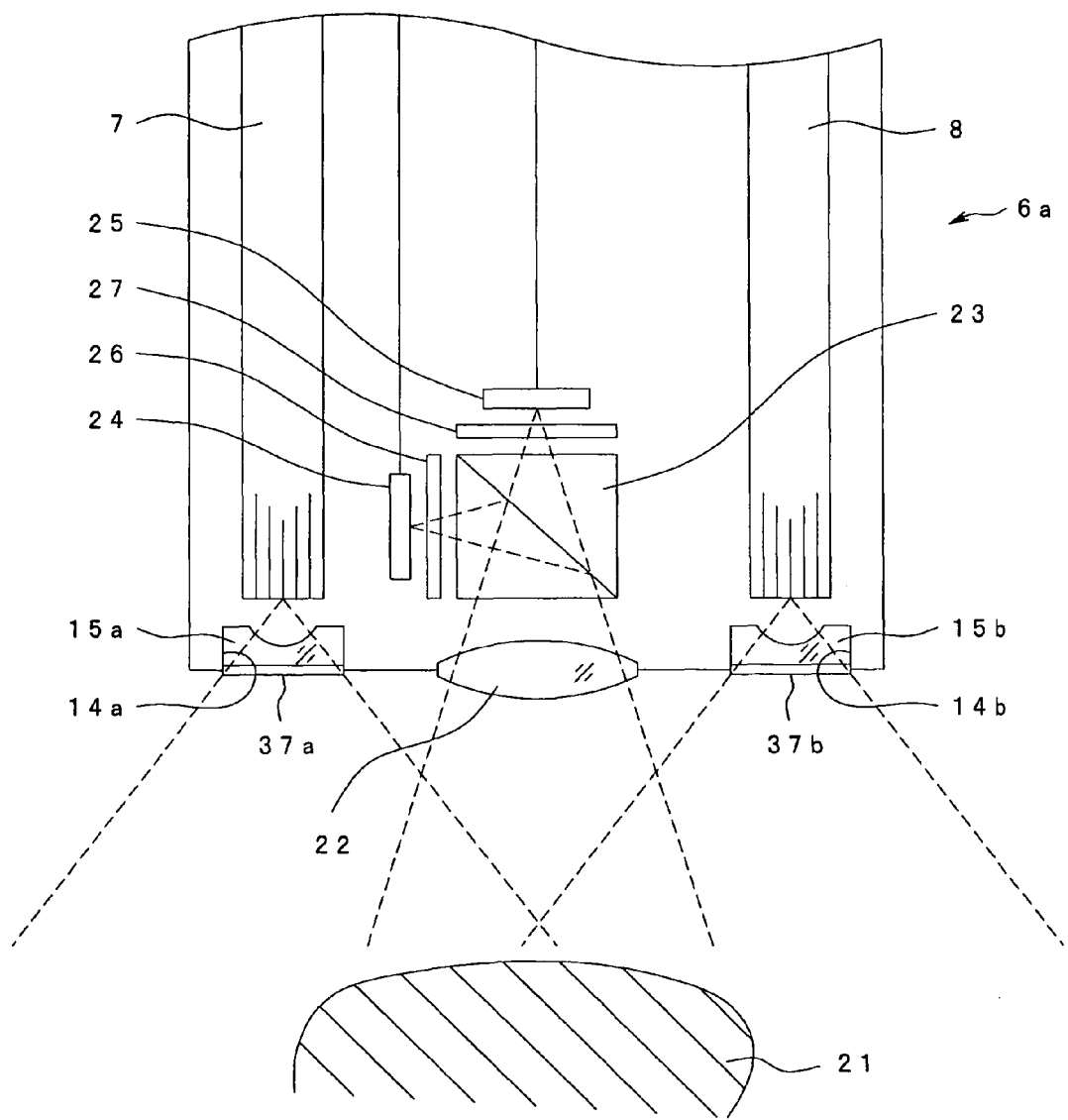
FIG. 2 is an enlarged view depicting a key section at the distal portion of the insertion section of the endoscope shown in FIG. 1.
Figure 9:
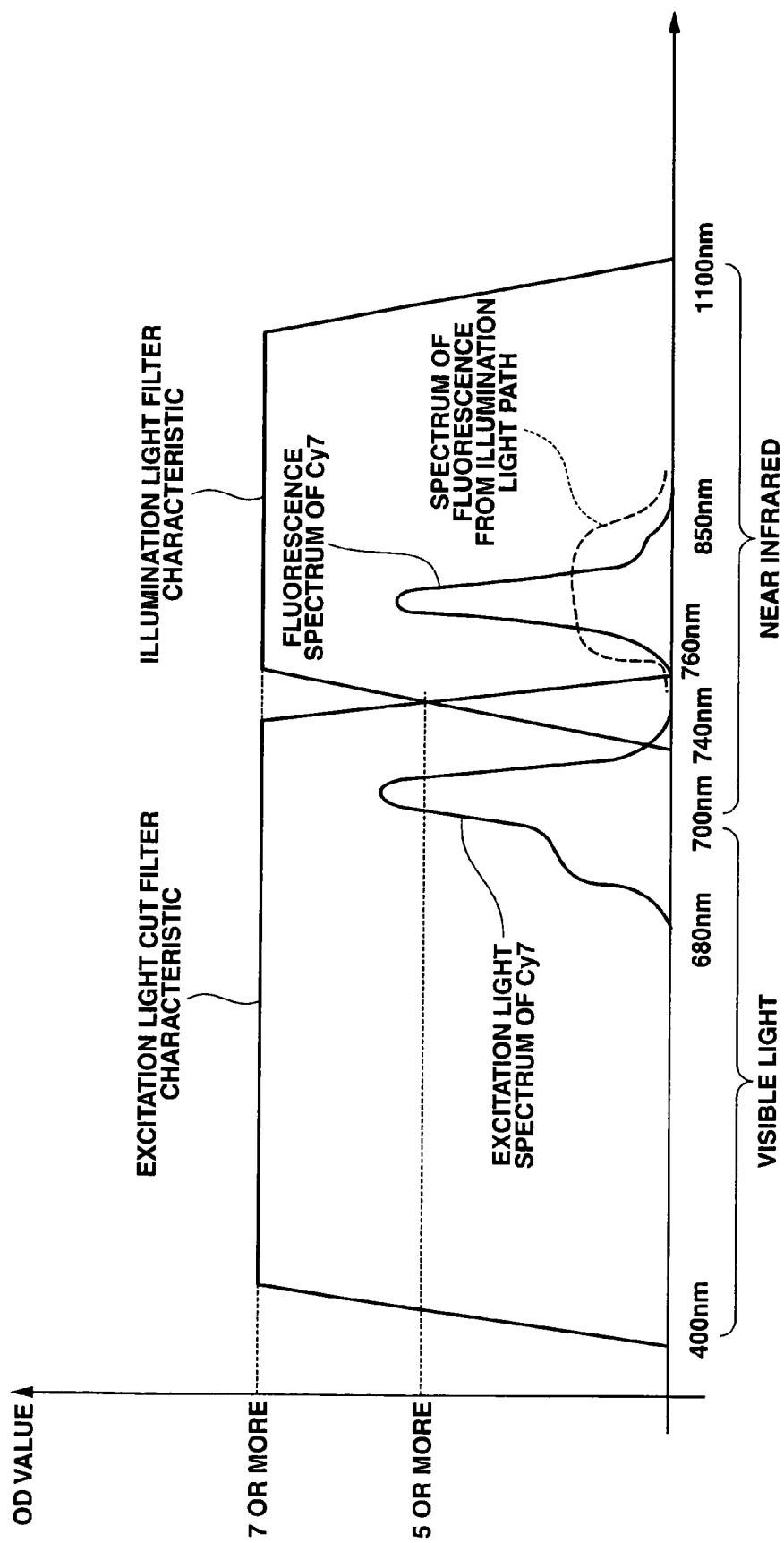
FIG. 9 is a graph depicting the wavelength characteristic when the graphs in FIG. 3 to FIG. 8 are combined into one.
Figure 10:
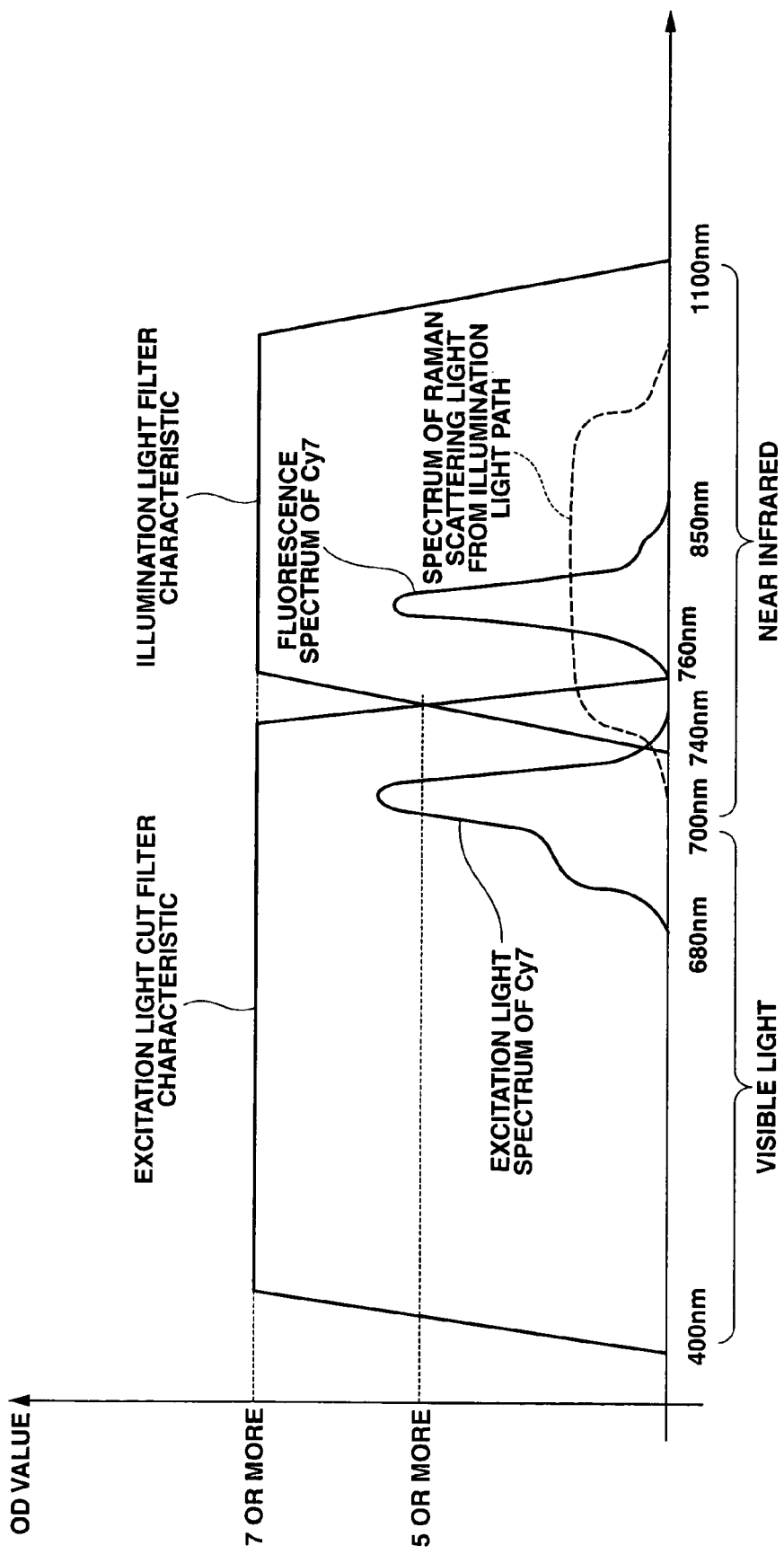
FIG. 10 is a graph depicting the wavelength characteristic when the Raman scattering lights which come from the illumination light path are added in FIG. 9, instead of the fluorescence which come from the illuminated light path.

FIG. 1 to FIG. 10 are related to Embodiment 1 of the present invention, where FIG. 1 is a diagram depicting an entire configuration of the optical imaging device according to Embodiment 1, FIG. 2 is an enlarged view depicting a key section at the distal portion of the insertion section of the endoscope shown in FIG. 1, FIG. 3 is a graph depicting the wavelength characteristic of the lights which are transmitted through the light guide in FIG. 2 and entered the illumination lens, FIG. 4 is a graph depicting the filter characteristic of the illumination light filter in FIG. 2, FIG. 5 is a graph depicting the wavelength characteristic of the lights which are transmitted through the illumination light filter in FIG. 2 and irradiated onto the subject, FIG. 6 is a graph depicting the wavelength characteristic of the return light from the subject in FIG. 2, FIG. 7 is a graph depicting the filter characteristic of the excitation light cut filter in FIG. 2, FIG. 8 is a graph depicting the wavelength characteristic of the lights transmitted through the excitation light cut filter in FIG. 2, FIG. 9 is a graph depicting the wavelength characteristic when the graphs in FIG. 3 to FIG. 8 are combined into one, and FIG. 10 is a graph depicting the wavelength characteristic when the Raman scattering lights which come from the illumination light path are added in FIG. 9, instead of the fluorescence which come from the illumination light path.

As FIG. 1 shows, the optical imaging device 1 of Embodiment 1 comprises an endoscope 2 that can be inserted into a body cavity, a light source device 3 for supplying illumination light to the endoscope 2, an image generation device 4 as an image generation section for signal processing of image generation based on the signals that are output from the light detection section (image capturing section) built in the endoscope 2, and a monitor 5 as an image display screen for displaying image captured by the image capturing section by inputting image signals (video signals) generated by the image generation device 4.

The endoscope 2 has a thin and long insertion section 6 which is structured to insert into a body cavity easily. In the insertion section 6, a light guide section, two light guides 7 and 8, for example, for guiding light supplied from the light source device 3 to the distal end of the insertion section 6, are inserted through. At the proximal end of the endoscope 2, a connector 9 is attached. The connector 9 is for freely detachably connecting the endoscope 2 to the light source device 3. When the endoscope 2 is connected to the light source device 3, the illumination lights from the light source device 3 is incident on the light incident ends 7*a* and 8*a* of the light guides 7 and 8, which are exposed at the back end side of the connector 9.

In the light source device 3, a white light source 11, collimator lens 12 and condenser lens 13 are installed. Lights from the white light source 11 are converted into roughly parallel beams by the collimator lens 12, serving as the illumination light guiding optical system, then are condensed by the condenser lens 13, and are incident on the above mentioned light incident ends 7*a* and 8*a* of the light guides 7 and 8. In this way, the illumination lights which entered the light incident ends 7*a* and 8*a* are transmitted (guided) to the light emitting ends of the light guides 7 and 8 via the light guides 7 and 8 respectively.

Each light emitting end of the light guides 7 and 8 is fixed in the distal portion 6*a* of the insertion section 6. And illumination window sections 14*a* and 14*b* are installed at the distal portion 6*a* of the insertion sections 6 to be the illumination light emitting windows, so as to face each light emitting end of the light guides 7 and 8. In the illumination window sections 14*a* and 14*b*, illumination lenses (plano-concave lenses) 15*a* and 15*b* are installed respectively to serve as the illumination optical system. Therefore the illumination lights emitted from the light emitting ends of the light guides 7 and 8 spread via each illumination lens 15*a* and 15*b* facing each light emitting end, and are irradiated onto the subject 21. The above mentioned light guides 7 and 8 and illumination lenses 15*a* and 15*b* constitute the light transmission section.

In the position between the two illumination window sections 14*a* and 14*b*, in an intermediate position, for example, an observation window or a light receiving window is created. In the observation window or light receiving window, an objective lens 22 is provided to serve as a light receiving optical system for receiving the reflected lights, which are the return lights from the subject 21, or the fluorescence generated by irradiation of the excitation lights. The objective lens 22 is for forming an optical image in the image capturing section placed at the image forming position. Back from the image forming position on the optical axis of the observation lens 22, a beam splitter (or half prism) 23 is placed. The beam splitter 23 separates light which are incident from the subject 21 into two by reflecting a part thereof and transmitting the rest.

At the reflection side of the image forming position of the beam splitter 23, an image capturing section 24 for capturing normal images (reflected light image capturing section), is placed, and at the transmission side image forming position, an image capturing position 25 for capturing a fluorescent image (fluorescent image capturing section), is placed. These image capturing sections 24 and 25 constitute a light detection section, and have solid image capturing elements, such as CCD (Charge Coupled Device) or CMOS (Complementary Metal Oxide Semiconductor).

Back to the image capturing face (light receiving face) of the image capturing section 24, for capturing normal images (between the image capturing section 24 and beam splitter 23), a visible light transmission filter (hereafter called visible light filter) 26, which is set to a characteristic to transmit visible lights, is placed. The visible light filter 26 transmits only lights with a wavelength band of 400 to 700 nm, for example, as visible lights.

In front of the image capturing face (light receiving face) of the image capturing section 25 for capturing fluorescent images (between the image capturing section 25 and beam splitter 23), an excitation light cut filter (or fluorescence transmission filter) 27, which is set to a characteristic to cut (shield) the excitation lights and transmit fluorescence, is placed as the light receiving filter section. The filter characteristic of the excitation light cut filter 27 will be described later.

The image capturing sections 24 and 25 are connected to a normal image processing circuit 31 and a fluorescent image processing circuit 32 created in the image generation device 4 respectively, via a signal line penetrating the insertion section 6 and a signal line placed in the light source device 3. The normal image processing circuit 31 and fluorescent image processing circuit 32 incorporate an image capturing drive circuit, which is not illustrated, respectively. And each image capturing drive circuit applies image capturing drive signals respectively to each corresponding image capturing section 24 and 25, performs photoelectric conversion on the received lights, and outputs the image capturing signals acquired by the photoelectric conversion from each image capturing section 24 and 25 respectively.

Then the normal image processing circuit 31 performs processing to generate normal images based on the image capturing signals received from the image capturing section 24. In the same way, the fluorescent image processing circuit 32 performs processing to generate fluorescent images based on the image capturing signals received from the image capturing section 25. By the normal image processing circuit 31 and fluorescent image processing circuit 32, the generated image signals (video signals) of the normal image and image signals (video signals) of the fluorescent images are output to the monitor 5 via an image synthesizing circuit 33 as the image synthesizing section for synthesizing images. On the display screen of the monitor 5, the normal image 34 and fluorescent image 35 are displayed side by side, for example, as a synthesized image.

The image generation device 4 has a display select switch 36 for selecting an image to be displayed on the display screen. The display select switch 36 is for selecting one of synthesized image, the normal image without composition processing or the fluorescent image without composition processing, to be displayed on the display screen of the monitor 5. Therefore if the synthesized image is selected by the display select switch 36, the image synthesizing circuit 33 performs composition processing. If the normal image is selected by the display select switch 36, the image synthesizing circuit 33 outputs only the normal image to the monitor 5 without executing composition processing. If the fluorescent image is selected by the display select switch 36, the image synthesizing circuit 33 outputs only the fluorescent image to the monitor 5 without performing composition processing.

Among the optical elements constituting the illumination light path, such as lenses in the light source device 3, the light guides 7 and 8 in the insertion section 6, the illumination lenses 15*a* and 15*b*, and the adhesives used for securing these elements, some elements may include a substance which may generate a slight amount of fluorescence or Raman scattering lights. In such a case, the fluorescence or Raman scattering lights from the illumination light path may mix into the illumination lights irradiating onto the subject, which affects the fluorescent image captured by the image capturing section 25, which is the fluorescent image capturing section.

Such fluorescence or Raman scattering lights from the illumination light path are not specific to the subject 21, but depend on the conditions of irradiating the lights. Therefore the present embodiment is configured such that the fluorescence and Raman scattering lights from the illumination light path (in other words, lights in the band which overlap the band of lights of which image is captured by the image capturing section 25 via the excitation light cut filter 27 in the illumination lights) (that is unnecessary lights which may affect fluorescence observation) are not substantially included (e.g. shielded) in the illumination lights irradiated onto the subject 21.

Specifically, the illumination light filters 37a and 37b, serving as the illumination light filter sections for shielding lights with a predetermined wavelength, are placed at the light emitting ends of the illumination lenses 15a and 15b respectively, as shown in FIG. 2.

These illumination light filters 37a and 37b are, for example, optical thin films formed on the light emitting end faces of the illumination lenses 15a and 15b. These optical thin films are dielectric thin films, such as $Ta_2O_5$ (tantalum pentaoxide), $SiO_2$ (silicon dioxide) and $TiO_2$ (titanium dioxide), for example. And this dielectric thin film is formed by vacuum evaporation, such as ion plating, physical vapor deposition, such as sputtering, or chemical vapor deposition, such as CVD.

The illumination light filters 37a and 37b have characteristics to transmit the visible lights and excitation lights, and to shield near infrared, as mentioned later in FIG. 4. In the present embodiment, near infrared fluorescence observation is performed by detecting fluorescence in the near infrared band due to the fact that the absorption of near infrared to a living body is small. Since the illumination light filters 37a and 37b have the above characteristics, fluorescence from the illumination light path, which could be included in the wavelength band of near infrared, can be decreased. Details of the characteristics and functions of the illumination light filters 37a and 37b will be described later.

Now the functions of Embodiment 1 based on this configuration will be described.

The optical imaging device 1 shown in FIG. 1 starts operation by operating the power supply switch, which is not illustrated, in the status where the endoscope 2 is connected to the light source device 3. The operator inserts the insertion section 6 of the endoscope 2 into the body cavity, and guides the distal portion 6a of the insertion section 6 to the target region. When the distal portion 6a is guided to the target region, the operator performs fluorescence observation.

In other words, the operator administers the fluorescent substance to the body of the patient in advance. This fluorescent substance accumulates in the lesioned part when a predetermined time has elapsed after administration. In the present embodiment, it is assumed that infrared fluorescence observation is performed using fluorescence die Cy (carbocyanine) 7 as the fluorescent substance. For the fluorescence die Cy 7, the wavelength band of the excitation lights is 680 to 740 nm, wavelength band of fluorescence is 760 to 850 nm, excitation light peak wavelength is 730 nm and fluorescence peak wavelength is 770 nm respectively (see FIG. 9).

The operator inserts the insertion section 6 of the endoscope 2 into the body cavity of the patient, and guides the distal portion 6a to the target region. Until the distal portion 6a of the insertion section 6 is guided to the target region, the operator displays only the normal image on the display screen of the monitor 5 by operating the display select switch 36. When the distal portion 6a of the insertion section 6 reaches the target region, the operator starts infrared fluorescence observation.

Light from the white light source 11 is incident on the light incident ends 7a and 8a of the light guides 7 and 8. The light is transmitted by the light guides 7 and 8, is emitted from the light emitting ends of the light guides 7 and 8, and is incident on the illumination lenses 15a and 15b.

The light which has been incident on the illumination lenses 15a and 15b include fluorescence from the illumination light path, as shown in FIG. 3, for example. In the graph in FIG. 3, the abscissa includes the wavelength and the ordinate indicates the intensity. The fluorescence from the illumination light path exists around the fluorescence wavelength band 760 to 850 nm of the fluorescence dye Cy 7. The image capturing sections 24 and 25 do not have sensitivity to the lights of which wavelength is 1100 nm or longer, so as FIG. 3 shows, signals are not output for the lights of which wavelength is 1100 nm or longer, even if received.

The light which has been incident on the illumination lenses 15a and 15b are irradiated onto the subject 21 via the illumination light filters 37a and 37b. The illumination light filters 37a and 37b have the filter characteristics shown in FIG. 4, for example. In the graph in FIG. 4, the abscissa indicates the wavelength and the ordinate indicates the OD (Optical Density) value. The intensity of the light transmitted through the filter with OD value n is $10^{-n}$ of the original light. For example, if a light with 10 mW transmits through the filter with OD value 7, the intensity of the light is $10\ mW \times 10^{-7} = 1$ nW.

The illumination light filters 37a and 37b are transmitted through the wavelength band 400 to 750 nm, including the visible light and excitation light 680 to 740 nm of fluorescence dye Cy 7, and shield near infrared 750 to 1100 nm including the fluorescence from the illumination light path with an OD value of 7 or more. Therefore the light that is transmitted through the illumination light filters 37a and 37b and is irradiated onto the subject 21 is only illumination light with a 400 to 750 nm wavelength band including the excitation light 680 to 740 nm of the fluorescence dye Cy 7, as shown in FIG. 5. In the graph in FIG. 5, the abscissa indicates the wavelength and the ordinate indicates the intensity.

By this, only lights with the wavelength band 400 to 750 nm of visible light and excitation light, where the near infrared 750 to 1100 nm including the fluorescence from the illumination light path are shielded, are irradiated onto the subject 21.

Since near infrared including fluorescence from the illumination light path is shielded, the return lights from the subject 21 are only the fluorescence generated by the fluorescence dye Cy 7 included in the subject 21 and reflected visible light from the subject 21, which are entered through the objective lens 22.

In other words, as shown in FIG. 6, the return lights from the subject 21 are only the wavelength band 400 to 750 nm of the visible light reflected from the subject 21 and the wavelength band 760 to 850 nm of the fluorescence generated by the fluorescence dye Cy 7 included in the subject 21. In the graph in FIG. 6, the abscissa indicates the wavelength and the ordinate indicates the intensity. The return lights from the subject 21 enter the objective lens 22 and are separated into two by the beam splitter 23. Out of the lights separated by the beam splitter 23, the reflected light, is formed into an image at the image capturing section 24 via the visible light filter 26, and the transmitted light is formed into an image at the image capturing section 25 via the excitation light cut filter 27.

The excitation light cut filter 27 has the filter characteristic shown in FIG. 7. In the graph shown in FIG. 7, the abscissa indicates the wavelength and the ordinate indicates the OD value. As FIG. 7 shows, the excitation light cut filter 27 shields the wavelength band 400 to 750 nm of visible light with an OD value of 7 or more, and transmits lights with other wavelength bands.

Therefore the light transmitted through the excitation light cut filter 27 is substantially only the wavelength band 760 to 850 nm of the fluorescence generated by the fluorescence dye Cy 7, as shown in FIG. 8. In the graph in FIG. 8, the abscissa indicates the wavelength and the ordinate indicates the intensity.

FIG. 9 shows the combined graph of FIG. 3 to FIG. 8. As FIG. 9 shows, in the graph in FIG. 9, the abscissa indicates the wavelength and the ordinate indicates the OD value. As FIG. 9 shows, the illumination light filters 37a and 37b shield the wavelength band 750 to 1100 nm of near infrared, including the fluorescence from the illumination path, with an OD value of 7 or more, and transmits only the wavelength band 400 to 750 nm of the illumination light, including the wavelength band 680 to 740 nm of the excitation light of fluorescence dye Cy 7. The excitation light cut filter 27 shields the wavelength band 400 to 750 nm of visible light with an OD value of 7 or more, and transmits only the wavelength band 760 to 850 nm of fluorescence generated by the fluorescence dye Cy 7. The intersections of the shielded band of the illumination light filters 37a and 37b and the shielded band of the excitation light cut filter 27 have an OD value of 5 or more.

Therefore the image capturing section 25 can receive only wavelength 760 to 850 nm of the fluorescence generated by the fluorescence dye Cy 7.

The information of the light received by the image capturing section 24 is output to the monitor 5 as a normal image, via the normal image processing circuit 31 and image synthesizing circuit 33. The information of the light received by the image capturing section 25 is output to the monitor 5 as the fluorescent image via the fluorescent image processing circuit 32 and image synthesizing circuit 33. And on the display screen of the monitor 5, the normal image 34 and fluorescent image 35 are displayed side by side.

As a result, the optical imaging device 1 of the present embodiment can decrease fluorescence from the illumination light path in the near infrared band, and can suppress the generation of light to be the noise source. As described above, in the portion where the positional relationship of the illumination light, subject and light receiving optical system satisfy the regular reflection conditions, fluorescence from the illumination light path is displayed especially brightly, and it becomes difficult to identify fluorescence from subject if no countermeasures are taken. A device for performing two-dimensional observation, such as the optical imaging device 1, often uses an optical system having a wide field angle as the objective lens 22, so it is quite possible that the positional relationship satisfies regular reflection conditions. Therefore the effectiveness of shielding the light which may affect fluorescence observation just before irradiating onto the subject 21 is enormous. Also in the optical imaging device 1 of the present embodiment, the illumination light filters 37a and 37b transmit the entire band of visible light, so both the normal image 34 and fluorescent image 35 can be simultaneously acquired.

The optical imaging device 1 can also decrease the Raman scattering light from the illumination light path in the near infrared band, as shown in FIG. 10. If Raman scattering is generated, light which is shifted from the illumination light for a predetermined wavelength amount are generated. For example, if a 200 nm shift is generated in Raman scattering, and if the wavelength band of the illumination light is 400 to 750 nm, then Raman scattering light is generated in a wavelength band of about 600 to 950 nm.

The optical imaging device 1 can decrease the Raman scattering light from the illumination light path by shielding the Raman scattering light from the illumination light path, in the same way as the case of fluorescence from the illumination light path, using the illumination light filters 37a and 37b, and therefore can acquire both the normal image 34 and fluorescent image 35.

In this way, the optical imaging device 1 of the present embodiment, where the illumination light filters 37a and 37b are installed at the light emitting end of the illumination lenses 15a and 15b, can be used for both fluorescence observation and normal endoscopic observation, and can decrease the fluorescence and Raman scattering light that come from the illumination light path. In the present embodiment, a configuration using two light guides 7 and 8 is described as an example, but a configuration using three or more light guides may be used.

Embodiment 2

Figure 11:
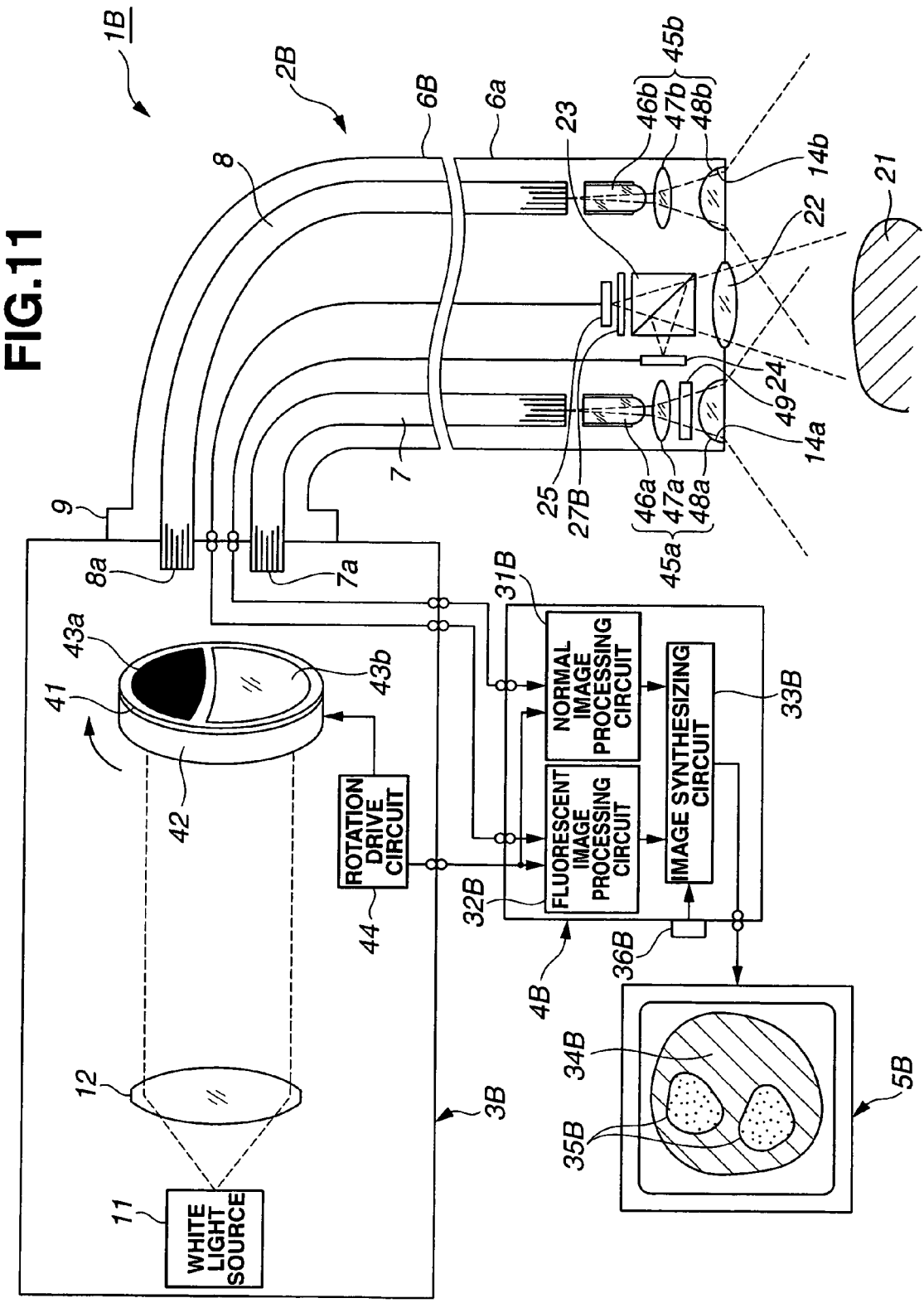
FIG. 11 is a diagram depicting an entire configuration of the optical imaging device according to Embodiment 2.

FIG. 11 to FIG. 12 are related to Embodiment 2 of the present invention, where FIG. 11 is a diagram depicting an entire configuration of the optical imaging device according to Embodiment 2, and FIG. 12 is a graph depicting the wavelength characteristic of the optical imaging device in FIG. 11. The above Embodiment 1 has a configuration where the present invention is applied to the optical imaging device which performs infrared fluorescence observation by detecting the fluorescence in the near infrared band, but Embodiment 2 has a configuration where the present invention is applied to an optical imaging device which performs visible light fluorescence observation by detecting the fluorescence in the visible light band. The rest of the configuration is the same as Embodiment 1, therefore description thereof is omitted, and the same components are described denoting with the same reference symbols.

As FIG. 11 shows, the optical imaging device 1B of Embodiment 2 is configured such that visible light fluorescence observation is possible. A light source device 3B has a circular rotary disk 41 on which light from the white light source 11 is incident, the lights having been converted into roughly parallel beams by the collimator lens 12. The rotary disk 41 is attached to a motor 42 which is comprised of a ring type ultrasonic motor, for example.

On the rotary disk 41, a shielding section 43a and a transmission section 43b are arranged to be roughly semi-circular respectively. The light which has been incident on the rotary disk 41 is shielded by the shielding section 43a but is transmitted by the transmission section 43b. Therefore the light is incident on the portions facing the transmission section 43b, out of the light incident ends 7a and 8a of two light guides 7 and 8 passing through the endoscope 2B. The rotary disk 41 is configured such that when the rotary disk 41 is rotated by about a ¼ rotation from the rotation position shown in FIG. 11, light transmitted through the transmission section 43b can be incident on both of the light incident ends 7a and 8a. The motor 42 rotates at a predetermined speed, such as one revolution per second by drive signal from a rotation device circuit 44. And by the rotary disk 41 installed in the motor 42 being rotated according to the rotation of the motor 42, the light which has been incident on the rotary disk 41 alternately is incident on the two light guides 7 and 8.

In the endoscope 2B, illumination optical systems 45a and 45b are provided so as to face the light emitting ends of the light guides 7 and 8 respectively. These illumination optical systems 45a and 45b include the rod lenses 46a and 46b, relay lenses (biconvex lenses) 47a and 47b, and illumination lenses (plano-convex lenses) 48a and 48b positioned at illumination window sections 14a and 14b to be the illumination light emitting windows respectively. And an illumination light filter 49, having the later mentioned optical characteristic, is placed only on the illumination optical system 45a out of these composing elements. The illumination lights emitted from the light emitting ends of the light guides emitted 7 and 8 are spread via each illumination optical system 45a and 45b facing these light emitting ends, and irradiated to the subject 21.

The two illumination window sections 14a and 14b are formed at different positions on the end face of the distal portion 6a. The illumination lights from the two illumination window sections 14a and 14b at different positions are irradiated onto the subject 21 alternately (in other words, at different timings). This means that in the present embodiment, an irradiation window switching section is formed, for irradiating the illumination lights from the white light source 11 onto the subject 21 from the illumination window sections 14a and 14b as the irradiation windows at two different positions by switching the timing. In the present embodiment, both the fluorescent image in the visible light band and the normal image can be acquired by alternately irradiating illumination lights with a different wavelength band from the illumination window sections 14a and 14b at different positions, as described later.

The rotary drive circuit 44 transmits the synchronous signal synchronized with the rotation of the rotary disk 41 to a normal image processing circuit 31B and a fluorescent image processing circuit 32B of the image generation device 4B. The normal image generation circuit 31B and fluorescent image processing circuit 32B perform processing to generate the normal image and fluorescent image synchronizing with the received synchronization signal.

The normal image processing circuit 31B and fluorescent image processing circuit 32B incorporate an image capturing drive circuit, which is not illustrated, respectively. Each image capturing drive circuit applies image capturing drive signal to the image capturing sections 24 and 25 respectively, synchronizing with synchronization signal, performs photoelectric conversion on the lights received by the image capturing sections 24 and 25, and outputs the acquired image capturing signals. In the above description, the rotary drive circuit 44 generates the synchronization signal and sends it to the image generation drive 4B, but the image generation drive 4B may generate the synchronization signal and send the generated synchronization signal to the rotary drive circuit 44.

Image signal (video signal) of the normal image and image signal (video signal) of the fluorescent image generated by the normal image processing circuit 31B and fluorescent image processing circuit 32B respectively are output to a monitor 5B via an image synthesizing circuit 33B which synthesizes images, and are displayed on the display screen of the monitor 5B in a composite state of the normal image and fluorescent image, for example.

The image synthesizing circuit 33B superimposes the signal portion of the fluorescent image on the normal image. In this case, the image portion, where the fluorescent image is superimposed, of the normal image is removed by mask processing.

In this way, the image synthesizing circuit 33B composes the signal portion of the fluorescent image and the normal image and displays the synthesized image, so the position and contour of the affected region can be easily identified by the normal image portion, and a lesioned part or tumor region can be easily diagnosed by the fluorescent image portion.

An image generation device 4B is configured such that the images to be synthesized by the image synthesizing circuit 33B can be selected according to the selection operation of a display section switch 36B. For example, the image synthesizing circuit 33B can illuminate based on the timing when both of the light guides 7 and 8 become transmission status according to the selection operation of the display select switch 36B, synthesize the images captured in this state, and display the synthesized image on a monitor 5B.

The monitor 5B shown in FIG. 11 shows a display example of the images acquired in this state. Here a reference symbol 34B shows the normal image, and 35B shows the fluorescent image by the fluorescence generated by the excitation lights irradiated onto the subject 21.

The image captured in a state being illuminated alternately by the two light guides 7 and 8 may be displayed on the monitor 5B by the select operation of the display select switch 36B. In this case, an image captured when one of the light guides 7 and 8 is in shielded status is displayed in synchronization with the rotation of the rotary disk 41, for example.

Now the fluorescent image in the present embodiment will be described. In the present embodiment, the fluorescent images are acquired by receiving fluorescence from the endogenous fluorescent substance existing in a living body. Examples of the endogenous fluorescent substance are riboflavin, tryptophan, tyrosine, NADH (Nicotinamide adenine dinucleotide), NADPH (nicotinamide adenine dinucleotide phosphate), porphyrin, collagen, elastin, fibronectin and FAD (flavin adenine dinucleotide).

If excited by about a 450 nm wavelength light, normal tissue emits about a 520 nm wavelength fluorescence. Whereas the fluorescence of a cancer focus is significantly weaker than the fluorescence of a normal area, since fluorescence generated from the endogenous fluorescent substance is weakened as the carcinogenic stage of the tissue progresses. Therefore according to the configuration of the present embodiment, the fluorescence or Raman scattering light from the illumination light path generated in the visible light band are shielded, and then a fluorescent image in the visible light band is acquired.

Specifically, the illumination optical system 45a includes of an illumination light filter 49, which is installed on an optical path between the relay lens 47a and illumination lens 48a, for example. The illumination light filter 49 is provided as an interference filter or an absorption filter, and has the function to shield the fluorescence or Raman scattering light from the illumination light path which appear in the visible light band (see FIG. 12).

In front of the image capturing face (light receiving face) of the image capturing section 25 for capturing fluorescent images, an excitation light cut filter 27B is placed. The excitation light cut filter 27B has an optical characteristic of cutting (shielding) the excitation light which appears in the visible light band, and transmitting fluorescence from the subject (see FIG. 12).

The function of Embodiment 2 based on this configuration will be described.

As FIG. 11 shows, the optical imaging device 1B is activated by operating the power supply switch, which is not illustrated, in a state where the endoscope 2B and the like are connected to the light source device 3B. The operator inserts the insertion section 6B of the endoscope 2B into the body cavity, guides the distal portion 6a of the insertion section 6B to a target region, and performs fluorescence observation. In the present embodiment, it is assumed that visible light fluorescence observation is performed using collagen, out of the above mentioned endogenous fluorescent substance examples.

The operator inserts the insertion section 6B of the endoscope 2B into the body cavity of the patient, and guides the distal portion 6a into the target region. Until the distal portion 6a of the insertion section 6B is guided to the target region, the operator displays only the normal image on the display screen of the monitor 5B by operating the display select switch 36B.

When the distal portion 6a of the insertion section 6B reaches the target region, the operator starts visible light fluorescence observation. During the visible light fluorescence observation, the motor 42 rotates at a constant speed, and the rotary disk 41 also rotates according to the rotation of the motor 42. Light from the white light source 11 is incident on both light guides 7 and 8 alternately via the transmission section 43b of the rotary disk 41.

In the state where the shielding section 43a is facing the light entering end 7a of the light guide 7, light from the white light source 11 transmitted through the transmission section 43b is incident on the light entering end 8a of the other light guide 8. Light having been incident on the light entering end 8a is transmitted by the light guide 8, and are irradiated from the distal end face. The light is irradiated onto the subject 21 via the illumination optical system 45b.

When the rotary disk 41 rotates a half turn from the above status, the shielding section 43a faces the light entering end 8a of the light guide 8, and the light from the white light source 11 transmitted through the transmission section 43b is incident on the light entering end 7a of the light guide 7. The light which is incident on the light entering end 7a is transmitted by the light guide 7, and is irradiated from the distal end face. The light is irradiated onto the subject 21 via the illumination optical systems 45a. At this time, as FIG. 12 shows, the lights transmitted by the light guide 7 and having being incident on the illumination optical system 45a include fluorescence or Raman scattering lights from the illumination light path. The fluorescence or Raman scattering light from the illumination light path exist in the band around 520 nm, which is the fluorescent peak wavelength of collagen.

The illumination light filter 49 arranged in the illumination optical system 45a shields the wavelength band 500 to 550 nm, including around 520 nm of fluorescence of collagen and the wavelength band 700 to 1100 nm of near infrared with an OD value of 7 or more, and transmits 400 to 480 nm and 550 to 700 nm of the visible light bands including around 450 nm of excitation light of collagen.

Therefore light which is transmitted through the illumination light filter 49 and is irradiated onto the subject 21 are only the 400 to 480 nm and 550 to 740 nm visible light band, including around 450 nm of excitation light of collagen.

Because of this, only 400 to 480 nm and 550 to 740 nm of the visible light band are irradiated onto the subject 21, and the wavelength band 500 to 550 nm including around 520 nm of fluorescence of collagen where fluorescence or Raman scattering light from the illumination light path are included, and the wavelength band 700 to 1100 nm of near infrared are shielded.

Since a part of the visible light band where fluorescence or Raman scattering light from the illumination light path are included is shielded in this way, the return lights from the subject 21 include only the fluorescence generated by the collagen included in the subject 21 and the reflected visible light from the subject 21. These return lights from the subject 21 enter through the objective lens 22. The return lights from the subject 21, which have been incident on the objective lens 22, are split into two by a beam splitter 23. Out of these lights split by the beam splitter 23, the reflected light forms an image at the image capturing section 24, and the transmitted light forms an image at the image capturing section 25 via the excitation light cut filter 27B.

The excitation light cut filter 27B shields the wavelength bands 400 to 500 nm and 550 to 700 nm with an OD value of 7 or more, and transmits lights with the other wavelength bands.

Therefore the light transmitted through the excitation light cut filter 27B is only the wavelength band 500 to 550 nm including around 520 nm of the fluorescence generated by collagen, and form an image at the image capturing section 25.

The information of the light received by the light capturing section 24 is output to the monitor 5B as the normal image via the normal image processing circuit 31B and image synthesizing circuit 33B. The information of the light received by the image capturing section 25 is output to the monitor 5B as the fluorescent image via the fluorescent image processing circuit 32B and image synthesizing circuit 33B. In this way, on the display screen of the monitor 5B, a synthesized image of the normal image 34B and fluorescent image 35B is displayed as one synthesized image.

As a result, the optical imaging device 1B of Embodiment 2 can decrease the fluorescence or Raman scattering light from the illumination light path in the visible light band, and can acquire both the normal image 34B and fluorescent image 35B. Since the illumination light filter 49 is provided only in one of the two illumination light paths, and illumination light path at the light guide 8 side where the illumination light filter is not installed is used during normal endoscopic observation, so a situation can be prevented where a color in normal endoscopic observation is displayed differently from the actual color by installing an illumination light filter for shielding a part of the visible light at the tip.

Embodiment 3

Figure 16:
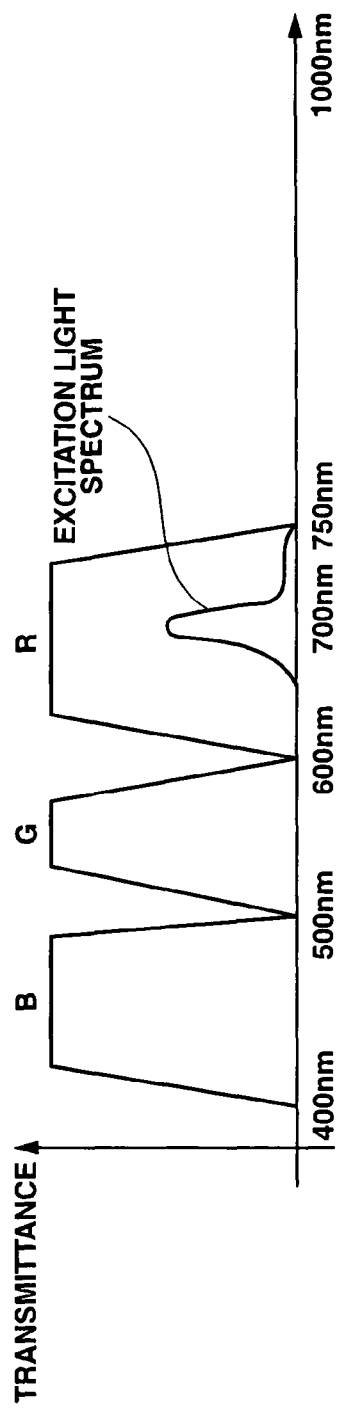
FIG. 16 is a graph depicting the filter characteristic of the RGB filter in FIG. 13.
Figure 17:
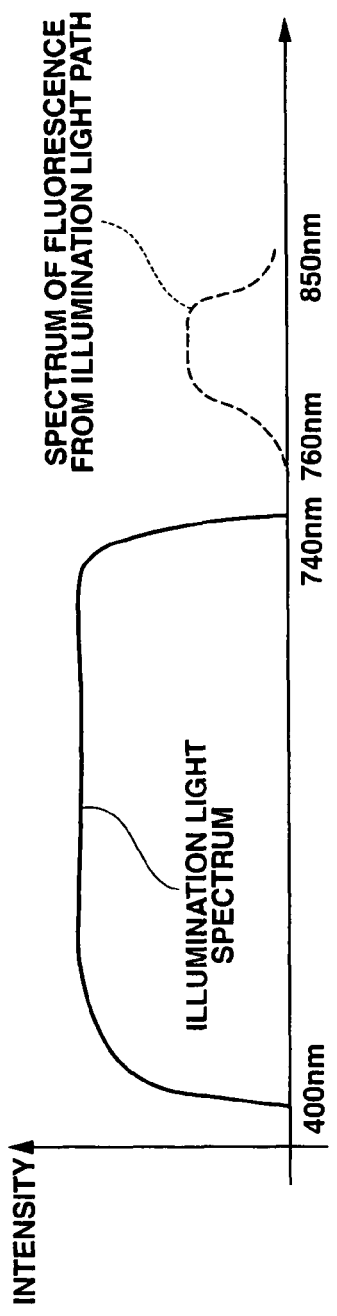
FIG. 17 is a graph depicting the wavelength characteristic of the lights which are transmitted through the light guide in FIG. 13 and entered the illumination optical system.
Figure 18:
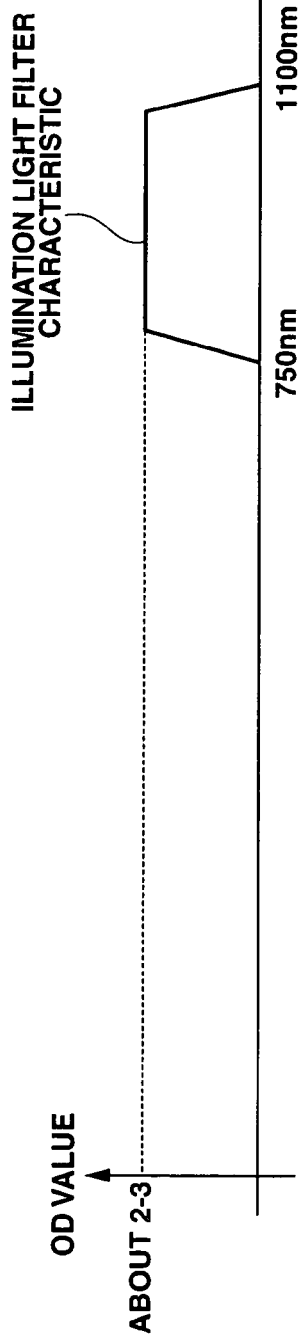
FIG. 18 is a graph depicting the filter characteristic of the illumination light filter in FIG. 13.
Figure 19:
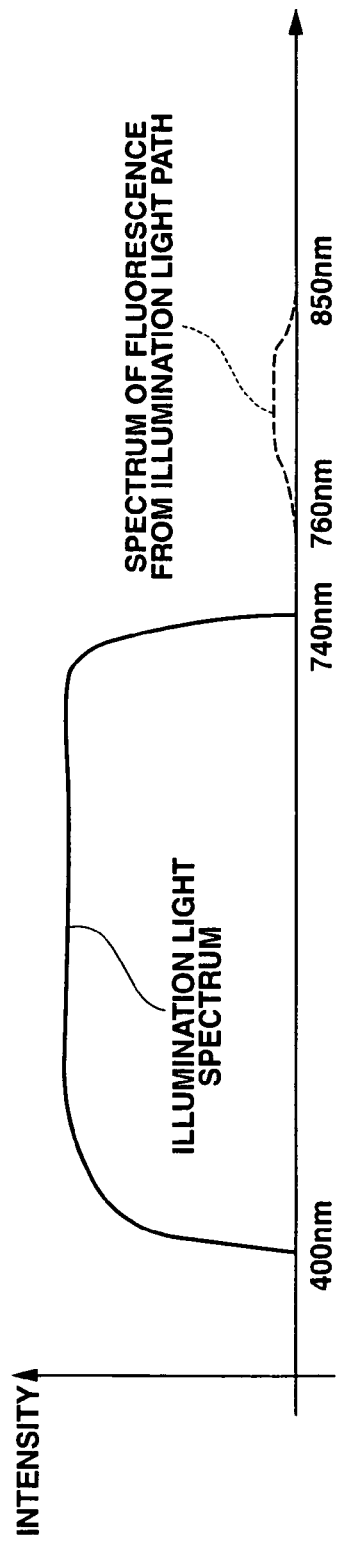
FIG. 19 is a graph depicting the wavelength characteristic of the lights which are transmitted through the illumination light filter in FIG. 13.
Figure 20:
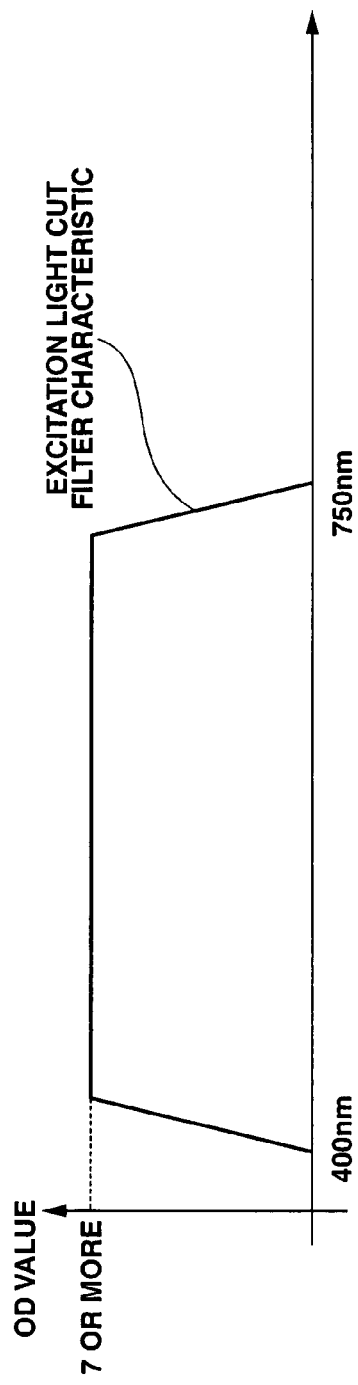
FIG. 20 is a graph depicting the filter characteristic of the excitation light cut filter in FIG. 13.
Figure 21:
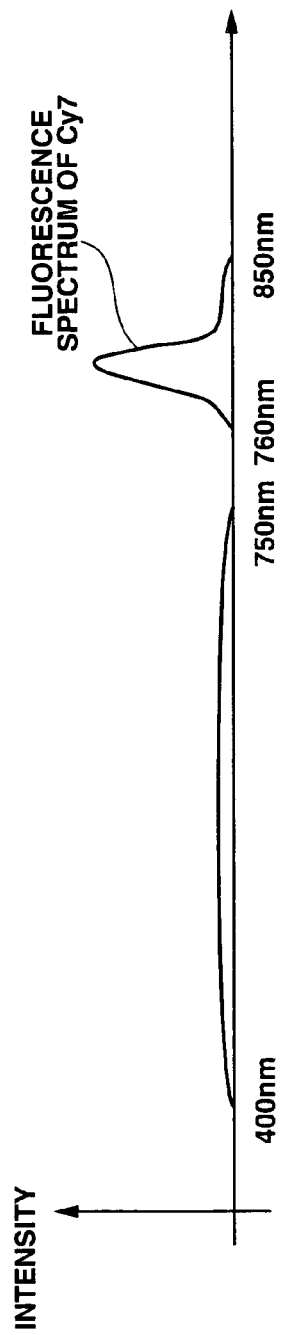
FIG. 21 is a graph depicting the wavelength characteristic of the lights which are transmitted through the excitation light cut filter in FIG. 13.
Figure 22:
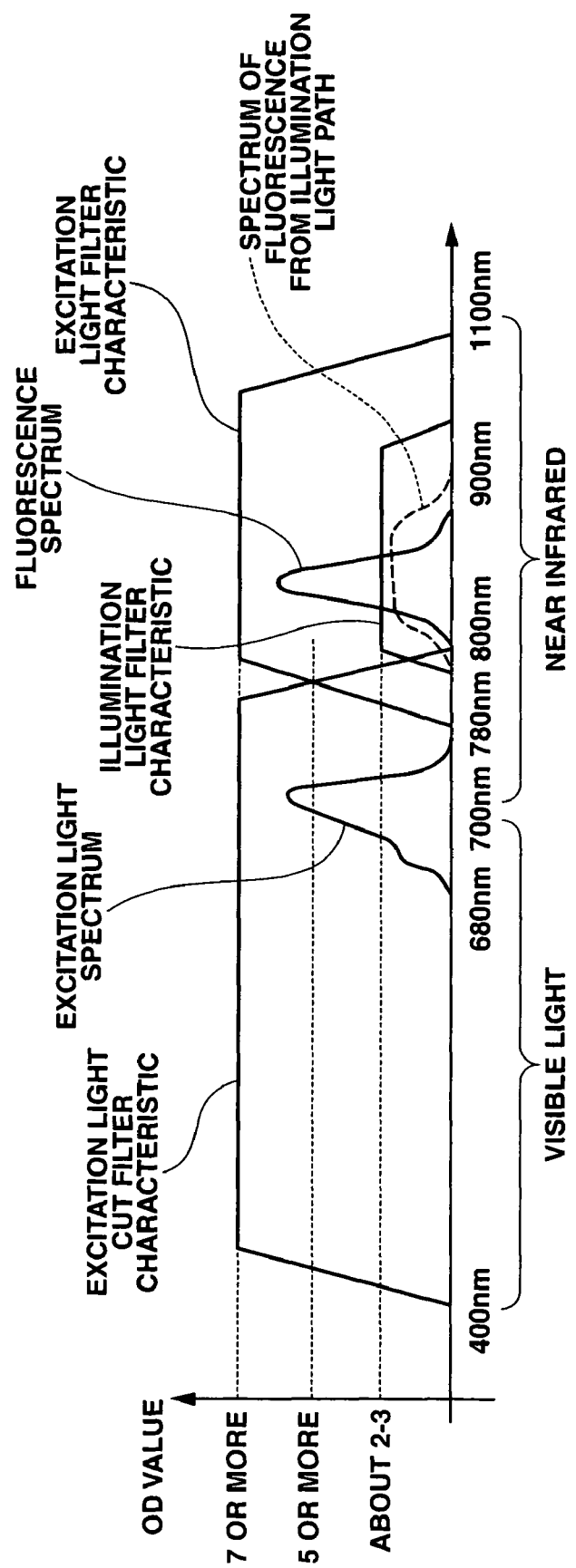
FIG. 22 is a graph depicting the wavelength characteristic when the graphs in FIG. 14 to FIG. 15 and FIG. 17 to FIG. 21 are combined into one.
Figure 23:
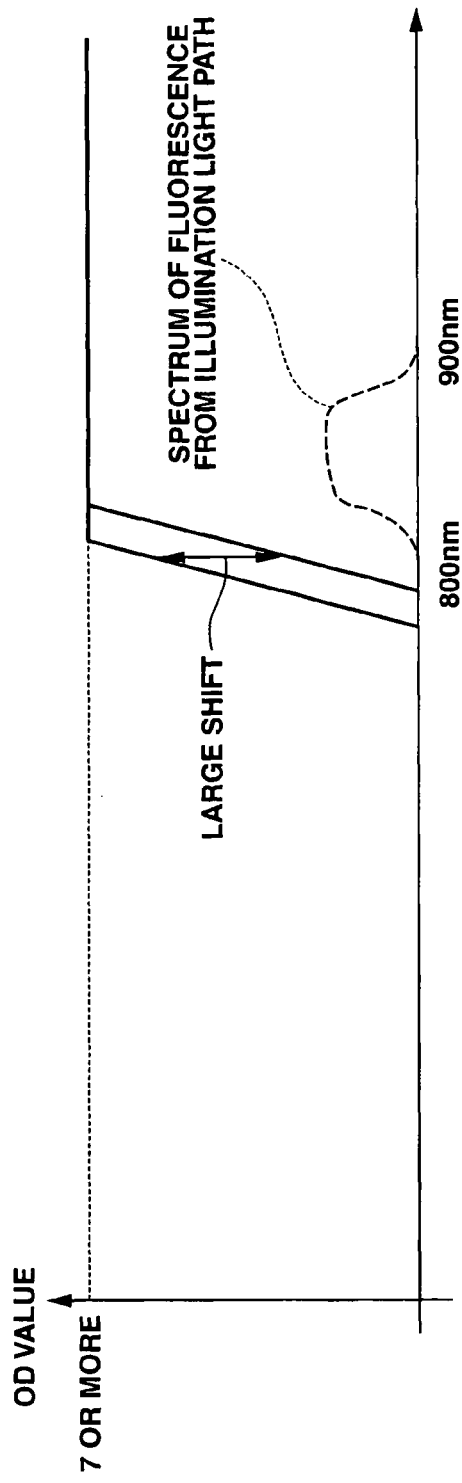
FIG. 23 is a graph depicting the filter characteristic of the illumination light filter of which OD value is high and edge is sharp.
Figure 24:
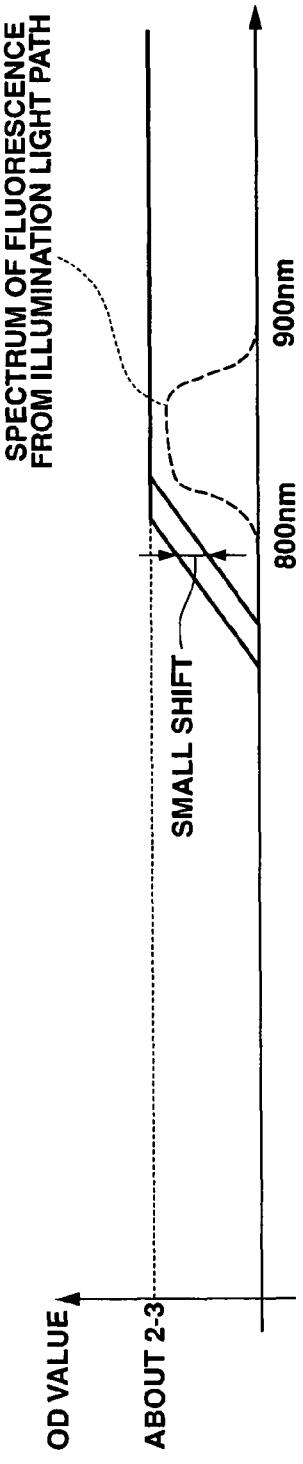
FIG. 24 is a graph depicting the filter characteristic of the illumination light filter of which OD value is low and edge is moderate.
Figure 25:
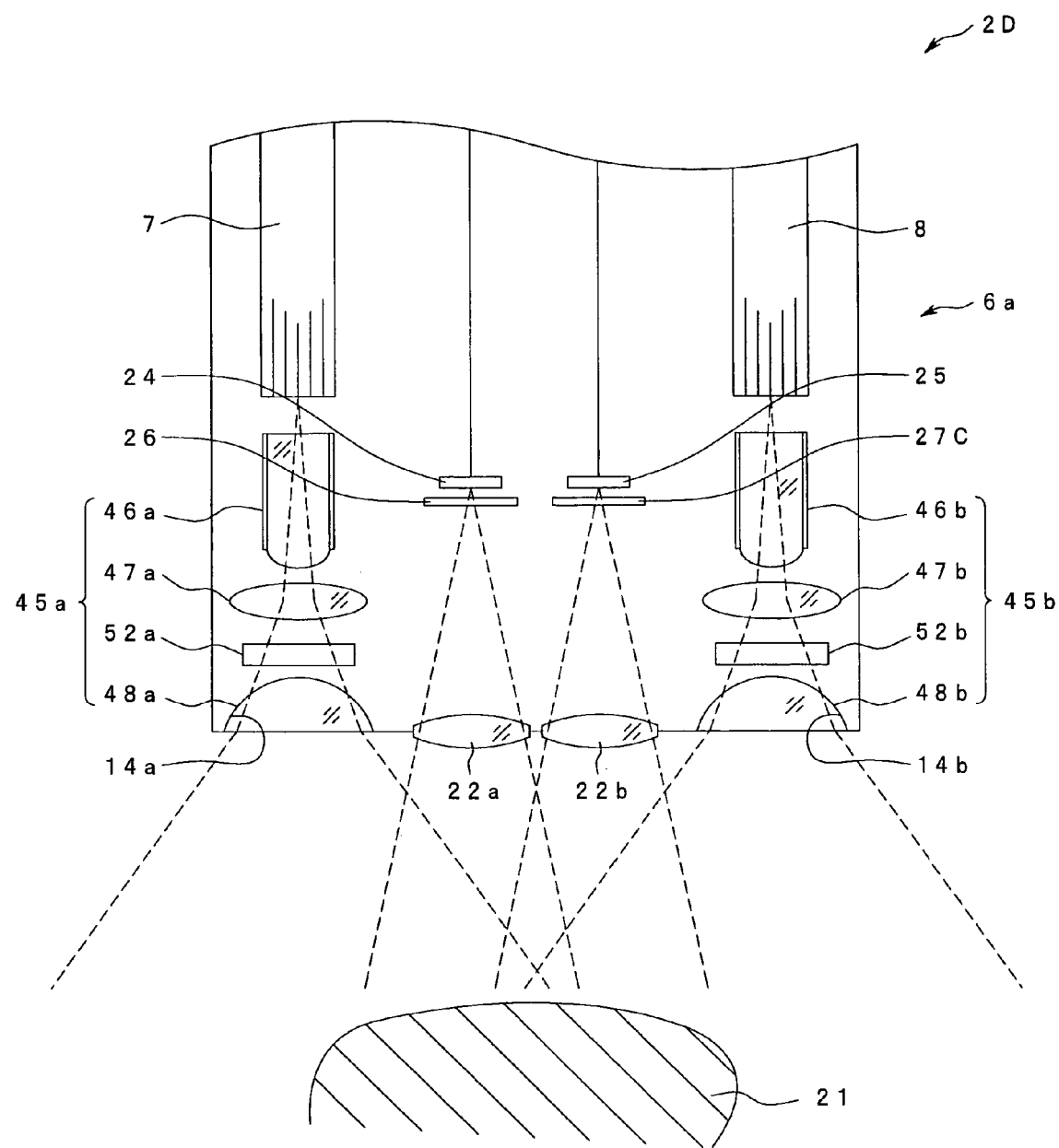
FIG. 25 is an enlarged view depicting a key section of a variant form of the insertion section in FIG. 13.
Figure 26:
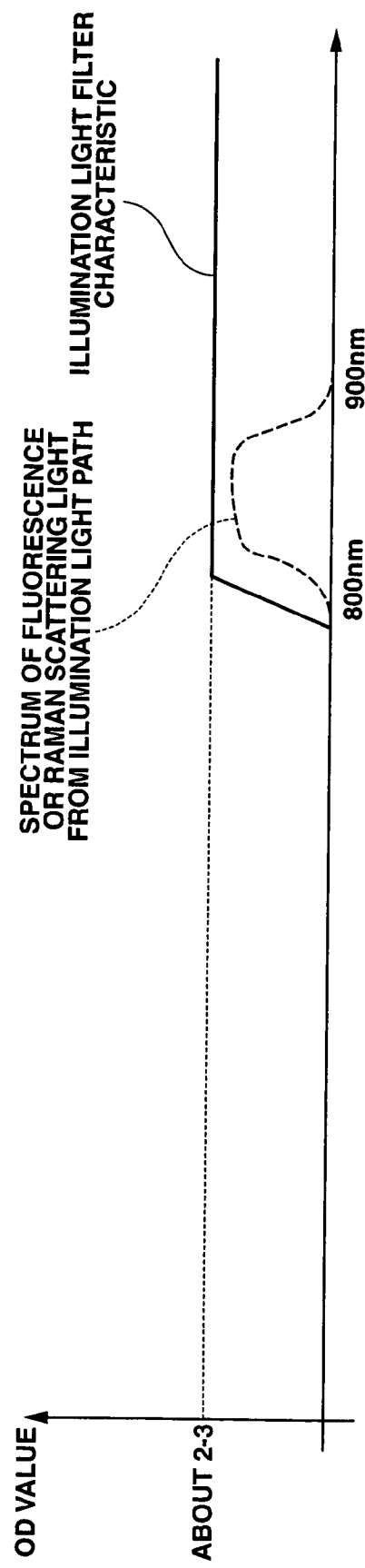
FIG. 26 is a graph depicting the filter characteristic of the short wavelength transmission filter (short wave path filter)

FIG. 13 to FIG. 26 are related to Embodiment 3 of the present invention, where FIG. 13 is a diagram depicting an entire configuration of the optical imaging device according to Embodiment 3, FIG. 14 is a graph depicting the filter characteristic of the excitation light filter in FIG. 13, FIG. 15 is a graph depicting the wavelength characteristic of the light which is transmitted through excitation light filter in FIG. 13, FIG. 16 is a graph depicting the filter characteristic of the RGB filter in FIG. 13, FIG. 17 is a graph depicting the wavelength characteristic of the light which is transmitted through the light guide in FIG. 13 and is incident on the illumination optical system, FIG. 18 is a graph depicting the filter characteristic of the illumination light filter in FIG. 13, FIG. 19 is a graph depicting the wavelength characteristic of the light which is transmitted through the illumination light filter in FIG. 13, FIG. 20 is a graph depicting the filter characteristic of the excitation light cut filter in FIG. 13, FIG. 21 is a graph depicting the wavelength characteristic of the light which is transmitted through the excitation light cut filter in FIG. 13, FIG. 22 is a graph depicting the wavelength characteristic when the graphs in FIG. 14 to FIG. 15 and FIG. 17 to FIG. 21 are combined into one, FIG. 23 is a graph depicting the filter characteristic of the illumination light filter of which OD value is high and edge is sharp, FIG. 24 is a graph depicting the filter characteristic of the illumination light filter of which OD value is low and edge is moderate, FIG. 25 is an enlarged view depicting a key section of a variant form of the insertion section in FIG. 13, and FIG. 26 is a graph depicting the filter characteristic of the short wavelength transmission filter (short wave path filter).

The above Embodiments 1 and 2 have a configuration where the illumination light filter section for decreasing fluorescence or Raman scattering light from the illumination light path is provided in the illumination optical system, but in Embodiment 3, a guided light filter section is also provided in the light source device, so as to combine with the illumination light filter section. The rest of the configuration is the same as Embodiments 1 and 2, therefore description thereof is omitted, and the same composing elements are described denoting the same reference symbols.

As FIG. 13 shows, the optical imaging device 1C of Embodiment 3 has a light source device 3C where an excitation light transmission filter (hereafter called excitation light filter) 50 and a visible light filter 51 are provided in a rotary disk 41C as a guided light filter section. The excitation light filter 50 has a filter characteristic to transmit the visible light and excitation light, and to shield near infrared. The filter characteristic will be described in detail later. In the present embodiment, infrared fluorescence observation described in Embodiment 1 is performed.

The visible light filter 51 has a filter characteristic to transmit visible light and shield other wavelengths. In the present embodiment, R, G and B filters 51a, 51b and 51c for transmitting lights with each wavelength band of R (red), G (green) and B (blue), are provided as the visible light filter 51, so that visible light is supplied field-sequentially. The filter characteristics of these R, G and B filters 51a to 51c will be described later.

Light from a white light source 11 provided in the light source device 3 is converted into roughly parallel beams by a collimator lens 12C, and then is incident on the rotary disk 41C. The light which has been incident on the rotary disk 41C is transmitted through the excitation light filter 50, R filter 51a, B filter 51c and G filter 51b according to the arranged sequence as the rotary disk 41C rotates, and sequentially is incident on the light incident ends 7a and 8a of the two light guides 7 and 8, which are inserted through the insertion section 6C of the endoscope 2C. A motor 42C rotates at a predetermined speed, such as one revolution per second, by drive signal from a rotation drive circuit 44C. And with the rotary disk 41C attached to the motor 42C being rotated, light which is incident on the rotary disk 41C sequentially is incident on the two light guides 7 and 8.

Specifically, in the state shown in FIG. 13 (that is, the state where the excitation light filter 50 is facing the light incident ends 7a and 8a of the light guides 7 and 8), for example, light which is incident on the rotary disk 41C is transmitted through the excitation filter 50, and is incident on the light incident ends 7a and 8a of the light guides 7 and 8. When the rotary disk 41C is rotated by ¼ turn from the state shown in FIG. 13, and the R filter 51a faces the light incident ends 7a and 8a of the light guides 7 and 8, the light which is incident on the rotary disk 41C is transmitted through the R filter 51a and is incident on the light incident ends 7a and 8a of the light guides 7 and 8. In the same way, in the state when the B filter 51c faces the light incident ends 7a and 8a, the light which is incident on the rotary disk 41C is transmitted through the B filter 51c, and in the state when the G filter 51b faces the light incident ends 7a and 8a, the light which is incident on the rotary disk 41C is transmitted through the G filter 51b, and is incident on the light incident ends 7a and 8a of the light guides 7 and 8 respectively.

In this way, the illumination light which is incident on the light guides 7 and 8 and emitted from the light emitting ends of the light guides 7 and 8 are spread and irradiated onto the subject 21 via each illumination optical system 45a and 45b facing the light emitting ends.

In the endoscope 2C, the illumination light filters 52a and 52b are provided in the illumination optical systems 45a and 45b respectively. These illumination light filters 52a and 52b are formed as interface filters or absorption filters, and have a function to shield fluorescence and Raman scattering lights from the illumination light path, which appear in the near infrared band (see FIG. 18).

In front of the image capturing face (light receiving face) of the image capturing section 25 for capturing the fluorescent image, an excitation light cut filter 27C is provided. The excitation light cut filter 27C has an optical characteristic to cut (shield) the excitation light which appears in the visible light band, and to transmit fluorescence from the subject (see FIG. 20). The rotary drive circuit 44C transmits synchronization signal synchronized with the rotation of the rotary disk 41C to the normal image processing circuit 31C and fluorescent image processing circuit 32C of the image generation circuit 4C. The normal image processing circuit 31C and fluorescent image processing circuit 32C perform processing to generate the normal image and fluorescent image respectively synchronizing with the received synchronization signal.

The normal image processing circuit 31C and fluorescent image processing circuit 32C incorporate an image capturing drive circuit, which is not illustrated, respectively. Each image capturing drive circuit applies the image capturing drive signal to the image capturing sections 24 and 25 respectively, performs photoelectric conversion for the lights received by the image capturing sections 24 and 25 respectively synchronizing with the synchronization signal, and outputs the acquired image capturing signal. In the above description, the rotary drive circuit 44C generates synchronization signal and sends it to the image generation device 4C, but the image generation device 4C may generate synchronization signal and send the generated synchronization signal to the rotary drive circuit 44C.

The image signal (video signal) of the normal image and image signal (video signal) of the fluorescent image, which are generated by the normal image processing circuit 31C and fluorescent image processing circuit 32C respectively, are output to the monitor 5C via the image synthesizing circuit 33C for synthesizing images, and on the display screen of the monitor 5C, the normal image 34C and fluorescent image 35C are displayed side by side, for example, as a synthesized image.

The monitor 5C in FIG. 13 shows an example of a display of images acquired in this status. Here the reference symbol 34C indicates the normal image by reflected light, and 35C indicates the fluorescent image by fluorescence emitted by the excitation light irradiated on the subject 21. The image generation device 4C, by the select operation of the display select switch 36C may switch among a state where the normal image 34C is displayed on the display screen of the monitor 5C without image synthesis processing by the image synthesizing circuit 33C, a state where the fluorescent image 35C is displayed on the display screen of the monitor 5C without image synthesis processing by the image synthesizing circuit 33C, and a state where the image synthesizing circuit 33C performs image synthesis processing, and a synthesized image of the normal image 34C and fluorescent image 35C is displayed on the display screen of the monitor 5C as one display image.

The function of Embodiment 3 will be described.

As FIG. 13 shows, the optical imaging device 1C is activated by operating the power supply switch, which is not illustrated, in a state where the endoscope 2C is connected to the light source device 3C. The operator inserts the insertion section 6C of the endoscope 2C into the body cavity of the patient, guides the distal portion 6a of the insertion section 6C to the target region, and performs fluorescence observation.

In other words, the operator administers fluorescent substance into the body of the patient in advance. The fluorescent substance accumulates into a lesioned part when a predetermined time elapsed after administration. In the present embodiment, infrared fluorescence observation is performed using fluorescence dye Cy 7 described in Embodiment 1.

The operator inserts the insertion section 6C of the endoscope 2C into the body cavity of the patient, and guides the distal portion 6a into the target region. Until the distal portion 6a of the insertion section 6C is guided to the target region, the operator displays only the normal image on the display screen of the monitor 5C by operating the display select switch 36C. When the distal portion 6a of the insertion section 6C reaches the target region, the operator starts infrared fluorescence observation.

At this time, the motor 42C rotates at a constant speed, and the rotary disk 41C also rotates according to the rotation of the motor 42C. The light from the white light source 11 is incident on the light incident ends 7a and 8a of the light guides 7 and 8 sequentially via the excitation light filter 50, R filter 51a, G filter 51b and B filter 51c according to the rotation of the rotary disc 41C. The excitation light filter 50 has the filter characteristic shown in FIG. 14, for example. In the graph in FIG. 14, the abscissa indicates the wavelength and the ordinate indicates the OD value.

In other words, the excitation light filter 50 transmits the wavelength band 400 to 750 nm including visible light and 680 to 740 nm of excitation light of the fluorescence dye Cy 7, and shields the wavelength band 750 to 1100 nm of near infrared with an OD value of 7 or more. Therefore the light that is transmitted through the excitation light filter 50 and is incident on the light incident ends 7a and 8a of the light guides 7 and 8 is only the wavelength band 400 to 750 nm of illumination light, including the excitation light 680 to 740 nm of the fluorescence dye Cy 7, as shown in FIG. 15. In the graph in FIG. 15, the abscissa indicates the wavelength and the ordinate indicates the intensity.

The R, G and B filters 51a to 51c have the filter characteristics shown in FIG. 16, for example. In the graph in FIG. 16, the abscissa indicates the wavelength and the ordinate indicates the transmittance. The R, G and B filters 51a to 51c transmit the lights with wavelength bands 600 to 750 nm, 500 to 570 nm and 380 to 500 nm respectively, and shields other lights. The excitation light 680 to 740 nm of the fluorescence dye Cy 7 is included in the lights that are transmitted through the R filter 51a. Therefore the lights which are transmitted through the R, G and B filters 51a to 51c and are incident on the light incident ends 7a and 8a of the light guides 7 and 8 are only lights with 600 to 750 nm, 500 to 570 nm, and 380 to 500 nm respectively.

Hereafter the light transmitted through the excitation light filter 50 will be described as an example.

Light which entered the light guides 7 and 8 from the excitation light filter 50 is transmitted by these light guides 7 and 8, is emitted from the light emitting ends, and is incident on the illumination optical systems 45a and 45b.

The light which is incident on the illumination optical system 45a and 45b includes fluorescence from the illumination light path, as shown in FIG. 17, for example. In the graph in FIG. 17, the abscissa indicates the wavelength and the ordinate indicate the intensity. The fluorescence from the illumination light path exists in around the fluorescent wavelength band 760 to 850 nm of fluorescence dye Cy 7. The light which is incident on the illumination optical systems 45a and 45b is irradiated onto the subject 21 via the illumination light filters 52a and 52b.

The illumination filters 52a and 52b have the filter characteristics shown in FIG. 18, for example. In the graph in FIG. 18, the abscissa indicates the wavelength and the ordinate indicates the OD value. The illumination light filters 52a and 52b transmit wavelength 400 to 750 nm, including the visible light and the of excitation light 680 to 740 nm of fluorescence dye Cy 7, and shield the wavelength 750 to 1100 nm of near infrared, including the above mentioned fluorescence from the illumination light path with an OD value of about 2 to 3.

The reason illumination light filters 52a and 52b shield wavelength 750 to 1100 nm of near infrared with an OD value of about 2 to 3 is because the excitation light filter 50 of the light source device 3C shields near infrared, which is roughly in the same wavelength band, with an OD value of 7 or more.

Therefore in the lights which transmitted through the illumination light filters 52a and 52b and are irradiated onto the subject 21, the fluorescence from the illumination light path, which exists in fluorescent wavelength band 760 to 850 nm of the fluorescence dye Cy 7, is decreased, as shown in FIG. 19. In the graph in FIG. 19, the abscissa indicates the wavelength and the ordinate indicates the intensity. Because of this, light in which wavelength 750 to 1100 nm of near infrared, including fluorescence from the illumination light path, is decreased, is irradiated onto the subject 21.

The return lights from the subject 21 are incident on the objective lens 22, and are split into two by a beam splitter 23. Out of the lights split by the beam splitter 23, the reflected lights is formed an image at the image capturing section 24, and the transmitted lights is formed into an image at the image capturing section 25 via the excitation light cut filter 27C. The excitation light cut filter 27C has the filter characteristic shown in FIG. 20. In the graph in FIG. 20, the abscissa indicates the wavelength and the ordinate indicates the OD value.

As FIG. 20 shows, the excitation light cut filter 27C shields the wavelength band 400 to 750 nm of visible light with an OD value of 7 or more, and transmits lights in other wavelength bands. Therefore in the lights transmitted through the excitation light cut filter 27C, the wavelength band 400 to 750 nm of visible light is decreased, and the wavelength band 760 to 850 nm of fluorescence generated by the fluorescence dye Cy 7 becomes dominant, as FIG. 21 shows.

The wavelength characteristic of the optical imaging device 1C of the present embodiment is shown in FIG. 22, which is a composite of the graphs in FIG. 14 to FIG. 15 and FIG. 17 to FIG. 21. In the graph in FIG. 22, the abscissa indicates the wavelength and the ordinate indicates the OD value.

As FIG. 22 shows, the excitation light filter 50 transmits the wavelength band 400 to 750 nm, including visible light and excitation light 680 to 740 nm of fluorescence dye Cy 7, and shields the wavelength band 750 to 1100 nm of near infrared with an OD value of 7 or more. The illumination light filters 52a and 52b transmit the wavelength band 400 to 750 nm, including the visible light and excitation light 680 to 740 nm of fluorescence dye Cy 7, and shields the wavelength band 750 to 1100 nm of near infrared including the fluorescence from the illumination light path with an OD value of about 2 to 3.

The excitation light cut filter 27C transmits only the wavelength band 760 to 850 nm of fluorescence generated by fluorescence dye Cy 7, since the wavelength band 400 to 750 nm of visible light are shielded with an OD value of 7 or more. The intersections of the light shielding band of the illumination light filters 52a and 52b and the light shielding band of the excitation light cut filter 27C have an OD value of 5 or more. The light transmitted through the excitation light cut filter 27C is received by the image capturing section 25 and are photoelectrically converted. The light reflected by the beam splitter 23 is received by the image capturing section 24 for each R, G and B, and are photoelectrically converted.

The information on the light received by the image capturing section 24 is output to the monitor 5C as the normal image via the normal image processing circuit 31C and the image synthesizing circuit 33C. The information on the light received by the image capturing section 25 is output to the monitor 5C as the fluorescent image via the fluorescent image processing circuit 32C and image synthesizing circuit 33C. In this way, on the display screen of the monitor 5C, the normal image 34C and fluorescent image 35C are displayed side by side.

As a result, the optical imaging device 1C of the present embodiment can decrease fluorescence from the illumination light path in the near infrared band, and both the normal image 34C and fluorescent image 35C can be acquired, just like the case of Embodiment 1. The optical imaging device 1C can also decrease Raman scattering light from the illumination light path in the near infrared band in the same way.

Because of this, the optical imaging device 1C of Embodiment 3 can be used for both fluorescence observation and normal endoscopic observation, and can decrease the fluorescence and Raman scattering lights from the illumination light path. Generally a filter of which the OD value is about 3 is sufficient to shield fluorescence and Raman scattering lights from the illumination light path, but by itself it is insufficient to shield light in the fluorescent wavelength bands included in the excitation light source. This is because, as described above, it is highly possible to satisfy regular reflection conditions in two-dimensional observation since the field angle of the objective lens 22 is wide, and that light after regular reflection has high intensity, so a filter of which the OD value is about 7 must be used to shield light in the fluorescent wavelength band included in the excitation light source. Also the sensitivity of CCD drops relatively in the near infrared band (750 to 1100 nm) compared with the visible light band, so the OD value must be set high to prevent a drop in the S/N ratio. In the case of the optical imaging device 1C of the present embodiment, however, the excitation light filter 50 and visible light filter 51 are provided in the light source device 3C as the guided light filter section, and light in the fluorescence wavelength band included in the excitation light source is shielded with an OD value of 7 or more by the excitation light filter 50, so it is unnecessary to set a high OD value for the illumination light filters 52a and 52b provided in the distal portion 6a of the insertion section 6C, and lights other than fluorescence or Raman scattering lights from the illumination light path, such as lights in the fluorescence wavelength band included in the excitation light source, need not be shielded. Therefore the OD value of the illumination light filter in the present embodiment can be about 3, which is sufficient in most cases.

On the other hands, in order to manufacture a filter with a high OD value, a filter must be made up of many more layers. Therefore the required performance may not be implemented only by one substrate, and a plurality of substrates may be required. As the number of layers formed on the substrate increases, the film stress which the substrate receives from the films increases, so even if one substrate could implement the required performance, a substrate having sufficient thickness to withstand the film stress must be used to prevent damage to the substrate. According to the present embodiment, the OD value of the illumination light filter is about 3, which is sufficient, so the number of film layers can be decreased, and there is no need to use a plurality of substrates, which makes filter fabrication easier, and can make the substrate very thin. As a result, the entire endoscope can be smaller. This configuration is particularly effective if this is applied to an endoscope having an extremely small diameter, such as a bronchus endoscope, pancreas/gall bladder endoscope, and an endoscope used for such small animals as a mouse.

Also in the case of the optical imaging device 1C of Embodiment 3, where an visible light image is acquired for R, G and B field-sequentially, a normal image at high resolution can be acquired (in other words, a color signal for each R, G and B can be acquired for each pixel position, so interpolation processing, required for a single image capturing element, is not required). Therefore the optical imaging device 1C of Embodiment 3 is combined with visible light filters 51 (R, G, B filters 51a to 51c) in the light source device 3C, so that it is applied to the field-sequential system.

The illumination light filters 52a and 52b are placed in the illumination optical systems 45a and 45b. Into the illumination light filters 52a and 52b, light from the light emitting ends of the light guides 7 and 8 could be incident on diagonally via the relay lenses 47a and 47b of the illumination optical systems 45a and 45b. If the light is incident on diagonally, the wavelength characteristic of the optical filter shifts. Therefore as FIG. 23 shows, if an illumination light filter of which the OD value is high and of which edge is sharp is used, the light which diagonally is incident on the filter from the lens edge of the relay lenses 47a and 47b have a major influence on the wavelength characteristic of the illumination light filter. This situation is the same for the case of the above mentioned optical thin film, where the illumination light filter is formed on the lens.

In the present embodiment, the excitation light filter 50 and visible light filter 51, as the guided light filter sections having a sharp edge with an OD value of 7 or more, are provided inside the light source device 3C, and at the distal portion 6a of the insertion section 6C, the illumination light filters 52a and 52b having a moderate edge with an OD value of about 2 to 3, as shown in FIG. 24, are placed. Therefore, by this configuration, the influence of the shift of the filter characteristic caused by diagonal incidence can be decreased in the present embodiment. Even if the filter characteristic is considerably shifted, depending on the incident direction of the light, the capability of shielding the fluorescent wavelength band included in the light source does not drop, since the guided light filter section is provided inside the light source device 3C, so a major drop in the S/N ratio can be prevented.

The endoscope of the optical imaging device 1C may be configured without using a beam splitter 23, as shown in FIG. 25.

As FIG. 25 shows, the endoscope 2D has two objective lenses 22a and 22b, and has the above mentioned image capturing sections 24 and 25 respectively at the image forming positions of these objective lenses 22a and 22b. The visible light filter 26 is placed in front of the image capturing face (light receiving face) of the image capturing section 24. The endoscope 2D having this configuration can exhibit an effect similar to the above mentioned Embodiment 3, and the diameter thereof can be further decreased since the beam splitter 23 is not used.

The optical imaging device 1C has a guided light filter section, so it is sufficient that the illumination light filters 52a and 52b, placed at the distal portion 6a of the insertion section 6C, can shield only the fluorescence or Raman scattering light from the illumination light path. Therefore in the optical imaging device 1C, the illumination light filters 52a and 52b may be substituted with short wavelength transmission filters (short wave pass filters), as shown in FIG. 26.

As FIG. 26 shows, the short wavelength transmission filter (short wave pass filter) has a filter characteristic to pass a wavelength band of less than 750 nm, where the fluorescence from the illumination light pass is not included. Therefore if the short wavelength transmission filter (short wave pass filter) is used, it is unnecessary to consider the cut off frequency at the 750 nm or longer wavelength side, and compared with the case of providing a band pass filter, design is simplified and the number of layers is decreased, which makes fabrication easier.

In the present embodiment, the OD value of the illumination light filter is about 2 to 3, but the present invention is not limited to this. In other words, if an illumination light filter with a higher OD value is used, a fluorescence dye observation with a weaker intensity can be performed. The guided light filter is provided inside the light source device, so there is not space restriction, unlike the case of the illumination light filter provided at the distal end of the endoscope, and it is also possible to provide a filter with a higher OD value using a plurality of substrates (e.g. OD value 8 to 9, or more). According to this configuration, a drop in the S/N ratio can be suppressed even if a fluorescence with a weaker intensity is observed.

Embodiment 4

Figure 27:
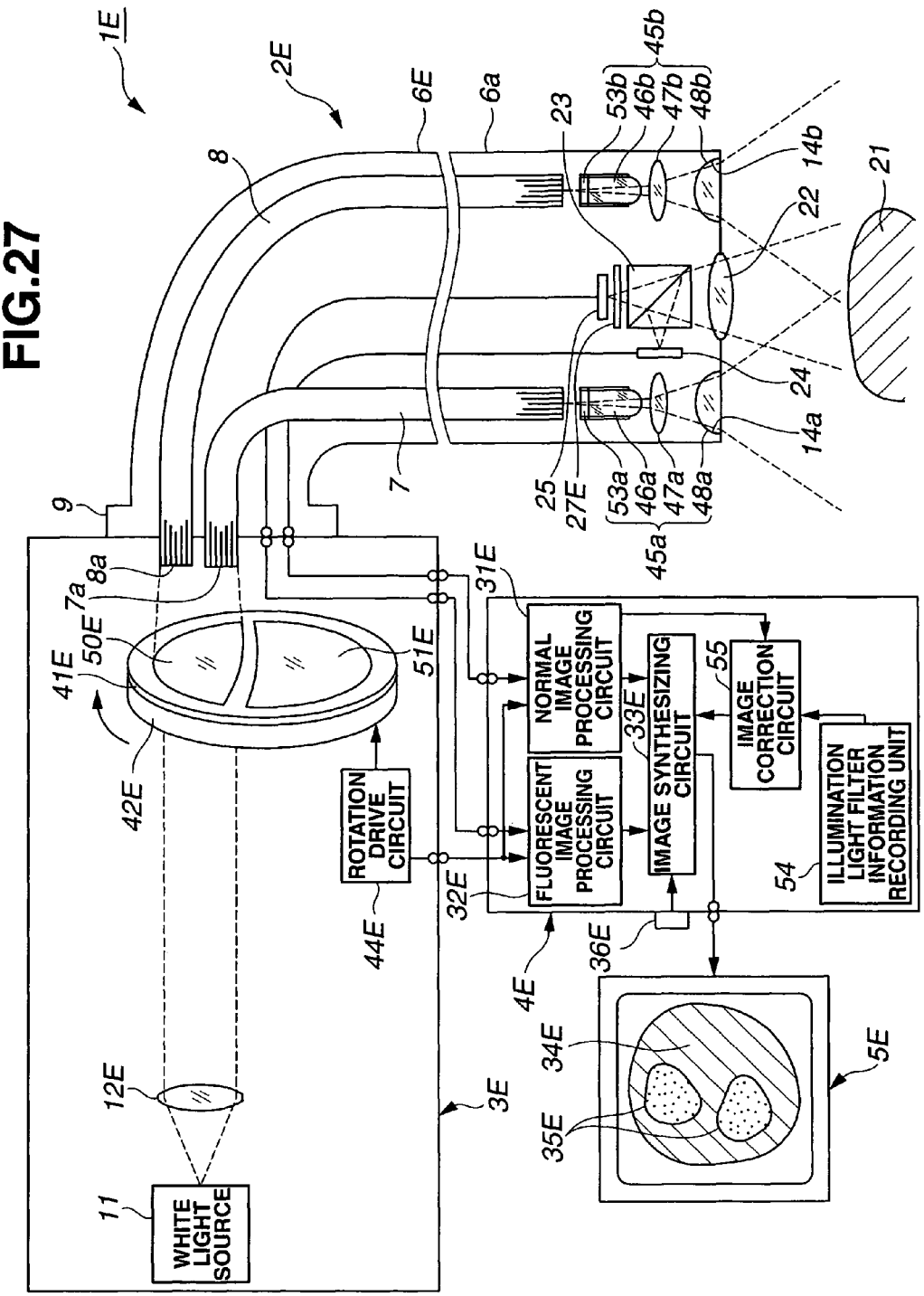
FIG. 27 is a diagram depicting an entire configuration of the optical imaging device according to Embodiment 4.
Figure 30:
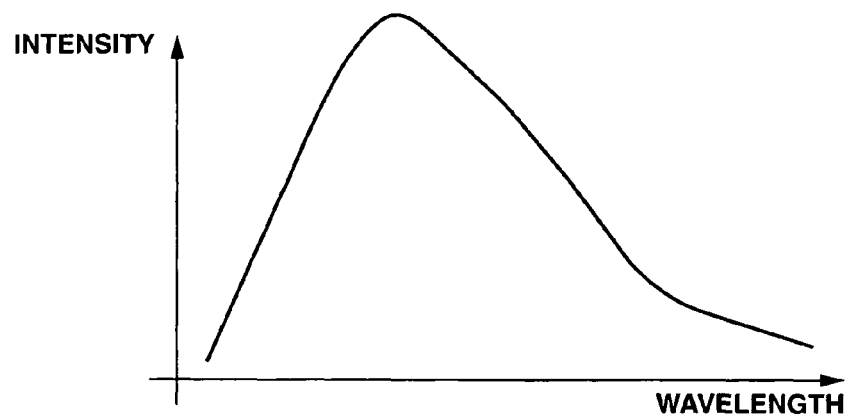
FIG. 30 is a graph depicting the original spectrum of the reflected visible lights from the subject.
Figure 31:
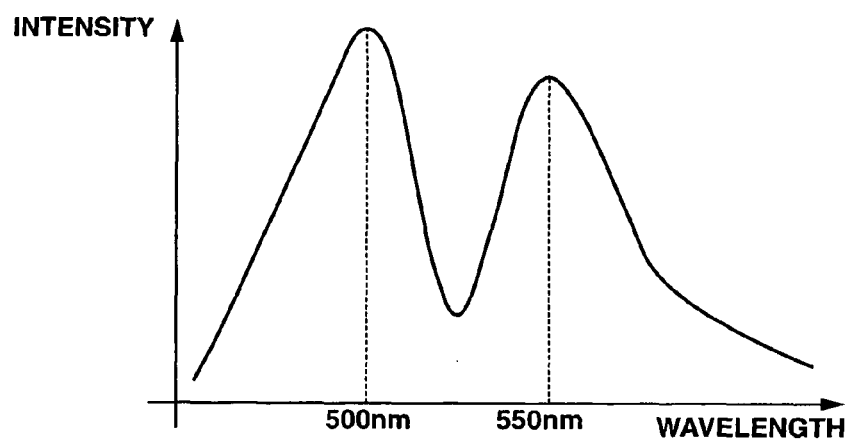
FIG. 31 is a graph depicting the spectrum of the reflected visible lights from the subject which the image capturing section receives based on the graph in FIG. 30.
Figure 32:
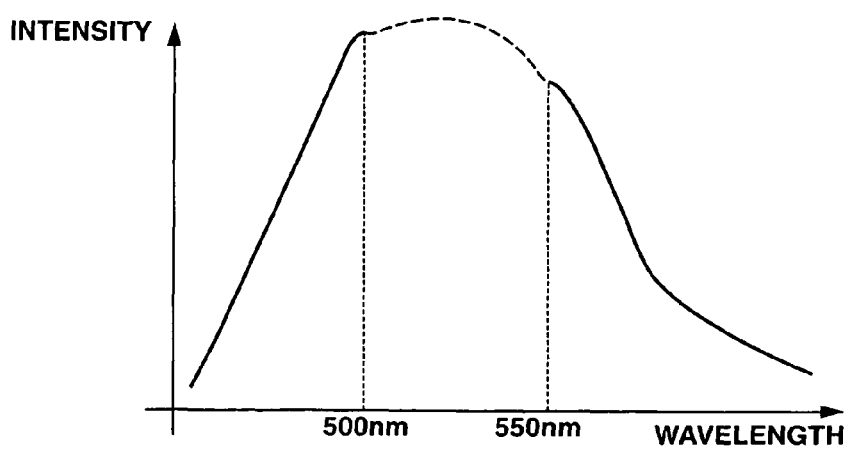
FIG. 32 is a graph depicting the spectrum of the reflected visible lights when correction processing for amplifying the attenuated spectrum in the wavelength band 500 to 550 nm is performed as to the graph in FIG. 31.
Figure 33:
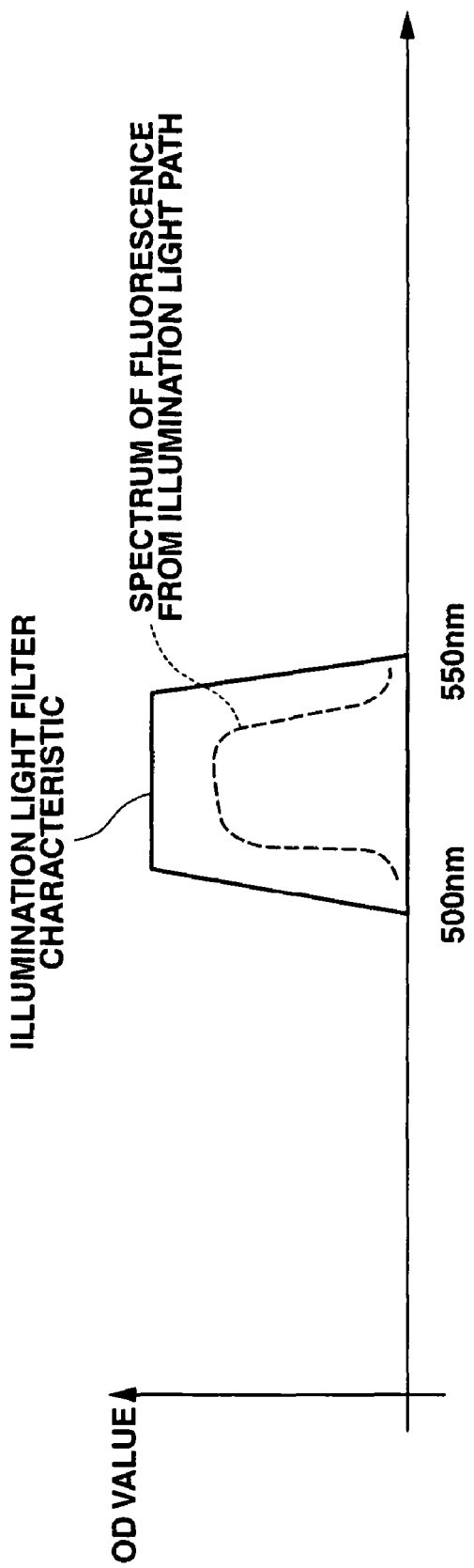
FIG. 33 is a graph depicting the filter characteristic of the illumination light filter, where the wavelength band around 500 to 550 nm is shielded with about OD value 2 to 3, in the wavelength band 500 to 570 nm of a G (green) light.
Figure 34:
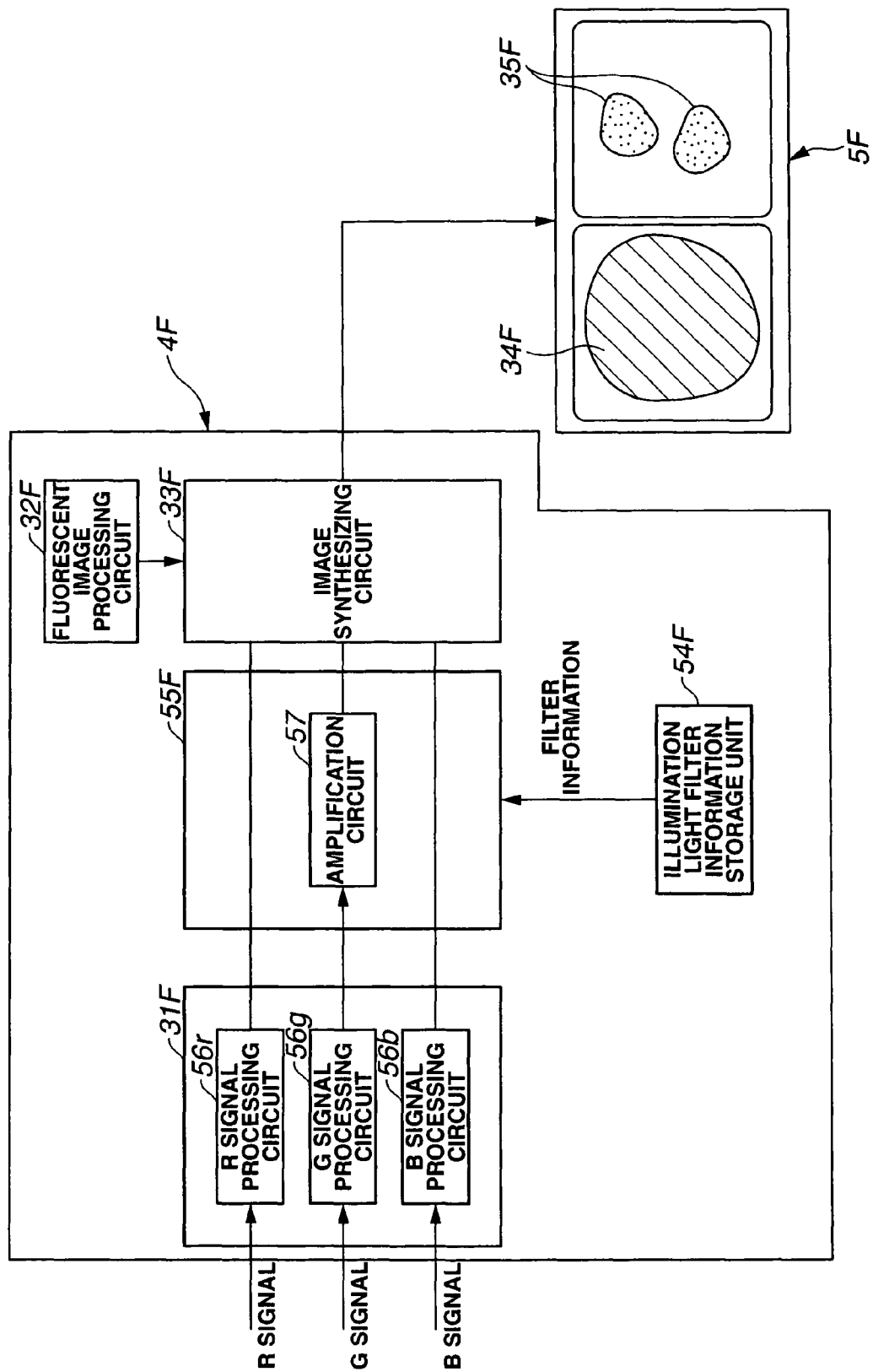
FIG. 34 is a block diagram depicting the configuration of the image generation device having the image correction circuit for amplifying only the G signal.
Figure 35:
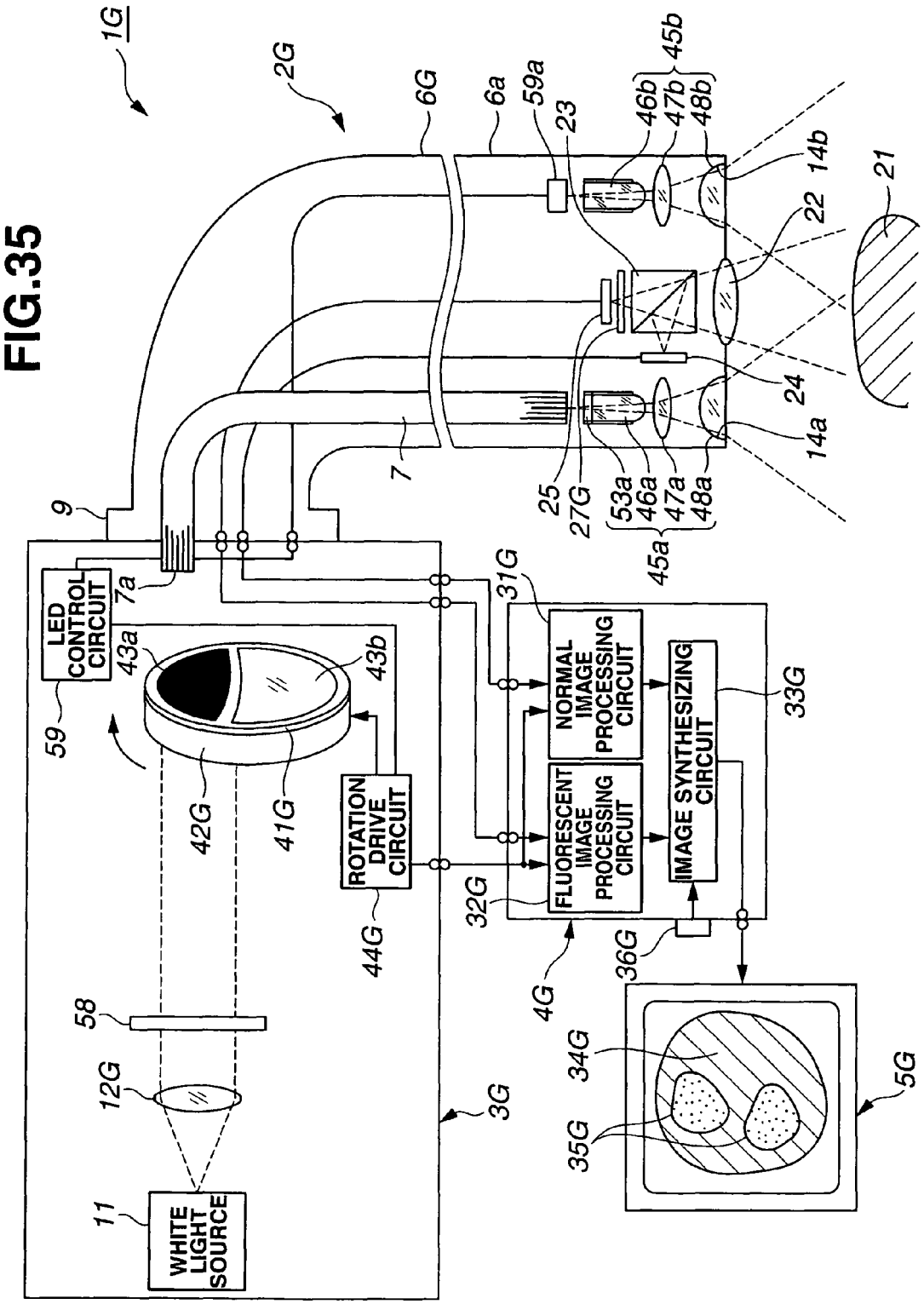
FIG. 35 is a diagram depicting an entire configuration of the optical imaging device according to a variant form of FIG. 27.

FIG. 27 to FIG. 35 are related to Embodiment 4 of the present invention, where FIG. 27 is a diagram depicting an entire configuration of the optical imaging device according to Embodiment 4, FIG. 28 is a graph depicting the filter characteristic of the excitation light filter and excitation light cut filter in FIG. 27, FIG. 29 is a graph depicting the filter characteristic of the illumination light filter in FIG. 27, FIG. 30 is a graph depicting the original spectrum of the reflected visible light from the subject, FIG. 31 is a graph depicting the reflected visible light from the subject which the image capturing section receives based on the graph in FIG. 30, FIG. 32 is a graph depicting the spectrum of the reflected visible light when correction processing for amplifying the attenuated spectrum in the wavelength band 500 to 550 nm is performed as to the graph in FIG. 31, FIG. 33 is a graph depicting the filter characteristic of the illumination light filter, where the wavelength band around 500 to 550 nm is shielded with an OD value of about 2 to 3 in the wavelength band 500 to 570 nm which is a G (green) wavelength band, FIG. 34 is a block diagram depicting the configuration of the image generation device having the image correction circuit for amplifying only the G signal, and FIG. 35 is a diagram depicting an entire configuration of the optical imaging device according to a variant form of FIG. 27.

In Embodiment 3, the guided light filter is provided in the light source device combining with the illumination light filter, and infrared fluorescence observation is performed, but in Embodiment 4, the guided light filter is provided in the light source device combining with the illumination light filter, and visible light fluorescence observation is performed. The rest of the configuration is the same as Embodiment 3, therefore description thereof is omitted, and the same components are described denoting the same reference symbols.

As FIG. 27 shows, the optical imaging device 1E of Embodiment 4 has a light source device 3E where an excitation light filter 50E and a visible light filter 51E are provided in a rotary disk 41E as a guided light filter section. The excitation light filter 50E has a filter characteristic to transmit visible light other than the fluorescent wavelength band and to shield the other wavelength bands (see FIG. 28). The visible light filter 51E, on the other hand, is a white light filter which transmits all visible light (e.g. 400 to 700 nm) and shields other wavelength bands.

Light from a white light source 11, which is incident on the rotary disk 41E, is incident on the rotary disk 41E via the collimator lens 12E. The light which is incident on the rotary disk 41E is transmitted through the excitation light filter 50E and visible light filter 51E according to the rotation of the rotary disk 41E, and is incident on the light incident ends 7a and 8a of the two light guides 7 and 8, which are inserted through the insertion section 6E of the endoscope 2E.

A motor 42E rotates at a predetermined speed, such as one revolution per second, by the drive signal from a rotary drive circuit 44E. The light which is incident on the rotary disk 41E provided in this motor 42E by the rotary disk 41E rotating according to the rotation of the motor 42E is incident on the two light guides 7 and 8.

Specifically, in the state shown in FIG. 27, the light from the white light source 11 that has been incident on the rotary disk 41E is transmitted through the excitation light filter 50E and is incident on both of the light guides 7 and 8. When the rotary disk 41E is rotated a half turn from the state shown in FIG. 27, the light which has been incident on the rotary disk 41E is transmitted through the visible light filter 51E and is incident on both of the light guides 7 and 8. The illumination light, which is incident on the light guides 7 and 8 and is emitted from the light emitting ends of the light guides 7 and 8, is spread and irradiated onto the subject 21 via each illumination optical systems 45a and 45b facing the light emitting ends.

In the endoscope 2E, the illumination light filters 53a and 53b are placed in the illumination optical systems 45a and 45b respectively. These illumination light filters 53a and 53b are constructed as optical thin films formed on the light entering end faces of the rod lenses 46a and 46b respectively. These illumination light filters 53a and 53b have an optical characteristic to shield fluorescence and Raman scattering lights from the illumination light path, which appear in the visible light band (see FIG. 29).

In front of the image capturing face (light receiving face) of the image capturing section 25 for capturing the fluorescent image, the excitation light cut filter 27E is provided. This excitation light cut filter 27E has an optical characteristic to transmit fluorescence from the subject, and to cut (shield) the other wavelength bands (see FIG. 28). The rotary drive circuit 44E transmits synchronization signal synchronizing with the rotation of the rotary disk 41E to the normal image processing circuit 31E and fluorescent image processing circuit 32E of the image generation device 4E. The normal image processing circuit 31E and fluorescent image processing circuit 32E perform processing to generate normal images and fluorescent images respectively, synchronizing with the received synchronization signal.

The normal image processing circuit 31E and fluorescent image processing circuit 32E incorporate an image capturing drive circuit, which is not illustrated, respectively. Each image capturing drive circuit applies the image capturing drive signal to the image capturing sections 24 and 25 respectively, synchronizing with the synchronization signal, performs photoelectric conversion for the lights received by the image capturing sections 24 and 25 respectively, and outputs the acquired image capturing signal. In the above description, the rotary drive circuit 44E generates the synchronization signal and sends them to the image generation device 4E, but the image generation device 4E may generate the synchronization signal and send the generated synchronization signal to the rotary drive circuit 44E.

The image signal (video signal) of the normal image and image signal (video signal) of the fluorescent image, which are generated by the normal image processing circuit 31E and fluorescent image processing circuit 32E, are output to the monitor 5E via the image synthesizing circuit 33E for composing the images, and on the display screen of the monitor 5E, the normal image and fluorescent image are displayed in a composite state, for example.

The monitor 5E in FIG. 27 shows an example of the display of images acquired in this status. Here the reference symbol 34E indicates the normal image by the reflected light, and 35E indicates the fluorescent image by the fluorescence emitted by the excitation light irradiated on the subject 21. The image generation device 4E, by the select operation of the display select switch 36E may switch among a state where the normal image 34E is displayed on the display screen of the monitor 5E without image synthesis processing by the image synthesizing circuit 33E, a state where the fluorescent image 35E is displayed on the display screen of the monitor 5E without image synthesis processing by the image synthesizing circuit 33E, and the state where the image synthesizing circuit 33E performs image combination processing and the normal image 34E and fluorescent image 35E are displayed on the display screen of the monitor 5E side by side.

The image generation device 4E comprises an illumination light filter information recording section 54 and an image correction circuit 55. The illumination light filter information recording section 54 records filter characteristic information according to the type of illumination light filter provided in the endoscope 2C.

The image correction circuit 55 performs correction processing on the image signal (video signal) of the normal image generated by the normal image processing circuit 31E based on the information recorded in the illumination light filter information recording section 54, and outputs it to the image synthesizing circuit 33E. This correction processing will be described later in detail.

The function of Embodiment 4 will be described.

As FIG. 27 shows, the optical imaging device 1E is activated by operating the power supply switch, which is not illustrated, in a state where the endoscope 2E is connected to the light source device 3E. The operator inserts the insertion section 6E of the endoscope 2E into the body cavity, guides the distal portion 6a of the insertion section 6E into a target region, and performs fluorescence observation. In the present embodiment, it is assumed that the visible light fluorescence observation is performed using collagen as the endogenous fluorescent substance.

The operator inserts the insertion section 6E of the endoscope 2E into the body cavity of the patient, and guides the distal portion 6a into the target region. Until the distal portion 6a of the insertion section 6E is guided into the target region, the operator displays only the normal image on the display screen of the monitor 5E by operating the display select switch 36E. When the distal portion 6a of the insertion section 6E reaches the target region, the operator starts the visible light fluorescence observation.

At this time, the motor 42E rotates at a constant speed, and the rotary disk 41E also rotates according to the rotation of the motor 42E. The light from the white light source 11 is incident on the light incident ends 7a and 8a of the light guides 7 and 8 via the excitation light filter 50E and visible light filter 51E according to the rotation of the rotary disk 41E.

The excitation light filter 50E has the filter characteristic shown in FIG. 28, for example. In the graph in FIG. 28, the abscissa indicates the wavelength and the ordinate indicates the OD value. The excitation light filter 50E shields the wavelength band 500 to 550 nm including 520 nm of fluorescence of collagen and wavelength band 700 to 1100 nm of near infrared with an OD value of 7 or more, and transmits the visible light band 400 to 480 nm and 550 to 700 nm, including 450 nm of the excitation light of collagen. Therefore the light that is transmitted through the excitation light filter 50E and is incident on the light incident ends 7a and 8a of the light guides 7 and 8 are only the wavelength band 400 to 480 nm and 550 to 700 nm of the visible light band, including 450 nm of the excitation light of collagen.

The visible light filter 51E, which is not illustrated, transmits the visible light band 400 to 700 nm, and shields the other wavelength bands. Therefore the light that is transmitted through the visible light filter 51E and is incident on the light incident ends 7a and 8a of the light guides 7 and 8 are only visible lights (400 to 700 nm). Hereafter the lights transmitted through the excitation light filter 50E will be described as an example.

The light which is incident on the light guides 7 and 8 from the excitation filter 50E is transmitted by the light guides 7 and 8, and are emitted from the light emitting ends of the light guides 7 and 8, and is incident on the illumination optical systems 45a and 45b. At the same time, the light which has been incident on the illumination optical systems 45a and 45b include the fluorescence from the illumination light path. The light which is incident on the illumination optical systems 45a and 45b is irradiated onto the subject 21 via the illumination light filters 53a and 53b.

The illumination light filters 53a and 53b have the filter characteristics shown in FIG. 29, for example. In the graph in FIG. 29, the abscissa indicates the wavelength and the ordinate indicates the OD value. The illumination light filters 53a and 53b shield wavelength band 500 to 550 nm, including 520 nm of fluorescence of collagen with an OD value of 2 to 3, and transmit the visible light band 400 to 480 nm and 550 to 700 nm, including 450 nm of the excitation light of collagen.

The wavelength bands to be shielded by the illumination light filters 53a and 53b are narrower than the excitation light filter 50E of the light source device 3E. The illumination light filters 53a and 53b shield the wavelength band 500 to 550 nm, including 520 nm of fluorescence of collagen, with an OD value of 2 to 3, because an OD value of 7 or more is shielded by the excitation light filter 50E, as mentioned above.

Therefore in the light which is transmitted through the illumination light filters 53a and 53b and are irradiated onto the subject 21, fluorescence from the illumination light path, which exists in the wavelength band 500 to 550 nm, is decreased. Because of this, light in which wavelength band 500 to 550 nm of visible light including fluorescence from the illumination light path is decreased, is irradiated on the subject 21.

The return lights from the subject 21 are incident on the objective lens 22, and are split into two by a beam splitter 23. Out of the lights split by the beam splitter 23, the reflected lights is formed into an image at the image capturing section 24, and the transmitted lights is formed into an image at the image capturing section 25 via the excitation light cut filter 27E.

The excitation light cut filter 27E has the filter characteristic shown in FIG. 28.

As FIG. 28 shows, the excitation light cut filter 27E shields the wavelength band 400 to 500 nm and 550 to 700 nm of visible light and 740 to 1100 nm of near infrared with an OD value of 7 or more, and transmits only the wavelength band 500 to 550 nm including 520 nm of fluorescence generated by collagen. The intersections of the shield band of the excitation light filter 50E and the shield band of the excitation light cut filter 27E have an OD value of 5 or more.

Therefore in the light transmitted through the excitation light cut filter 27E, the wavelength of 500 to 550 nm including 520 nm of fluorescence generated by collagen is dominant. The light transmitted through the excitation light cut filter 27E is received by the image capturing section 25, and is photoelectrically converted, and the photoelectrically converted image capturing signal is output to the fluorescent image processing circuit 32E. The fluorescent image processing circuit 32E processes the image capturing signal, and generates the image signal (video signal).

The light reflected by the beam splitter 23, on the other hand, is received by the image capturing section 24 and is photoelectrically converted, and the photoelectrically converted image capturing signal is output to the normal image processing circuit 31E. The normal image processing circuit 31E processes the image capturing signal and generates image signal (video signal).

The light being irradiated onto the subject at this time is irradiation light after the wavelength band 500 to 550 nm are shielded with an OD value of 2 to 3 by the illumination light filters 53a and 53b, so the reflected visible light from the subject 21, which the image capturing section 24 receives, has the wavelength band 500 to 550 nm, which is attenuated.

Therefore if the reflected visible light from the subject 21 has a spectrum shown in FIG. 30, for example, the reflected visible light from the subject 21, which the image capturing section 24 receives, has wavelength band 500 to 550 nm, which is attenuated, as shown in FIG. 31.

Therefore in the optical image device 1E of the present embodiment, correction processing is performed to amplify the attenuated wavelength band 500 to 550 nm spectrum, as the broken line portion in FIG. 32 shows, for example. In other words, the image correction circuit 55 estimates peaks and curve shapes for the image signal (video signal) of the normal image generated by the normal image processing circuit 31E, and corrects these estimations by amplifying the signal components corresponding to the wavelength band 500 to 550 nm, based on the information recorded in the illumination light filter information recording section 54. And the image correction circuit 55 outputs the corrected image signal of the normal image to the image synthesizing circuit 33E.

The image synthesizing circuit 33E synthesizes the image signal of the normal image from the image correction circuit 55 and image signal of the fluorescent image from the fluorescent image processing circuit 32E, and outputs synthesized image signal to the monitor 5E. In this way, on the display screen of the monitor 5E, a synthesized image of the normal image 34E and fluorescent image 35E are displayed as one display image.

As a result, the optical imaging device 1E of Embodiment 4 can decrease fluorescence from the illumination light path in the visible light band, and both the normal image 34E and fluorescent image 35E can be acquired, just like the case of Embodiment 2. The reason why such correction of the normal image 34E is possible is because the attenuation of 500 to 550 nm by the illumination filter is limited to OD value 2 to 3, and the light in this band in the normal endoscopic observation is not completely zero or approximately zero. In other words, this illumination light filter has a sufficient performance to shield fluorescence and Raman scattering lights from the illumination light path in fluorescence observation, and has a performance not to allow the light in the visible light band (500 to 550 nm in this case) to attenuate to the level at which image correction becomes impossible. And these performances of the illumination light filter enable acquiring both the normal image 34E and fluorescent image 35E. The optical imaging device 1E can also decrease the Raman scattering light from the illumination light path in the visible light band, although this is not illustrated.

Because of this, the optical imaging device 1E of Embodiment 4 can be used for both fluorescence observation and normal endoscopic observation, and can decrease the fluorescence and Raman scattering lights from the illumination light path.

The above correction processing is also possible for an RGB field-sequential system.

In this case, as FIG. 33 shows, the wavelength band around 500 to 550 nm shielded with OD value 2 to 3 by the illumination light filters 53a and 53b is included in the wavelength band of G (green) 500 to 570 nm. Therefore the image generation device 4F has an image correction circuit 55F for amplifying only G signal, as shown in FIG. 34.

Specifically, the image correction circuit 55F has an amplification circuit 57 for amplifying G signal, which are output from the G signal processing circuit 56g of the normal image processing circuit 31F based on the information from the illumination light filter information recording section 54F. The reference symbol 56r indicates an R signal processing circuit, and 56b indicates a B signal processing circuit, and signal from these signal processing circuits is transmitted through the image correction circuit 55F, and are input to the image synthesizing circuit 33F.

The image synthesizing circuit 33F synthesizes the image signals (R, G, B signals) of the normal image which is input from the image correction circuit 55F, and image signals of the fluorescent image which is input from the fluorescent image processing circuit 32F, and outputs them to the monitor 5F. In this way, on the display screen of the monitor 5F, the normal image 34F and fluorescent image 35F are displayed side by side. The image generation device 4F may separate image signals from the fluorescent image processing circuit 32F into R, G and B signals, compose with the image signals (R, G and B signals) of the normal image for each R, G and B signal, and display a synthesized image on the display screen of the monitor 5F as one display image.

By this, the optical imaging device can perform correction processing even if the configuration is a field-sequential system, and can exhibit an effect similar to Embodiment 4.

The above optical imaging device 1E is structured such that the fluorescence in the visible light band is captured and visible light fluorescence observation is performed, but the present invention is not limited to this, and may be configured such that fluorescence in the near infrared is captured and near infrared fluorescence observation is performed. In this case, an excitation light filter for transmitting only excitation light and a visible light filter for transmitting only visible light, is provided as the guided light filter section, and one of the two light guides 7 and 8 (e.g. light guide 7) is used only for excitation light without including the visible light, and the other (e.g. light guide 8) is used only for visible light without including the excitation light. And the excitation light transmitted through the excitation light filter are transmitted through the light guide 7, for example, and irradiated onto the subject 21, and the visible light transmitted through the visible light filter, on the other hand, are transmitted through the light guide 8, for example, and irradiated onto the subject 21. In other words, the visible light are not included in the lights which are transmitted through by the light guide dedicated to excitation light, and the illumination light filter provided on the excitation light transmission path is configured such that the transmission band is only for the excitation light band.

The optical imaging device which can perform visible light fluorescence observation may be configured as shown in FIG. 35. As FIG. 35 shows, the optical imaging device 1G has a light source device 3G which has an interference filter 58 as a guided light filter section, and a rotary disk 41G having a shielding section 43a and transmission section 43b. The interference filter 58 is configured such that the visible light including the wavelength band of excitation light of collagen are transmitted, and near infrared is shielded with an OD value of 7 or more.

The endoscope 2G has an LED 59a for generating white light at the distal portion 6a of the insertion section 6G, as the light source for capturing a normal image. And the illumination optical system 45b irradiates the white light of the LED 59a onto the subject 21. Therefore the illumination optical system 45b does not have the illumination light filter 53b.

A signal line is extended from the LED 59a, and this signal line is inserted through the insertion section 6G and is electrically connected to the LED control circuit 59 provided in the light source device 3G via a connector 9. The LED control circuit 59 is also connected to a rotary drive circuit 44G. The LED control circuit 59 controls LED 59a so as to turn ON synchronously upon the rotary disk 41G making face the shielding section 43a to the light entering end of the light guide 7 by control of the rotary drive circuit 44G.

Therefore in the optical imaging device 1G, the LED 59a turns ON when the light from the white light source 11 is shielded by the shielding section 43a of the rotary disk 41G, and the white light from the LED 59a is irradiated onto the subject 21 via the illumination optical system 45b.

When the rotary disk 41G rotates a half turn from the state in FIG. 35, the transmission section 43b of the rotary disk 41G faces the light entering end 7a of the light guide 7 and visible light from the white light source 11 is incident on the light entering end 7a of the light guide 7 via the collimator lens 12G and interference filter 58. The visible light which has been entered on the light entering end 7a is transmitted through the light guide 7, then are transmitted from the end face of the light guide 7 to the illumination optical system 45a, and are irradiated onto the subject 21.

In other words, the rotary disk 41G is controlled and driven by the rotary drive circuit 44G, so that the white light from the LED 59a and the visible light from the white light source 11 are alternately irradiated onto the subject 21. Therefore in the optical imaging device 1G, the white light from the LED 59a and the visible light from the white light source 11 are alternately irradiated onto the subject 21. The rotary drive circuit 44G sends synchronization signal synchronizing with the rotation of the rotary disk 41G to the normal image processing circuit 31G and fluorescent image processing circuit 32G of the image generation device 4G. The normal image processing circuit 31G and fluorescent image processing circuit 32G perform processing to generate the normal image and fluorescent image respectively synchronizing with the received synchronization signal.

The normal image processing circuit 31G and fluorescent image processing circuit 32G incorporate an image capturing drive circuit, which is not illustrated, respectively. Each image capturing drive circuit applies the image capturing drive signal to the image capturing sections 24 and 25 respectively, synchronizing with the synchronization signal, performs photoelectric conversion for the light received by the image capturing sections 24 and 25 respectively, and outputs the acquired image capturing signal. In the above description, the rotary drive circuit 44G generates the synchronization signal, and sends them to the image generation device 4G, but the image generation device 4G may generate the synchronization signal, and send the generated synchronization signal to the rotary drive circuit 44G.

The image signal (video signal) of the normal image and image signal (video signal) of the fluorescent image, which are generated by the normal image processing circuit 31G and fluorescent image processing circuit 32G, are output to the monitor 5G via the image synthesizing circuit 33G for synthesizing images. On the display screen of the monitor 5G, the normal image and fluorescent image are displayed in a composite state, for example.

The monitor 5G in FIG. 35 shows an example of a display of the images acquired in this state. Here the reference symbol 34G indicates a normal image by reflected light, and 35G indicates a fluorescent image by the fluorescence emitted by the excitation light irradiated onto the subject 21. The image generation device 4G may switch among a state where a normal image 34G is displayed on the display screen of the monitor 5G without image synthesis processing by the image synthesizing circuit 33G, a state where a fluorescent image 35G is displayed on the display screen of the monitor 5G without image synthesis processing by the image synthesizing circuit 33G, and a state where the image synthesizing circuit 33G by the select operation of the display select switch 36G performs image synthesis processing and the normal image 34G and fluorescent image 35G are displayed on the display screen of the monitor 5G as a composite display (or displayed side by side).

The function of a variant form with this configuration will be described.

As FIG. 35 shows, the optical imaging device 1G is activated by operating the power supply switch, which is not illustrated, in a state where the endoscope 2G is connected to the light source device 3G. The operator inserts the insertion section 6G of the endoscope 2G into the body cavity, guides the distal portion 6a of the insertion section 6G into a target region, and performs fluorescence observation. In the present embodiment, it is assumed that the visible light fluorescence observation is performed using collagen as the endogenous fluorescent substance.

The operator inserts the insertion section 6G of the endoscope 2G into the body cavity of the patient, and guides the distal portion 6a into the target region. Until the distal portion 6a of the insertion section 6G is guided to the target region, the operator displays only the normal image on the display screen of the monitor 5G by operating the display select switch 36G.

When the distal portion 6a of the insertion section 6G reaches the target region, the operator starts visible light fluorescence observation. The motor 42G rotates at a constant speed, and the rotary disk 41G also rotates according to the rotation of the motor 42G. When the shielding section 43a of the rotary disk 41G positions at the light entering end 7a of the light guide 7, the LED 59a turns ON, and the white light from the LED 59a is irradiated onto the subject 21 via the illumination optical system 45b.

The reflected light from the subject 21 is reflected by the beam splitter 23, an image based on the light is formed at the image capturing section 24, and the image is captured by the image capturing section 24. The image capturing signal from the image capturing section 24 is processed by the normal image processing circuit 31G. The normal image processing circuit 31G processes the image capturing signal, generates the image signal of the normal image, and outputs the image signal of the normal image to the image synthesizing circuit 33G.

When the transmission section 43b of the rotary disk 41G positions at the light entering end 7a of the light guide 7, on the other hand, the light from the white light source 11, which has been transmitted through the interface filter 58, is incident on the light entering end 7a of the light guide 7 via the transmission section 43b. In this case, the interference filter 58 transmits the visible light, including the wavelength band of the excitation light of collagen, and shields near infrared with an OD value of 7 or more. Therefore the light which is transmitted through the interference filter 58 and is incident on the light entering end 7a of the light guide 7 are only the visible light band 400 to 780 nm, including 450 nm of excitation light of collagen.

The light which is incident on the light entering end 7a is transmitted by the light guide 7, and are transmitted from the end face to the illumination optical system 45a, and are irradiated onto the subject 21. At this time, similarly to the explanation in Embodiment 4, the illumination light filter 53a provided in the illumination optical system 45a, shields the wavelength band 500 to 550 nm including 520 nm of fluorescence of collagen with an OD value of 2 to 3, and transmits the visible light band 400 to 480 nm and 550 to 700 nm, including the 450 nm of excitation light of collagen.

Because of this, the light from the white light source 11 is transmitted through the illumination light filter 53a and become light where fluorescence from the illumination light path, which exists in the wavelength band 500 to 550 nm, is decreased. The return lights from the subject 21 are incident on the objective lens 22, transmitted through the beam splitter 23, and an image based on the light is formed at the image capturing section 25 via the excitation light cut filter 27G, and the image is captured by the image capturing section 25. At this time, the excitation light cut filter 27G shields the wavelength band 400 to 500 nm, and 550 to 700 nm of visible light, and wavelength band 700 to 1100 nm of near infrared, with an OD value of 7 or more, and transmits only the wavelength band 500 to 550 nm including 520 nm of fluorescence generated by collagen. Therefore in the light transmitted through the excitation light cut filter 27G, the wavelength band 500 to 550 nm, including 520 nm of fluorescence generated by collagen, is dominant.

The image capturing signal from the image capturing section 25 is processed by the fluorescent image processing circuit 32G. The fluorescent image processing circuit 32G processes the image capturing signal and generates the image signal of the fluorescent image, and outputs the image signal of the generated fluorescent image to the image synthesizing circuit 33G.

The image synthesizing circuit 33G synthesizes the image signal of the normal image from the normal image processing circuit 31G and the image signal of the fluorescent image from the fluorescent image processing circuit 32G, and outputs the synthesized image signal to the monitor 5G. In this way, on the display screen of the monitor 5G, a synthesized image of the normal image 34G and fluorescent image 35G is displayed as one display image.

As a result, the optical imaging device 1G of the variant form can decrease fluorescence from the illumination light path in the visible light band, and both the normal image 34G and fluorescent image 35G can be acquired, just like the above mentioned Embodiment 4. The optical imaging device 1G can also decrease the Raman scattering light from the illumination light path in the visible light band in the same way, although this is not illustrated. Because of this, the optical imaging device 1G of the variant form can be used for both fluorescence observation and normal endoscopic observation, and can decrease the fluorescence and Raman scattering lights from the illumination light path.

Also the optical imaging device 1G of the variant form has a configuration to irradiate the white light from the LED 59a and the visible light from the white light source 11 alternately onto the subject 21, so the illumination light by the LED 59a does not become excessively strong, and the visible light image and fluorescent image balance in terms of intensity.

Embodiment 5

Figure 36:
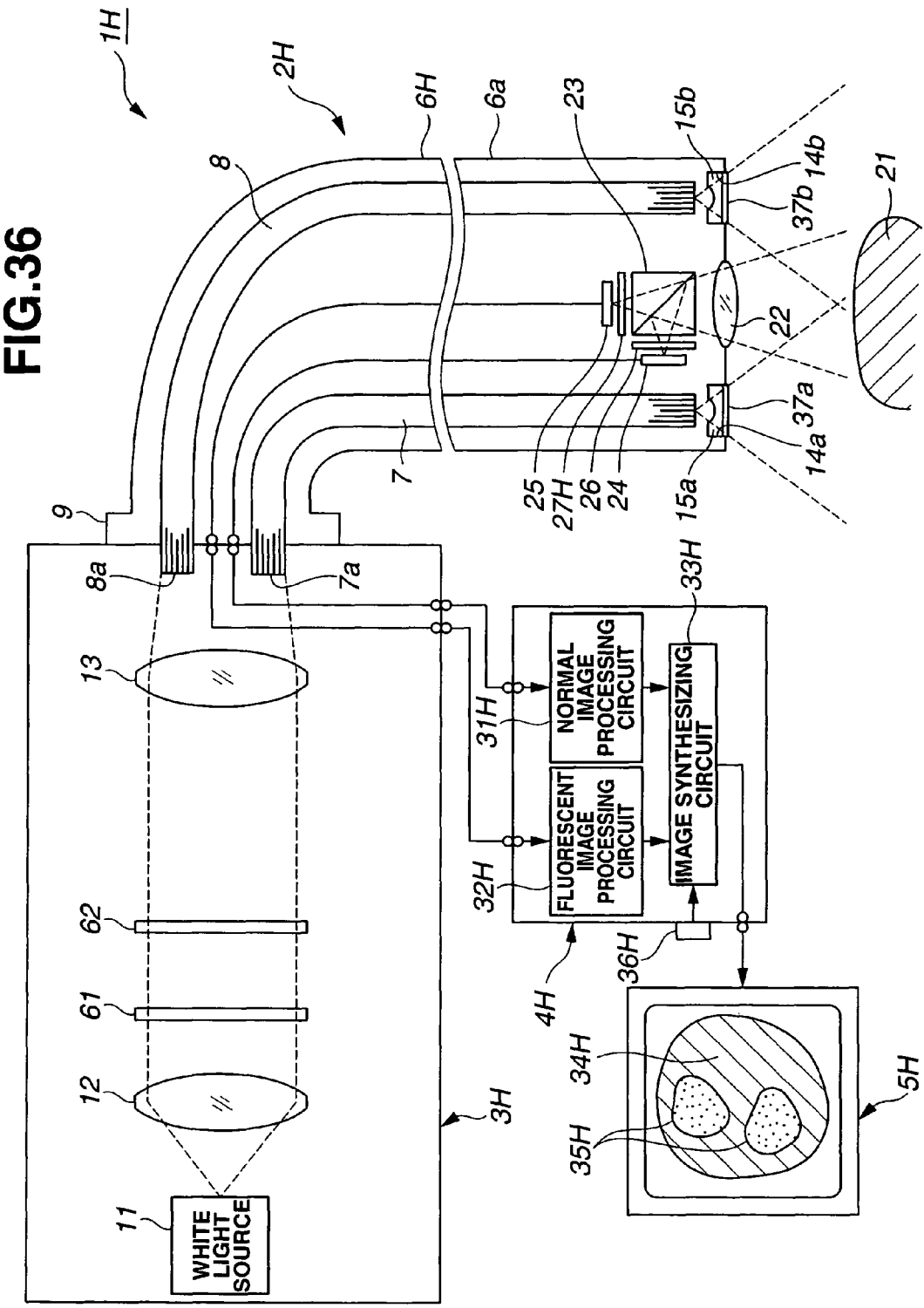
FIG. 36 is a diagram depicting an entire configuration of the optical imaging device according to Embodiment 5.
Figure 37:
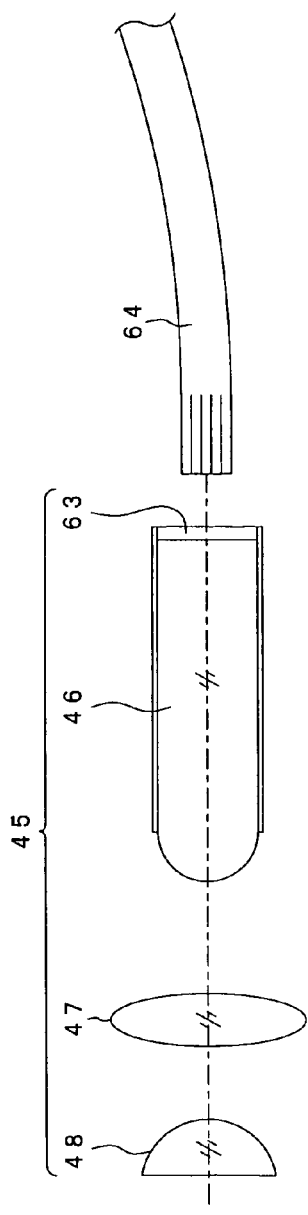
FIG. 37 is a diagram depicting a first variant form of the illumination light filter.
Figure 38:
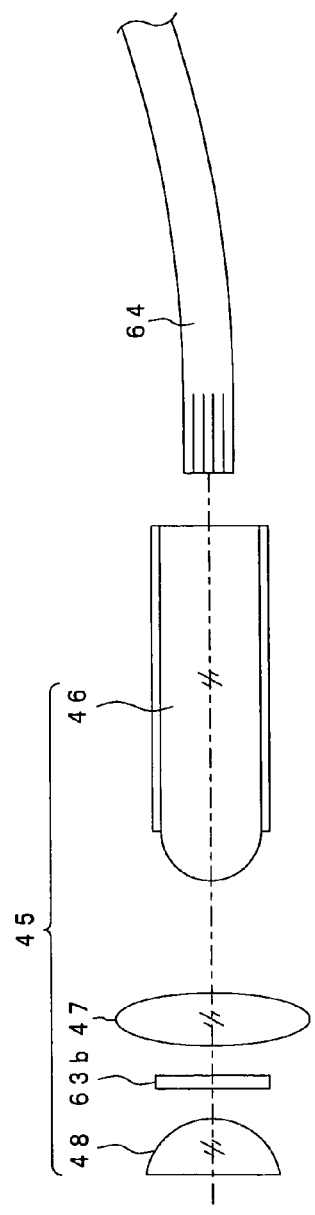
FIG. 38 is a diagram depicting a second variant form of the illumination light filter.
Figure 39:
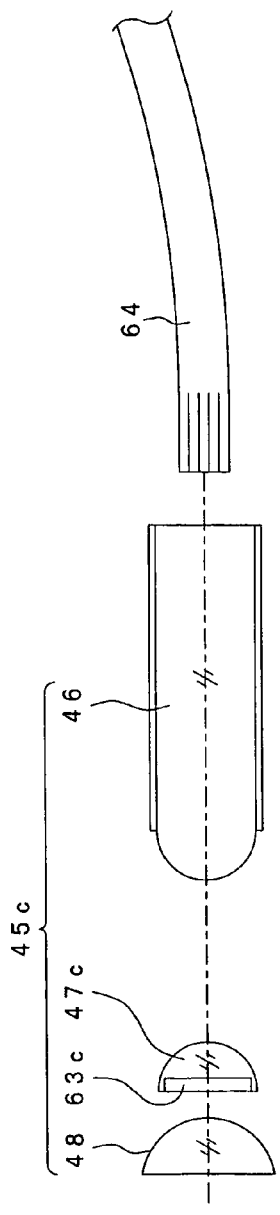
FIG. 39 is a diagram depicting a third variant form of the illumination light filter.
Figure 40:
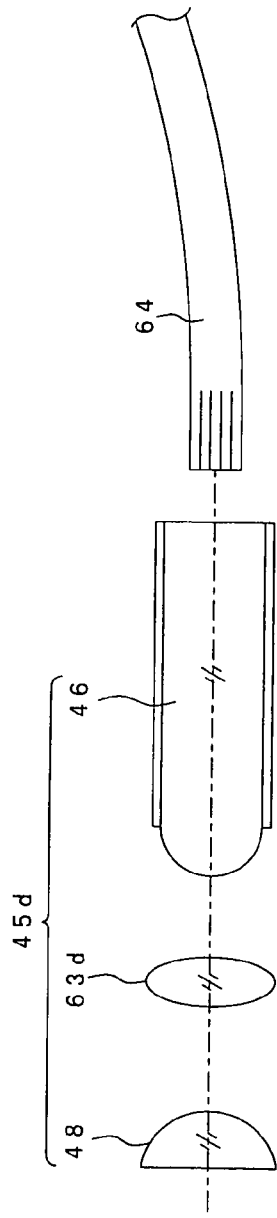
FIG. 40 is a diagram depicting a fourth variant form of the illumination light filter.
Figure 41:
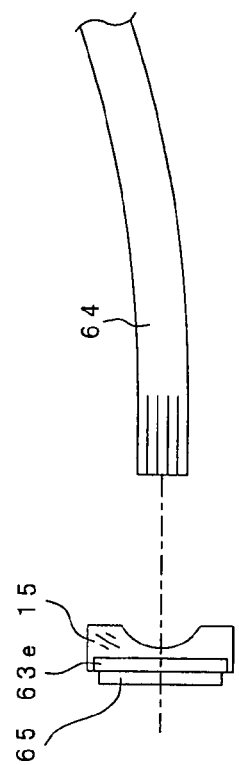
FIG. 41 is a diagram depicting a fifth variant form of the illumination light filter.
Figure 42:
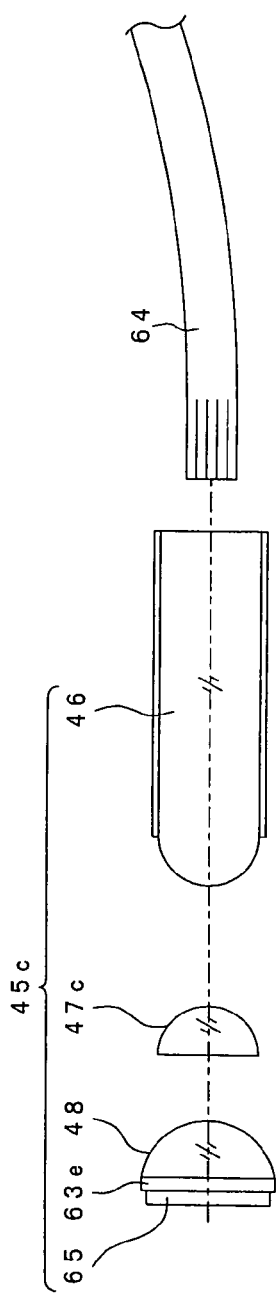
FIG. 42 is a diagram depicting a sixth variant form of the illumination light filter.
Figure 43:
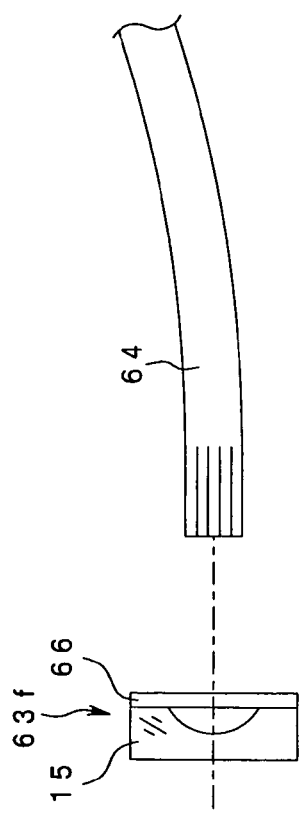
FIG. 43 is a diagram depicting a seventh variant form of the illumination light filter.
Figure 44:
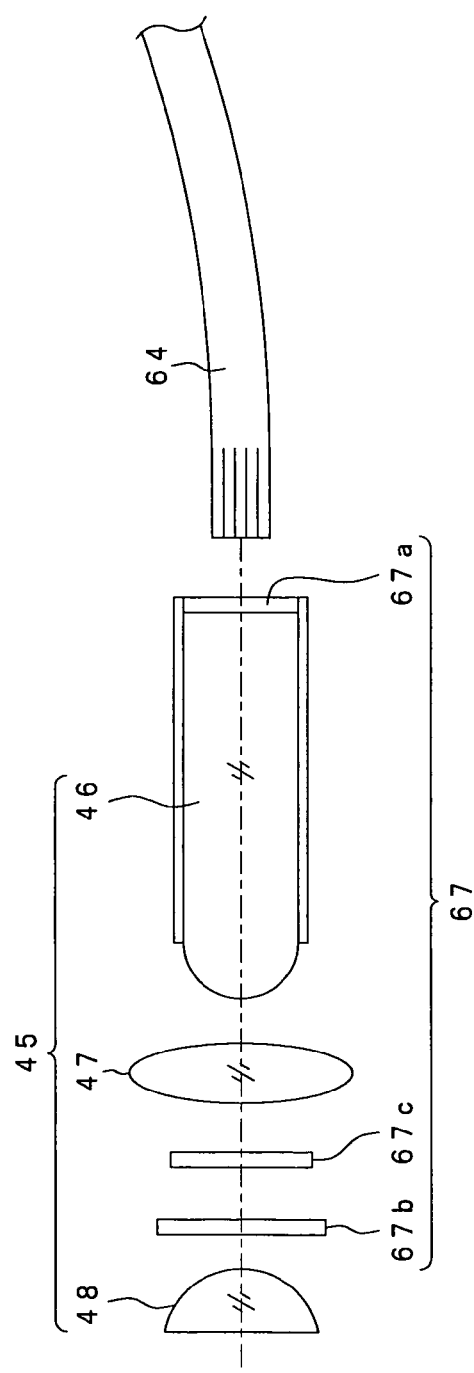
FIG. 44 is a diagram depicting an eighth variant form of the illumination light filter.
Figure 45:
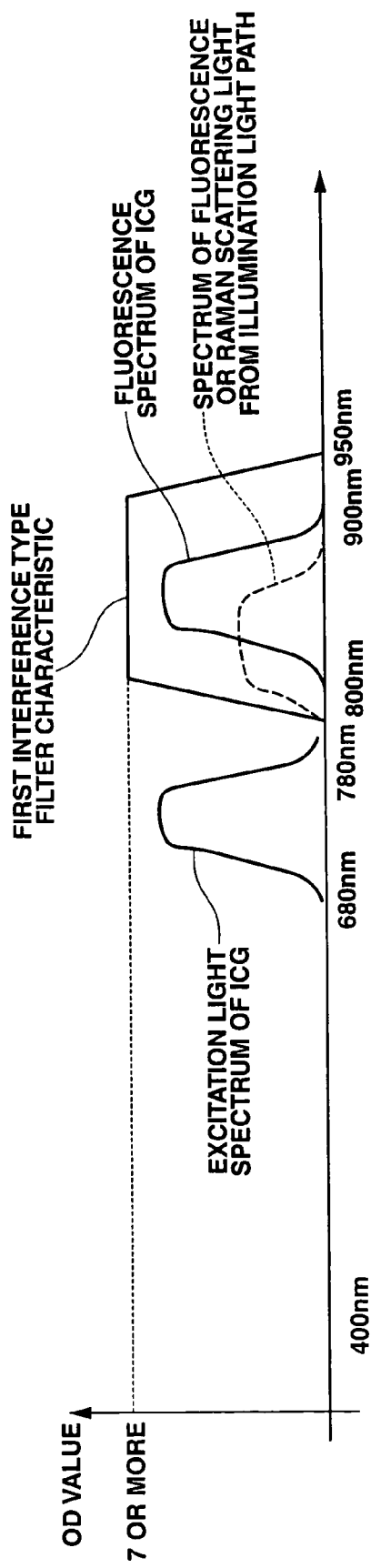
FIG. 45 is a graph depicting the filter characteristic of a first interference filter in FIG. 44.
Figure 46:
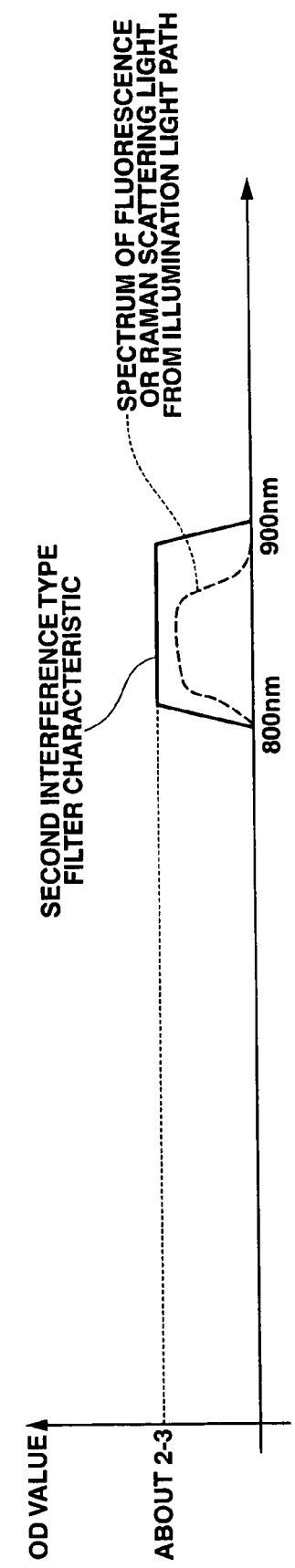
FIG. 46 is a graph depicting the filter characteristic of a second interference filter in FIG. 44.
Figure 47:
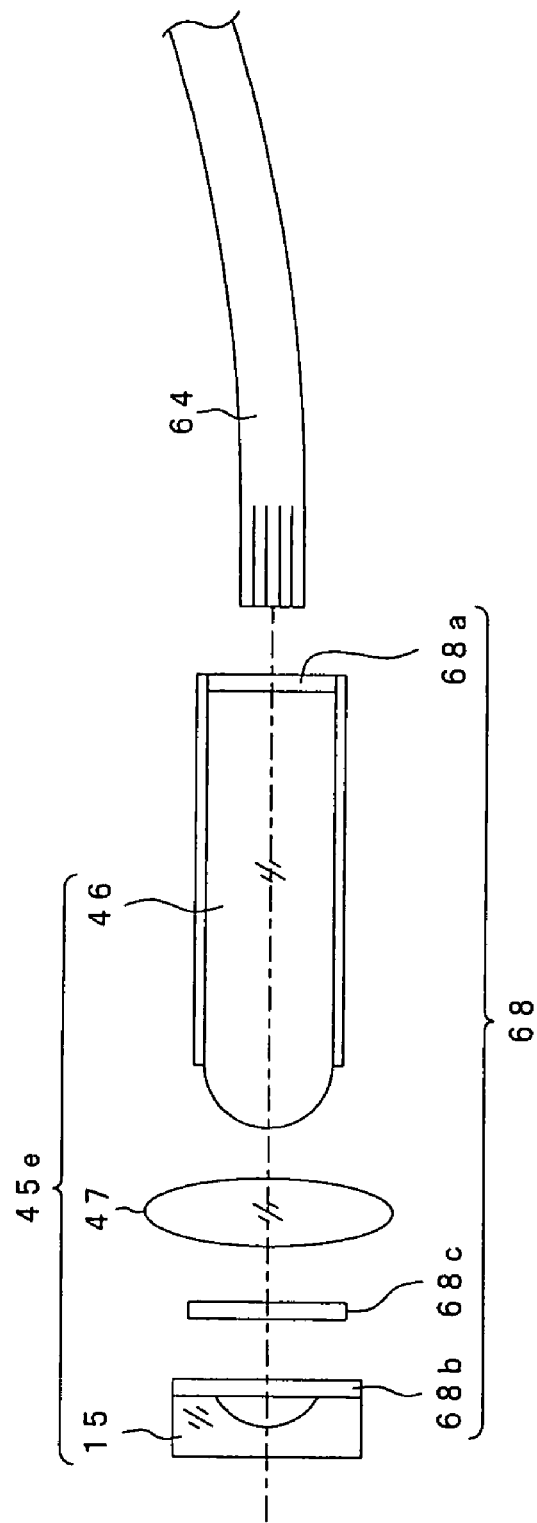
FIG. 47 is a diagram depicting a ninth variant form of the illumination light filter.
Figure 48:
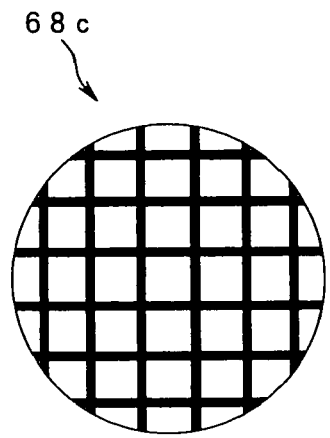
FIG. 48 is a diagram depicting a first configuration of the absorption filter in FIG. 47.
Figure 49:
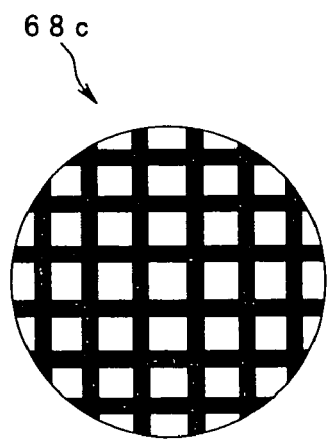
FIG. 49 is a diagram depicting a second configuration of the absorption filter in FIG. 47.
Figure 50A:
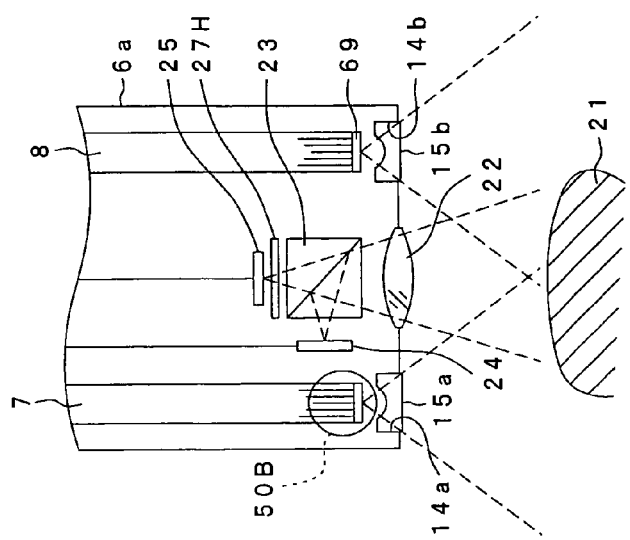
FIG. 50A and FIG. 50B are diagrams depicting a tenth variant form of the illumination light filter.
Figure 50B:
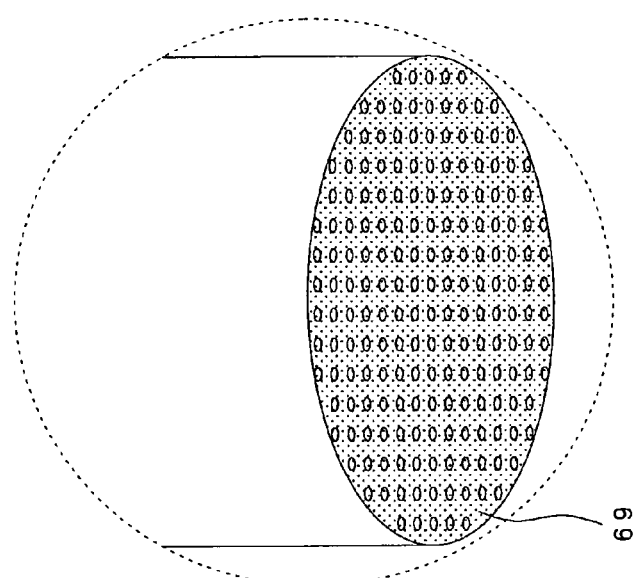

FIG. 36 to FIG. 50B relate to Embodiment 5 of the present invention, where FIG. 36 is a diagram depicting an entire configuration of the optical imaging device according to Embodiment 5, FIG. 37 is a diagram depicting the first variant form of the illumination light filter, FIG. 38 is a diagram depicting the second variant form of the illumination light filter, FIG. 39 is a diagram depicting the third variant form of the illumination light filter, FIG. 40 is a diagram depicting the fourth variant form of the illumination light filter, FIG. 41 is a diagram depicting the fifth variant form of the illumination light filter, FIG. 42 is a diagram depicting the sixth variant form of the illumination light filter, FIG. 43 is a diagram depicting the seventh variant form of the illumination light filter, FIG. 44 is a diagram depicting the eighth variant form of the illumination light filter, FIG. 45 is a graph depicting the filter characteristic of the first interference filter in FIG. 44, FIG. 46 is a graph depicting the filter characteristic of the second interference filter in FIG. 44, FIG. 47 is a diagram depicting the ninth variant form of the illumination light filter, FIG. 48 is a diagram depicting the first configuration of the absorption filter in FIG. 47, FIG. 49 is a diagram depicting the second configuration of the absorption filter in FIG. 47, and FIG. 50A and FIG. 50B are diagrams depicting the tenth variant form of the illumination light filter.

Embodiment 5 has a configuration where the interference filter and absorption filter are provided in the light source device as a guided light filter section for performing infrared fluorescence observation. The rest of the configuration is the same as Embodiment 1, therefore description thereof is omitted, and the same components are described denoting with the same reference symbols.

As FIG. 36 shows, an optical imaging device 1H of Embodiment 5 has a light source device 3H where an interference filter 61 and an absorption filter 62 are provided as a guided light filter section, so that infrared fluorescence observation can be performed, just like the above mentioned Embodiment 1.

The interference filter 61 transmits visible light and excitation light, and shields near infrared with an OD value of 7 or more. The absorption filter 62, on the other hand, absorbs multiple reflection lights generated between the interference filter 61 and the illumination light filters 37a and 37b described in Embodiment 1, and decreases this multiple reflection. The rest of the configuration is the same as Embodiment 1, so description thereof is omitted.

The function of Embodiment 5 based on this configuration will be described.

As FIG. 36 shows, the optical imaging device 1H is activated by operating the power supply switch, which is not illustrated, in a state where the endoscope 2H is connected to the light source device 3H. The operator inserts the insertion section 6H of the endoscope 2H into the body cavity, and guides the distal portion 6a of the insertion section 6H into a target region, and performs fluorescence observation.

In other words, the operator administers the fluorescent substance into the body of the patient in advance. The fluorescent substance accumulates in a lesioned part when a predetermined time elapses after administration. In the present embodiment, it is assumed that infrared fluorescence observation is performed using fluorescence dye Cy (carbocyanine) 7 as the fluorescent substance.

The operator inserts the insertion section 6H of the endoscope 2H into the body cavity of the patient, and guides the distal portion 6a into a target region. Until the distal portion 6a of the insertion section 6H is guided to the target region, the operator displays only the normal image on the display screen of the monitor 5H by operating the display select switch 36H. When the distal portion 6a of the insertion section 6H reaches the target region, the operator starts infrared fluorescence observation.

To the light incident ends 7a and 8a of the light guides 7 and 8, light from the white light source 11 is incident on via the interference filter 61 and absorption filter 62. In this case, the interference filter 61 transmits the wavelength band 400 to 750 nm including the visible light and excitation light 680 to 740 nm of the luorescence dye Cy 7, and shields the wavelength bands 750 to 1100 nm of near infrared with an OD value of 7 or more. Therefore the light which is transmitted through the interference filter 61 and is incident on the light incident ends 7a and 8a of the light guides 7 and 8, are only the wavelength band 400 to 750 nm of the illumination light including 680 to 740 nm of the excitation light of the fluorescence dye Cy 7.

These light is transmitted by the light guides 7 and 8 emitted from the light emitting ends of the light guides 7 and 8, and is incident on the illumination lenses 15a and 15b. At this time, the light which is incident on the illumination lenses 15a and 15b include fluorescence from the illumination light path. The fluorescence from the illumination light path exist around the wavelength band 760 to 850 nm of fluorescence of the fluorescence dye Cy 7.

The light which is incident on the illumination lenses 15a and 15b are irradiated onto the subject 21 via the illumination light filters 37a and 37b. The multiple reflection which is generated between the interference filter 61 and illumination light filters 37a and 37b at this time is absorbed by the absorption filter 62.

The illumination light filters 37a and 37b transmit the wavelength band 400 to 750 nm including the visible light and excitation light 680 to 740 nm of the fluorescence dye Cy 7, and shield the wavelength band 750 to 1100 nm of near infrared including the fluorescence from the illumination light path with an OD value of 7 or more. Therefore the only light which is transmitted through the illumination light filters 37a and 37b and are irradiated onto the subject 21 are the wavelength band 400 to 750 nm of the illumination light including 680 to 740 nm of the excitation light of the fluorescence dye Cy 7.

Therefore only visible light and excitation light, which are the wavelength band 400 to 750 nm, after the wavelength band 750 to 1100 nm of near infrared including the fluorescence from the illumination light path is shielded, is irradiated on the subject 21. Since near infrared including the fluorescence from the illumination light path is shielded, the return lights from the subject 21 are only fluorescence generated by the fluorescence dye Cy 7 included in the subject 21 and the reflected visible light from the subject 21, which enter the objective lens 22.

The return lights from the subject 21 are only the wavelength band 400 to 750 nm of the reflected light from the subject 21 and the wavelength band 760 to 850 nm of fluorescence generated by the fluorescence dye Cy 7 included in the subject 21. The return lights from the subject 21 enter the objective lens 22, and are split into two by a beam splitter 23. Out of the lights split by the beam splitter 23, the reflected light form an image on the image capturing section 24 via the visible light filter 26, and the transmitted light form an image on the image capturing section 25 via the excitation light cut filters 27H.

The excitation light cut filter 27H shields the wavelength band 400 to 750 nm of the visible light with an OD value of 7 or more, and transmits only the wavelength band 760 to 850 nm of fluorescence generated by the fluorescence dye Cy 7. Therefore the only light which is transmitted through the excitation light cut filter 27H is the wavelength band 760 to 850 nm of fluorescence generated by the fluorescence dye Cy 7. In this way, the image capturing section 25 can receive only the wavelength band 760 to 850 nm of fluorescence generated by the fluorescence dye Cy 7.

The information on the light received by the image capturing section 24 is output to the monitor 5H as a normal image via the normal image processing circuit 31H and the image synthesizing circuit 33H of the image generation device 4H. The information on the light received by the image capturing section 25 is output to the monitor 5H as the fluorescent image, via the fluorescent image processing circuit 32H and image synthesizing circuit 33H of the image generation device 4H. In this way, a synthesized image of the normal image 34H and fluorescent image 35H is displayed on the display screen of the monitor 5H as one display image.

As a result, the optical imaging device 1H of Embodiment 5 can exhibit an effect similar to Embodiment 1, and also because the interference filter 61 is provided inside the light source device 3H as the guided light filter section, the OD values of the illumination light filters 37a and 37b placed at the distal portion 6a of the insertion section 6H need not be set high, and it is also unnecessary to shield light other than the fluorescence or Raman scattering light from the illumination light path. Also the optical imaging device 1H of Embodiment 5 has the absorption filter 62, so the multiple reflection generated between the interference filter 61 and illumination light filters 37a and 37b can be decreased, and a more precise fluorescent image and normal image can be acquired.

If the OD value of the interference filter 61 is 7 and the OD value of the absorption filter 62 is 3, then the performance of the guided light filter section can be an OD value of 10. Since multiple reflection is not generated between the absorption filter 62 and interference filter 61, performance can be easily improved by using this combination, and fluorescence with a lower intensity can be observed.

The illumination light filter provided in the illumination optical system of the endoscope may be configured as shown in FIG. 37 to FIG. 40. The illumination light filters having these configurations are not limited to the application to the endoscope of the present embodiment, but may be applied to endoscopes and optical probes of other embodiments.

As FIG. 37 shows, the illumination light filter 63 is placed in the illumination optical system 45 provided at the distal portion 6a of the insertion section 6. The illumination optical system 45 comprises a rod lens 46 facing the light emitting end of the light guide 64, and relay lens (biconvex lens) 47, and an illumination lens (plano-convex lens) 48. The illumination light filter 63 includes an optical thin film formed on the light entering end face of the rod lens 46. The illumination light filter 63 is an interference filter.

As FIG. 38 shows, the illumination light filter 63b is placed between the relay lens 47 of the illumination optical system 45 and the illumination lens 48. The illumination light filter 63b is an absorption filter, and is a cover glass as a light absorption element made of a light absorption material (light absorption substance).

As FIG. 39 shows, the illumination light filter 63c is placed in the illumination optical system 45c. The illumination optical system 45c comprises a rod lens 46 facing the light emitting end of the light guide 64, a relay lens (plano-convex lens) 47c and an illumination lens (plano-convex lens) 48. The illumination light filter 63c is made up of as an optical thin film formed on the light emitting end face of the relay lens 47c. The illumination light filter 63c is an interference filter.

As FIG. 40 shows, the illumination light filter 63d is placed in the illumination optical system 45d. The illumination optical system 45d comprises a rod lens 46 facing the light emitting end of the light guide 64 and an illumination lens (plano-convex lens) 48. The illumination light filter 63d is placed between the rod lens 46 and illumination lens 48. The illumination light filter 63d is a lens as a light absorption element made of light absorption material (light absorption substance).

The illumination light filter may also be configured as depicted in FIG. 41 to FIG. 43.

As FIG. 41 shows, in the illumination light filter 63e, an optical thin film is formed on the light emitting end face of an illumination lens (plano-concave lens) 15 as an illumination optical system provided at the light emitting end of the light guide 64, and an SiO$_2$ substrate 65 is attached to this optical thin film face. The illumination light filter 63e is an interface filter. If this configuration is used, the illumination light filter 63e is covered with the SiO$_2$ substrate 65, so the filter resistance improves. In the above illumination light filter 63e, the optical thin film is formed on the illumination lens 15 and then the SiO$_2$ substrate 65 is attached thereon, but the optical thin film may be formed on the SiO$_2$ substrate 65 and this film face may be attached to the light emitting end of the illumination lens 15.

As FIG. 42 shows, the illumination light filter 63e may be placed at the light emitting end of the illumination lens 48 provided in the illumination optical system 45c. In other words, the illumination optical system 45c comprises the rod lens 46, relay lens 47c and illumination lens 48, as mentioned above. And in the illumination light filter 63e, an optical thin film is formed on the light emitting end face of the illumination lens 48, which is a flat face, and the SiO$_2$ substrate 65 is attached to this optical thin film face. The optical thin film may be formed on the SiO$_2$ substrate 65 side instead of the illumination lens 48 side, which is as mentioned above.

Also as FIG. 43 shows, the illumination light filter 63f may be constructed by attaching a plane parallel interference filter 66, on which the optical thin film is formed, to the light entering end of the illumination lens 15. In the case of the illumination light filter 63f having this configuration, durability improves compared with the configuration forming the optical thin film on the light emitting end of the illumination lens 15.

The illumination light filter may be configured as shown in FIG. 44. The illumination filter having the configuration shown in FIG. 44 is suitable for combining with the endoscope according to Embodiment 1 or Embodiment 2.

As FIG. 44 shows, the illumination light filter 67 is placed in the illumination optical system 45. The illumination light filter 67 comprises a first interference filter 67a constructed by forming an optical thin film on the light entering end face of the rod lens 46, a second interference filter 67b placed between the relay lens 47 and illumination lens 48, and an absorption filter 67c placed between the first interference filter 67a and second interference filter 67b.

The illumination light filter 67 having this configuration uses two filters, the first interference filter 67a and second interference filter 67b, so the effect to transmit or shield light with a predetermined wavelength band can be improved. Also this illumination light filter 67 has the absorption filter 67c, so multiple reflection which is generated between the first interference filter 67a and second interference filter 67b can be prevented.

In the illumination light filter 67, one of the first interference filter 67a and the second interference filter 67b may be a filter for excitation light and the other may be a filter for decreasing the fluorescence or Raman scattering light from the illumination light path, as shown in FIG. 45 and FIG. 46. FIG. 45 and FIG. 46 show the case when the fluorescence dye ICG (Indocyanine Green) is used as the fluorescent substance.

FIG. 45 shows the filter characteristic of the first interference filter 67a and FIG. 46 shows the filter characteristic of the second interference filter 67b.

As FIG. 45 shows, the first interference filter 67a transmits the wavelength band 400 to 800 nm including 680 to 780 nm of the excitation light of the fluorescence dye ICG, and shields the wavelength 800 to 950 nm of near infrared including fluorescence or Raman scattering light from the illumination light path existing in 800 to 900 nm of the fluorescence of the fluorescence dye ICG, with an OD value of 7 or more.

As FIG. 46 shows, the second interference filter 67b transmits wavelength band 400 to 800 nm including 680 to 780 nm of the excitation light of the fluorescence dye ICG, and shields the wavelength 800 to 950 nm of near infrared including fluorescence or Raman scattering light from the illumination light path existing in 800 to 900 nm of the fluorescence of the fluorescence dye ICG, with an OD value of about 2 to 3.

By this, the first interference filter 67a can be used as a filter for exciting the fluorescence dye ICG, and the second interference filter 67b can be used as a filter for shielding the fluorescence or Raman scattering light from the illumination light path. The second interference filter 67b is placed closer to the distal end side as much as possible to shield fluorescence or Raman scattering light from the illumination light path.

If the light source having the guided light filter is used, just like the case of Embodiment 3 or Embodiment 4, it is preferable to set both the OD values of the first interference filter and second interference filter to about 3, then the performance of the OD value 6 can be acquired as a whole.

Generally in the visible light band, the intensity of fluorescence from the illumination light path, particularly fluorescence from the light guide, increases as the wavelength decreases. Therefore if the intensity of the fluorescence of the subject to be observed is extremely low, or if the wavelength of fluorescence thereof is short, then the performance of the illumination light filter may have to be higher than OD value 3. If the configuration shown in FIG. 44 is used in such a case, a high effect can be exhibited.

The illumination light filter may be configured as shown in FIG. 47.

As FIG. 47 shows, the illumination light filter 68 is placed in the illumination optical system 45e. The illumination optical system 45e comprises a rod lens 46, facing the light emitting end of the light guide 64, a relay lens (plano-convex lens) 47 and an illumination lens (plano-convex lens) 15.

The illumination light filter 68 comprises an interference filter 68a which is constructed by forming the optical thin film on the light entering end face of the rod lens 46, a plane parallel interference filter 68b, attached to at the light entering end of the illumination lens 15, and an absorption filter 68c, placed between the interference filter 68a and plane parallel interference filter 68b.

The absorption filter 68c is made up of metal thin film formed on the substrate in mesh, as shown in FIG. 48 and FIG. 49. The absorption filter 68c is configured such that transmitted light is attenuated by a part of light that causes an irregular reflection by the metal thin film formed in the mesh.

In this absorption filter 68c, the transmittance can be set by changing the area ratio of the metal thin film, and the entire band of transmitting light can be uniformly attenuated since there is no wavelength characteristic. In the configuration shown in FIG. 49, mesh is denser, that is the area ratio of the metal thin film is greater so as to set the transmittance lower, compared with the configuration in FIG. 48.

The illumination light filter may be provided at the end face of the light guide, as shown in FIG. 50A and FIG. 50B. As FIG. 50A and FIG. 50B show, the illumination light filter 69 is installed on the light emitting end face of the light guides 7 and 8 respectively. The illumination light filter 69 is made up of the optical thin film formed on the light emitting end faces of the light guides 7 and 8, or by attaching a substrate on which the optical thin film is formed. The optical imaging device having this configuration can save space of the distal portion 6a of the endoscope, so an endoscope with a thinner diameter can be configured. The illumination light filters described in FIG. 37 to FIG. 50B can be used for both infrared fluorescence observation and visible light fluorescence observation.

Embodiment 6

Figure 52:
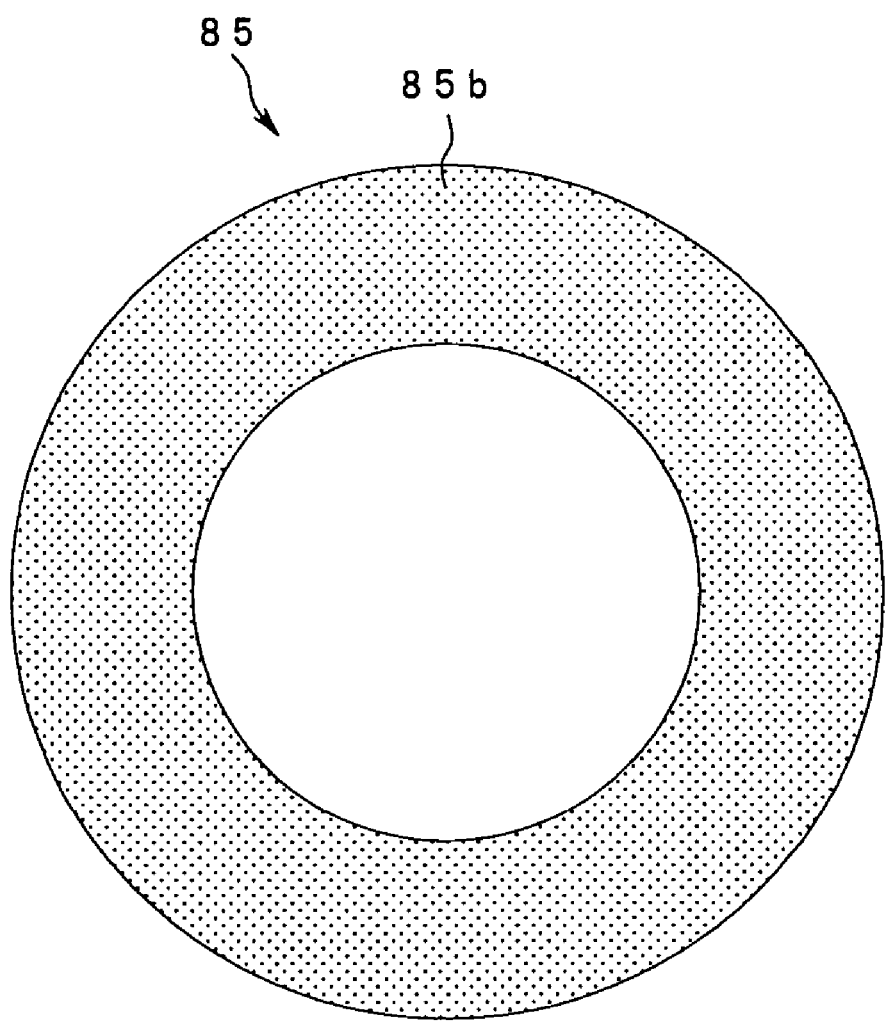
FIG. 52 is a diagram depicting a variant form of the illumination light filter in FIG. 51.
Figure 53:
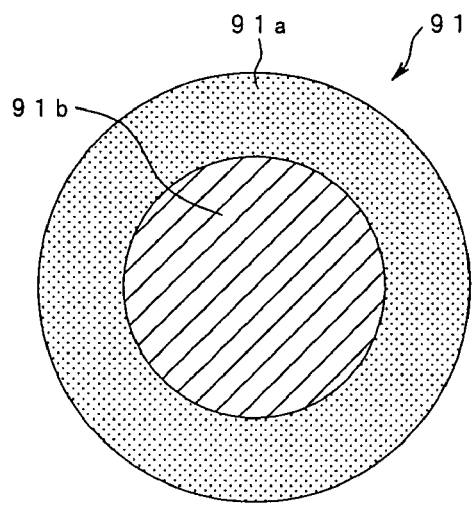
FIG. 53 is a diagram depicting a first variant form of the optical filter.
Figure 54:
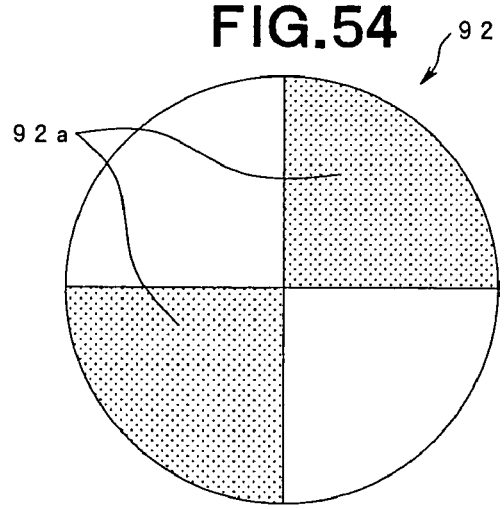
FIG. 54 is a diagram depicting a second variant form of the optical filter.
Figure 55:
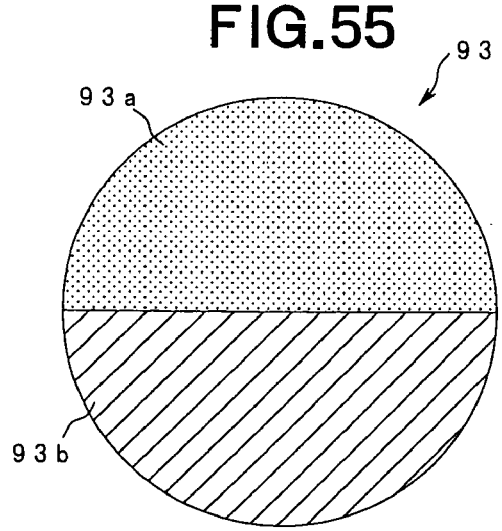
FIG. 55 is a diagram depicting a third variant form of the optical filter.
Figure 56:
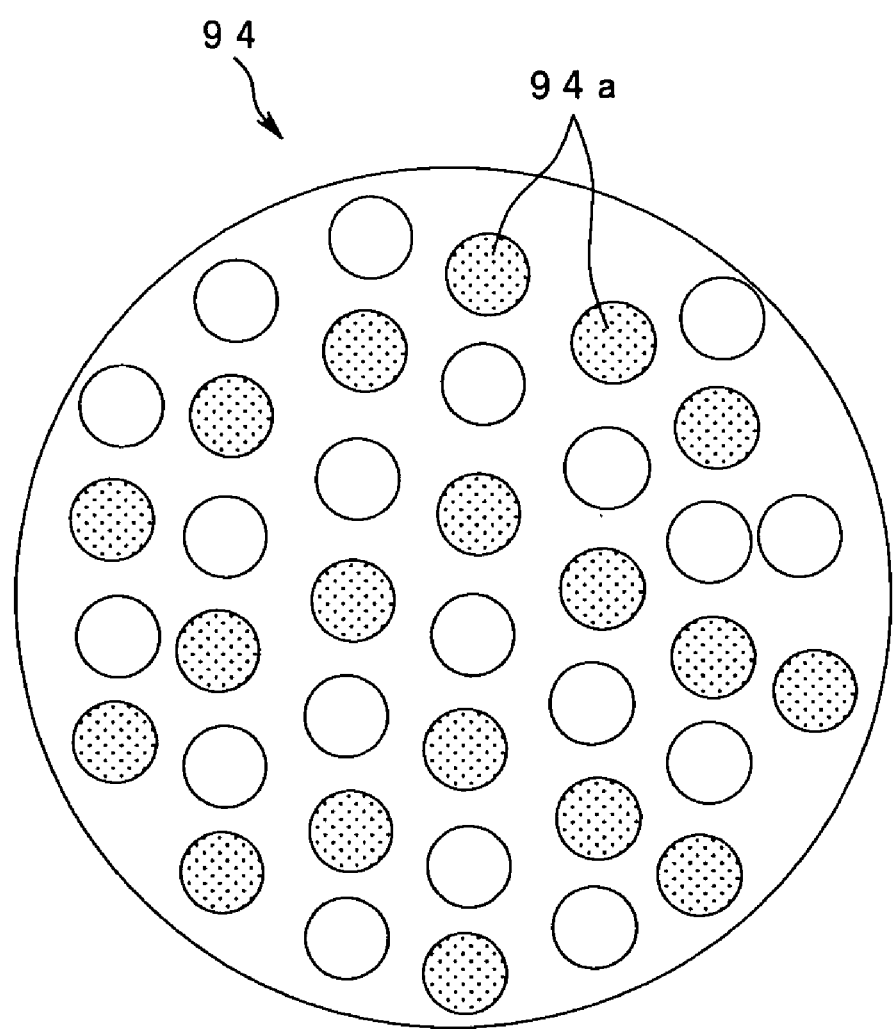
FIG. 56 is a diagram depicting a fourth variant form of the optical filter.

FIG. 51 to FIG. 56 are related to Embodiment 6 of the present invention, where FIG. 51 is a diagram depicting an entire configuration of the optical probe device constituting the optical imaging device according to Embodiment 6, FIG. 52 is a diagram depicting a variant form of the illumination light filter in FIG. 51, FIG. 53 is a diagram depicting a first variant form of the optical filter, FIG. 54 is a diagram depicting a second variant form of the optical filter, FIG. 55 is a diagram depicting a third variant form of the optical filter, and FIG. 56 is a diagram depicting a fourth variant form of the optical filter.

The above mentioned embodiments 1 to 5 have configurations where the endoscope is used, but in the configuration of Embodiment 6, an optical probe which is inserted through a channel for inserting a treatment tool of the endoscope is used. The rest of the configuration is the same as Embodiment 1, therefore description thereof is omitted, and the same components are described denoting the same reference symbols.

As FIG. 51 shows, the optical imaging device of Embodiment 6 has an endoscope apparatus, which is configured such that an endoscopic image by normal visible light can be acquired (not illustrated), and an optical probe device 70, which is combined with the endoscope apparatus for acquiring a fluorescent image. The optical probe device 70 has an optical probe (bundle fiber) 71, which is an insertion section inserted through the channel for inserting a treatment tool of the endoscope (not illustrated), a light source device 72 for supplying illumination light to the optical probe 71, and an image capturing device 73 for capturing the image of return lights from a subject, which are transferred by the optical probe 71.

The light source device 72 comprises a white light source 80, a collimator lens 81, an excitation light filter 82, and a condenser lens 83. At the condensing position of the condenser lens 83, the light entering end 84a of the light guide 84 is placed.

In this configuration, light from the white light source 80 provided in the light source device 72 is converted into roughly parallel beams by the collimator lens 81, then enter the excitation light filter 82. The excitation light filter 82 limits the band of the light from the white light source 80 to the light in the wavelength band of the excitation light. The light of which band is limited by the excitation light filter 82 are condensed by the condenser lens 83, and is incident on the light entering end 84a of the light guide 84.

The illumination light which is incident on the light entering end 84a are transmitted (guided) to the light emitting end 84b via the light guide 84. The light emitting end 84b of the light guide 84 is disposed in a ring shape at the outer circumference side of the optical probe 71, so as to surround the light entering end 86a of the later mentioned image guide 86.

At the light emitting end 84b, the illumination light filter 85 is provided in a ring shape matching the shape of the end face of the light emitting end 84b to serve as the illumination light filter section. And the illumination light emitted from the light emitting end 84b of the light guide 84 is irradiated onto the subject 21 via the illumination light filter 85.

The illumination light filter 85 transmits the wavelength band of the excitation light and shields fluorescence and Raman scattering light from the illumination light path. The illumination light filter 85 is made up of optical thin film (interference thin film) formed on the end face of the light emitting end 84b of the light guide 84. The illumination light filter 85 may be a substrate 85b, on which optical thin film (interference thin film) is formed, constructed to be attached to the end face of the light emitting end 84b of the light guide 84, as shown in FIG. 52.

The reflected lights, which are return lights from the subject 21 or fluorescence generated by irradiation of excitation light, are incident on the light entering end 86a of the image guide 86. The return lights which are incident on the light entering end 86a are transmitted (guided) to the light emitting end 86b by the image guide 86.

The image capturing device 73 comprises a condenser lens 87, excitation light cut filter 88 and image capturing section 89. And the light emitting end 86b of the image guide 86 is fixed inside the image capturing device 73.

In this configuration, light emitted from the light emitting end 86b of the image guide 86 is condensed onto the image capturing face (light receiving face) of the image capturing section 89 (fluorescent image capturing section) for capturing the fluorescent image via the excitation light cut filter 88 by the condenser lens 87 facing the light emitting end 86b. The excitation light cut filter 88 here has an optical characteristic to transmit the wavelength band of fluorescence generated from the subject 21, and cut (shield) the other wavelength bands.

The image capturing section 89 is electrically connected to an image generation device similar to those described in Embodiments 1 to 5, via a signal cable, which is not illustrated. The image capturing section 89 outputs the image capturing signal, acquired by photoelectric conversion, to this image generation device. The image generation device processes the image capturing signal from the image capturing section 89, and generates the image signal (video signal) of the fluorescent images. Also the image generation device processes image capturing signal from the image capturing section installed in the endoscope, and generates the image signal (video signal) of the endoscope image by normal visible light.

The image signal (video signal) of the fluorescent image and image signal (video signal) of the endoscopic image are output from the image generation device to a monitor, which is not illustrated, and a synthesized image of the normal image and fluorescent image is displayed on the display screen of the monitor. The excitation light filter 82, the illumination light filter 85, and the excitation light cut filter 88 here have filter characteristics similar to those described in Embodiments 1 to 5 according to the fluorescent images to be acquired (infrared fluorescent image or visible light fluorescent image).

By this, the optical probe device 70 can shield and decrease the fluorescence or Raman scattering light from the illumination light path. As a result, in the optical imaging device in Embodiment 6, both the image signal (video signal) of the endoscopic image by normal visible light and the fluorescent image can be acquired by combining the optical probe device 70 with the endoscope, and inserting the optical probe 71 into the channel for inserting a treatment tool of the endoscope.

Therefore the optical imaging device of Embodiment 6 can be used for both the fluorescence observation and normal endoscopic observation, and can decrease the fluorescence and Raman scattering light from the illumination light path.

The illumination light filter section provided at the end face of the optical probe 71 may be combined with the light receiving filter section to be one optical filter, and this optical filter may be installed at the end face of the optical probe 71. In other words, as FIG. 53 shows, an optical filter 91 is constituted of an illumination light filter 91a, which is provided at the end face of the light emitting end 84b of the light guide 84, and an excitation light cut filter 91b, which is provided at the end face of the light entering end 86a of the image guide 86. If this configuration is used, the excitation light cut filter 88 need not be provided in the image capturing device 73. The illumination light filter 91a may be configured to transmit only the wavelength band of excitation light, so as to also serve as the excitation light filter 82.

As FIG. 54 shows, the optical filter 92 has illumination light filters 92a in two sectors facing each other when the circular end face of the optical probe 71 is equally sectioned into four in the circumference direction. However, in the case of the configuration where the illumination light filter is provided in a ¼ sector alternately, the light emitting end 84b of the light guide 84 and light entering end 86a of the image guide 86 are also placed in a ¼ sector alternately on the end face of the optical probe 71. In this configuration as well, the excitation light cut filter may be provided in the light entering face of the image guide 86 (that is, the portion where the illumination light filter 92a of the optical filter 92 is not installed), although this is not illustrated.

As FIG. 55 shows, the optical filter 93 has a configuration where the illumination light filter 93a and excitation light cut filter 93b are provided in half of the end face of the optical probe 71 respectively. In the case of this configuration, however, the light emitting ends 84b of the light guide 84 and the light incident ends 86a of the image guide 86 are also placed in half of the end face of the optical probe 71 respectively.

As FIG. 56 shows, the optical filter 94 has a configuration where the illumination light filters 94a are provided alternately or in a checkered pattern on the end face of the optical probe 71. In the case of this configuration, however, the light emitting ends 84b of the light guide 84 and the light incident ends 86a of the image guide 86 are also placed alternately or in a checkered pattern. The excitation light cut filter may be provided on the light entering end face of the image guide 86, although this is not illustrated.

The optical filters described in FIG. 53 to FIG. 56 can be used for both infrared fluorescence observation and visible light fluorescence observation.

Embodiment 7

Figure 57:
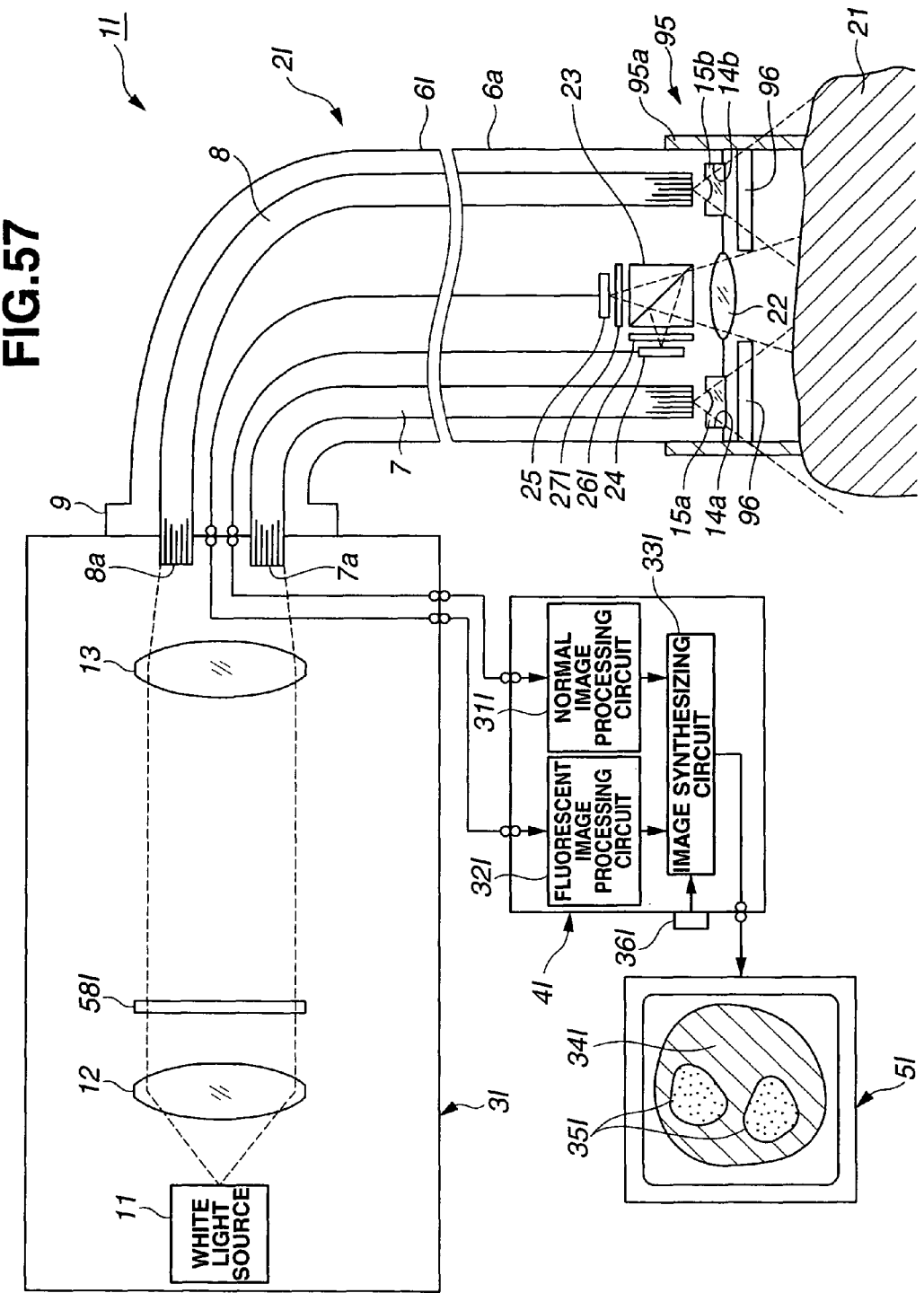
FIG. 57 is a diagram depicting an entire configuration of the optical imaging device according to Embodiment 7.
Figure 58:
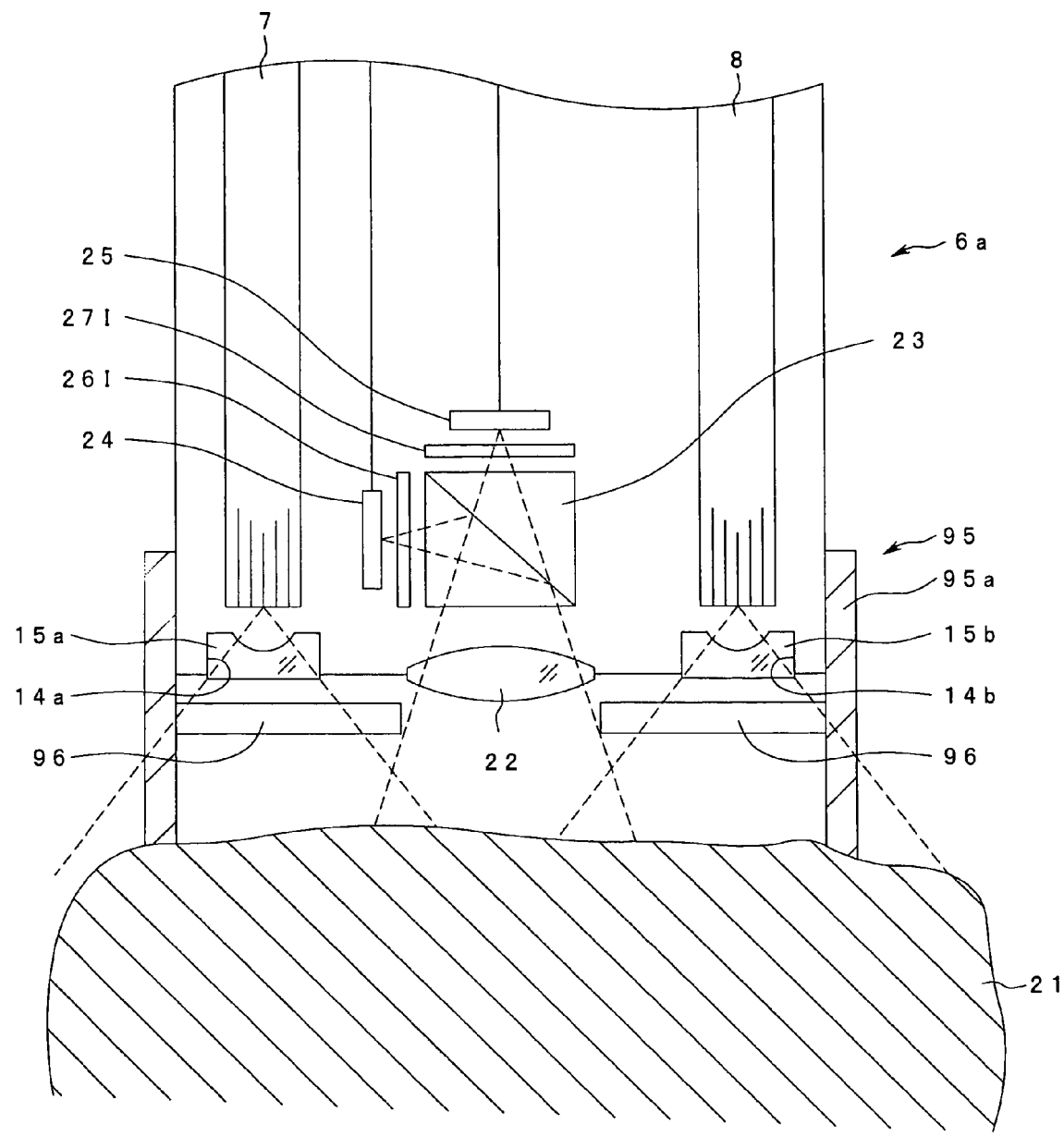
FIG. 58 is an enlarged view depicting a key section at the distal portion of the insertion section of the endoscope shown in FIG. 57.
Figure 59:
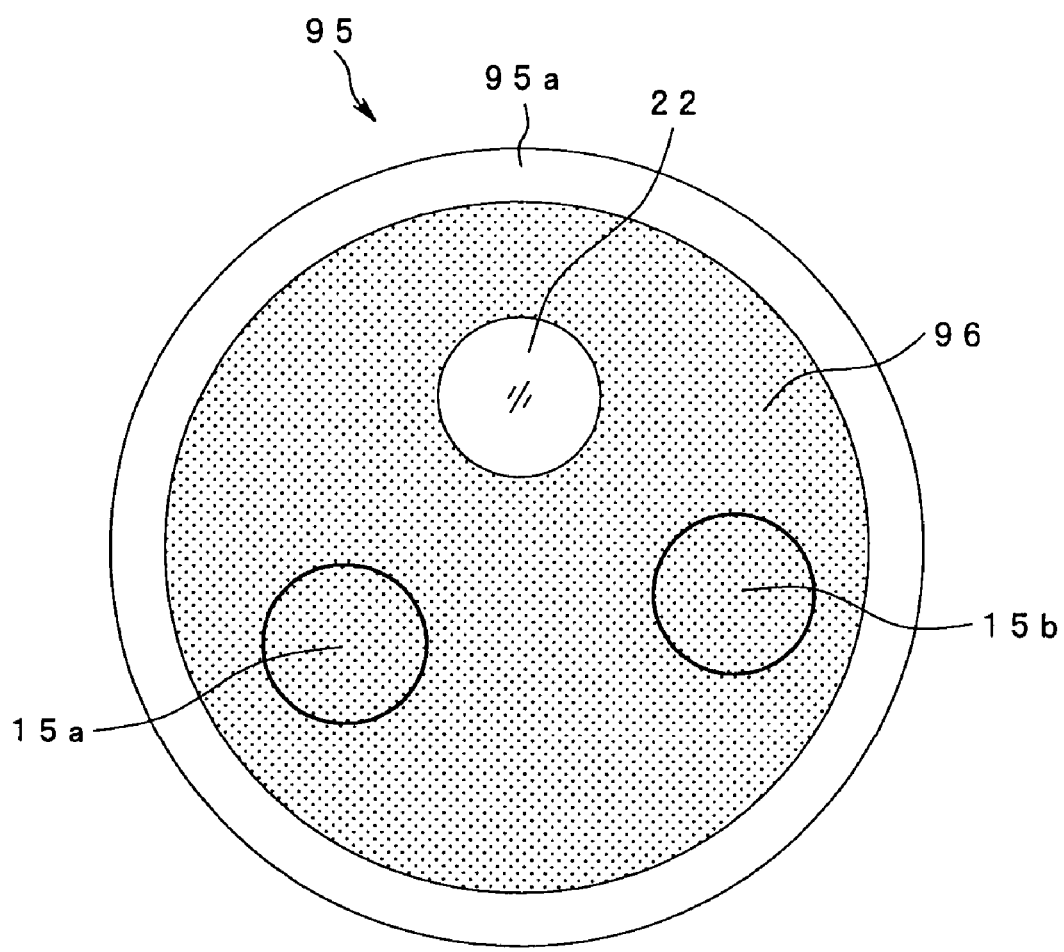
FIG. 59 is a front view depicting the distal portion of the insertion section shown in FIG. 58.
Figure 60:
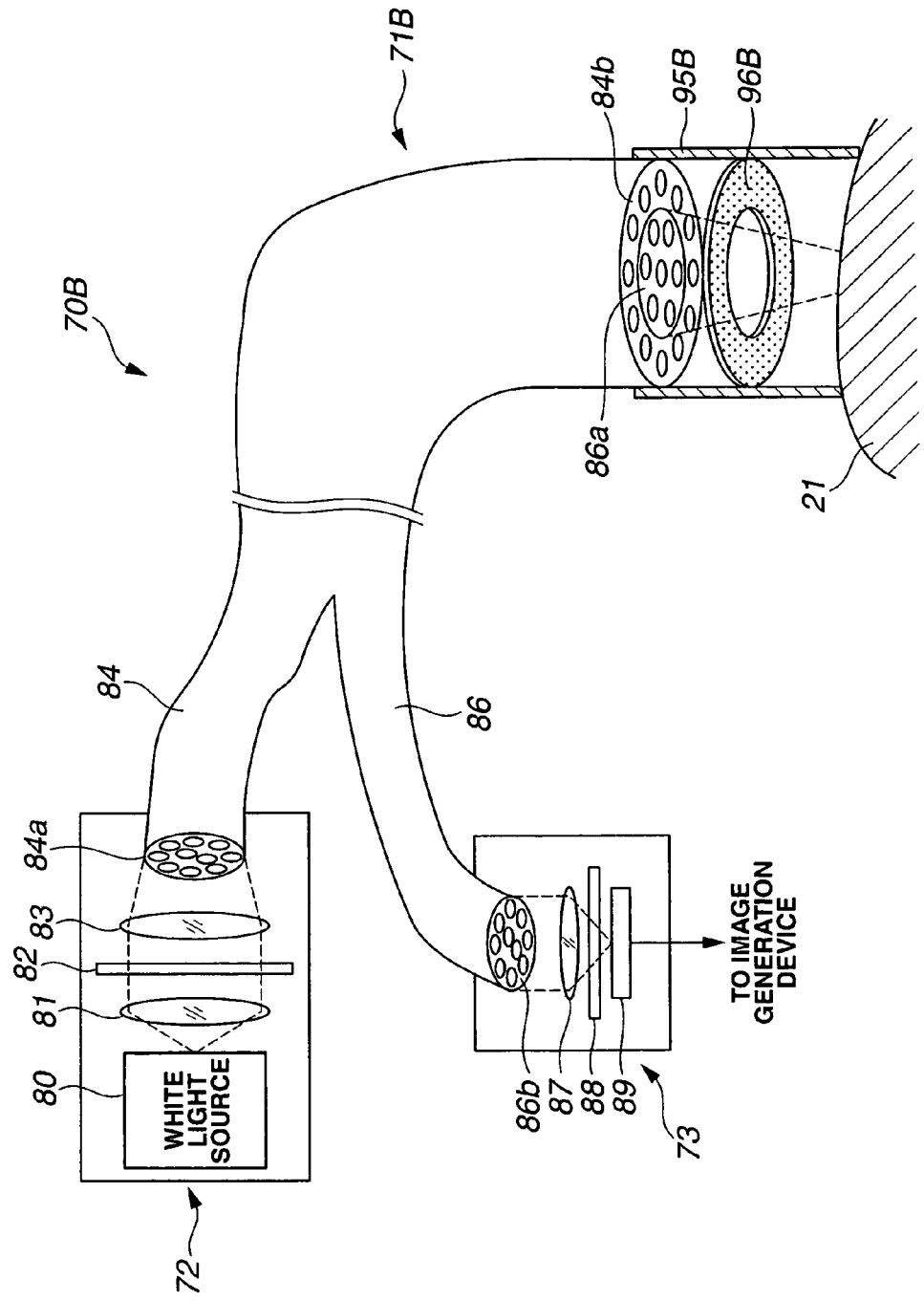
FIG. 60 is a diagram depicting an entire configuration of the optical probe device where a cap is installed at the tip of the probe.

FIG. 57 to FIG. 60 relate to Embodiment 7 of the present invention, where FIG. 57 is a diagram depicting an entire configuration of the optical imaging device according to Embodiment 7, FIG. 58 is an enlarged view depicting a key section at the distal portion of the insertion section of the endoscope shown in FIG. 57, FIG. 59 is a front view depicting the distal portion of the insertion section shown in FIG. 58, and FIG. 60 is a diagram depicting an entire configuration of the optical probe device where a cap is installed at the tip of the probe.

Embodiment 7 has a configuration where an illumination light filter is provided in a cap which can be removably attached to the distal portion of the insertion section. The rest of the configuration is roughly the same as Embodiment 1, therefore description thereof is omitted, and the same components are described denoting the same reference symbols.

As FIG. 57 to FIG. 59 show, an optical imaging device 1I of Embodiment 7 has a cap 95 which is freely removably attached to the distal portion 6a of the insertion section 6I of the endoscope 2I. In this cap 95, an illumination light filter 96 as the illumination light filter section, is installed at a position which faces the illumination lenses 15a and 15b of an endoscope 2I when the cap is attached to the distal portion 6a.

Specifically, this illumination light filter 96 is placed so as to cover the portion other than the objective lens 22, which is a light receiving window, as shown in FIG. 59. And this illumination light filter 96 has a filter characteristic similar to those described in Embodiments 1 to 5 according to the fluorescent image to be acquired (infrared fluorescent image or visible light fluorescent image). A cap main unit 95a may be made up of a light shielding element or a transparent element.

A light source device 3I has an interference filter 58I as the guided light filter section. The interference filter 58I has a filter characteristic similar to those described in Embodiments 1 to 5 according to the fluorescent image to be acquired (infrared fluorescent image or visible light fluorescent image).

By this, the band of light from the white light source 11 is limited to the wavelength band of the visible light and the wavelength band of excitation light, then the light is condensed by the condenser lens 13 and is incident on the light incident ends 7a and 8a of the light guides 7 and 8. The illumination light which is incident on these light incident ends 7a and 8a are transmitted (guided) to each emitting end via the light guides 7 and 8. The illumination light emitted from the light emitting ends of the light guides 7 and 8 spread via the illumination lenses 15a and 15b facing each light emitting end respectively, and are irradiated onto the subject 21 via the illumination light filter 96 installed in the cap 95.

At this time, the illumination light filter 96 transmits the wavelength band of the excitation light from the light irradiated from the endoscope 2I to the subject 21, and shields fluorescence or Raman scattering light from the illumination light path. Since the fluorescence or Raman scattering light from the illumination light path is shielded, reflected light or fluorescence generated by the irradiation of excitation light is incident on the objective lens 22 as return lights from the subject 21.

The return lights from the subject 21 are incident on the objective lens 22 and are split into two by the beam splitter 23. Out of the lights split by the beam splitter 23, the reflected light is formed into an image at the image capturing section 24 via a visible light filter 26I, and transmitted light is formed into an image in the image capturing section 25 via an excitation light cut filter 27I. The visible light filter 26I or excitation light cut filter 27I has a filter characteristic similar to those described in Embodiments 1 to 5 according to the fluorescent image to be acquired (infrared fluorescent image or visible light fluorescent image).

The information of the light received by the image capturing section 24 is output to a monitor 5I as a normal image via a normal image processing circuit 31I and image synthesizing circuit 33I of an image generation device 4I. The information of the lights received by the image capturing section 25 is output to the monitor 5I as a fluorescent image via the fluorescent image processing circuit 32I and image synthesizing circuit 33I. In this way, a synthesized image of a normal image 34I and a fluorescent image 35I is displayed on the display screen of the monitor 5I as one display image.

The image generation device 4I, by the select operation of the display select switch 36I, may switch a state where the normal image 34I is displayed on the display screen of the monitor 5I without image synthesis processing by the image synthesizing circuit 33I, a state where the fluorescent image 35I is displayed on the display screen of the monitor 5I without image synthesis processing by the image synthesizing circuit 33I, and a state where the image synthesizing circuit 33I performs image synthesis processing and a synthesized image of the normal image 34I and fluorescent image 35I is displayed (or displayed side by side) on the display screen of the monitor 5I.

As a result, the optical imaging device 1I of Embodiment 7 can exhibit effects similar to Embodiments 1 to 5, and can decrease (or shield) fluorescence and Raman scattering lights from the illumination light path in the lights irradiated from the endoscope 2I to the subject 21 merely by performing a simple operation of attaching a cap 95 to the distal portion 6a of the insertion section 6I.

In the optical imaging device 1I of Embodiment 7, the cap 95 can be freely removably attached, so illumination light filters 96, which can support various wavelengths, can be provided according to the fluorescent image to be acquired (infrared fluorescent image or visible light fluorescent image).

The above mentioned cap may be used for the optical probe device described in Embodiment 6.

In other words, the optical probe device 70B shown in FIG. 60 has a cap 95B that can be removably attached to the tip of an optical probe 71B. In this cap 95B, an illumination light filter 96B as the illumination light filter section, instead of the above mentioned illumination light filter 85, is installed in the position facing the light emitting end 84b of the light guide 84 when the cap 95B is attached to the tip of the optical probe 71B.

The illumination light filter 96B is disposed in a ring shape, so as to cover the light emitting end 84b of the light guide 84, and has a filter characteristic similar to those described in Embodiments 1 to 5 according to the fluorescent image to be acquired (infrared fluorescent image or visible light fluorescent image). The illumination light filter 96B may be made up of an optical filter having a configuration similar to Embodiment 6. The rest of the configuration is similar to that of Embodiment 6, so description thereof is omitted. By this, the optical probe device 70B can shield and decrease fluorescence or Raman scattering lights from the illumination light path.

Embodiment 8

Figure 61:
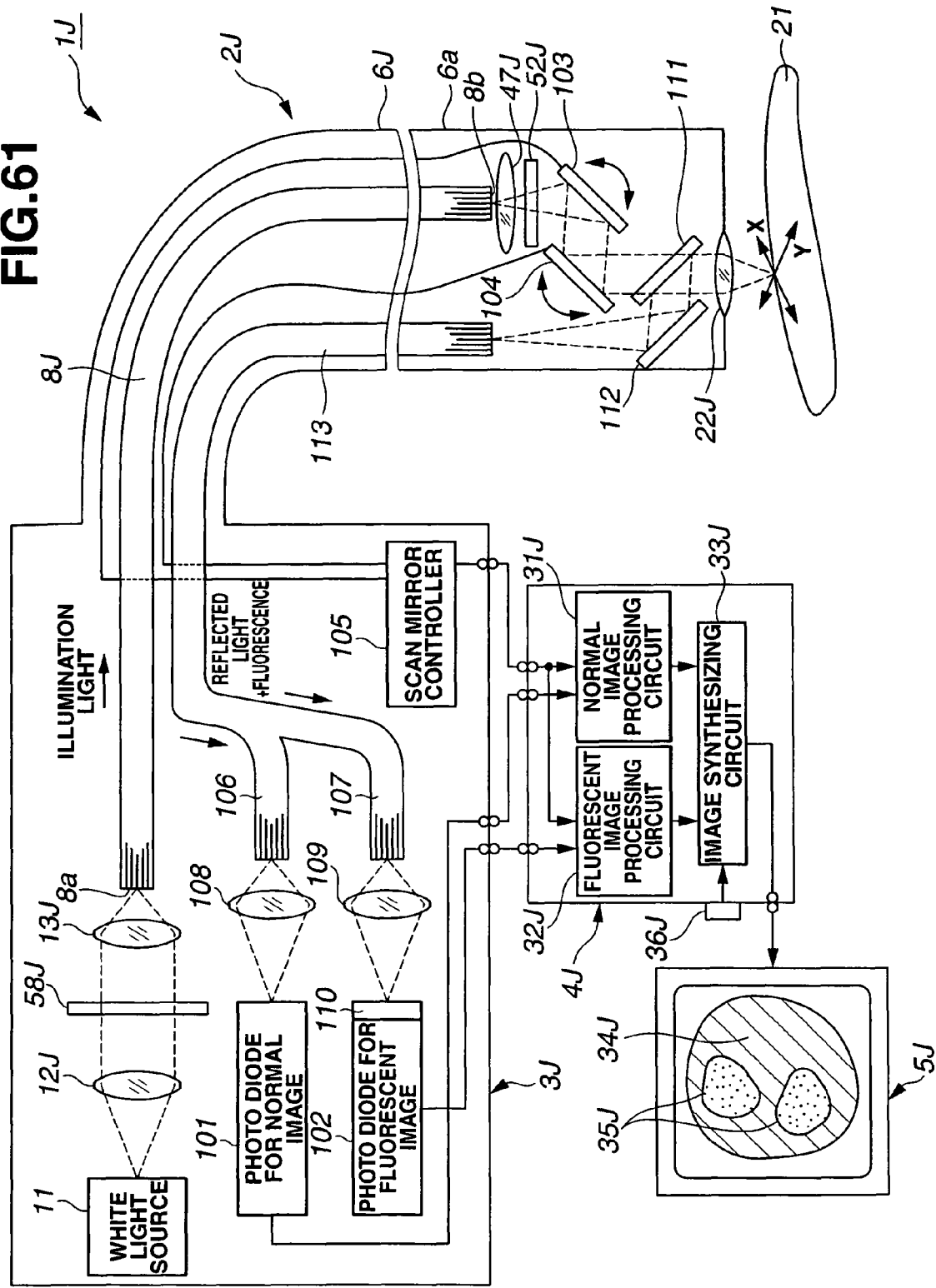
FIG. 61 is a diagram depicting an entire configuration of the optical imaging device according to Embodiment 8.

FIG. 61 is a diagram depicting an entire configuration of the optical imaging device according to Embodiment 8.

Embodiment 8 is the present invention applied to an optical scanning type optical imaging device. The rest of the configuration is roughly the same as Embodiment 1, therefore description thereof is omitted, and the same components are described denoting with the same reference symbols.

As FIG. 61 shows, an optical imaging device 1J of Embodiment 8 comprises a light source device 3J which has a photodiode 101 for a normal image and a photodiode 102 for a fluorescent image, instead of the image capturing section 24 for capturing a normal image and image capturing section 25 for capturing a fluorescent image, and an endoscope 2J which extends from the light source device 3J.

In the insertion section 6J of the endoscope 2J, a light guide 8J for guiding the lights supplied from the light source device 3 to the distal end of the insertion section 6J has been inserted. The light guide 8J can be either a single mode optical fiber or multi-mode optical fiber.

Light from a white light source 11 provided inside the light source device 3J is converted into roughly parallel beams by a collimator lens 12J, then condensed by a condenser lens 13J via an interference filter 58J, and is incident on the light entering end 8a of the light guide 8J. The illumination light which is incident on the light entering end 8a are transmitted (guided) to the light emitting end 8b via the light guide 8J.

The illumination light (excitation light+white light) emitted from the light guide 8J is incident on an illumination light filter 52J via a relay lens 47J. The illumination light filter 52J has a filter characteristic similar to those described in Embodiments 1 to 7 according to the fluorescent image to be acquired (infrared fluorescent image or visible light fluorescent image).

The light which has passed through the illumination light filter 52J is two-dimensionally scanned by an X axis scanning mirror 103 and a Y axis scanning mirror 104. The X axis scanning mirror 103 is configured so as to rotate around a predetermined axis. The Y axis scanning mirror 104 is configured so as to rotate around an axis perpendicular to the rotation axis of the X axis scanning mirror 103. These scanning mirrors 103 and 104 are controlled by a scan mirror controller 105 installed in the light source device 3J.

The illumination light (excitation light+white light) which has been two-dimensionally scanned by the X axis scanning mirror 103 and the Y axis scanning mirror 104 pass through a half mirror 111, then are irradiated onto the subject 21 via an objective lens 22J which also serves as an illumination lens.

By this configuration, the illumination light (excitation light+white light) two-dimensionally scan a predetermined observation area on the subject 21 after self fluorescence components are decreased.

Return lights (fluorescence+reflected white light) from the subject 21 are incident on the half mirror 111 via the objective lens 22J. The return lights reflected by the half mirror 111 are reflected again by a mirror 112, then guided to an image guide 113 which has been inserted through the insertion section 6J of the endoscope 2J. The image guide 113 can be either a single mode optical fiber or a multi-mode optical fiber. One end of the image guide 113 is inserted into the light source device 3J, and branched into a normal branch path 106 which reaches the photodiode 101 for normal image and a fluorescent branch path 107 which reaches the photodiode 102 for fluorescent image in the light source device 3J. A part of the return lights which entered the image guide 113 is guided to the emitting end of the normal branch path 106 and the rest is guided to the emitting end of the fluorescent branch path 107. By this configuration, the half mirror 111 and objective lens 22J serve as both the illumination optical system and light receiving optical system.

The return lights (fluorescence+reflected white light) emitted from the emitting end of the normal branch path 106 are received by the photodiode 101 for normal image via the collimator lens 108, and the intensity thereof is converted into a voltage value.

The return lights (fluorescence+reflected white light) emitted from the emitting end of the fluorescent branch path 107 are received by the photodiode 102 for fluorescent image via the collimator lens 109, and the intensity thereof is converted into a voltage value. The excitation light cut filter 110 is placed between the collimator lens 109 and the photodiode 102 for fluorescent image. The excitation light cut filter 110 has a filter characteristic similar to those described in Embodiments 1 to 7 according to the fluorescent image to be acquired (infrared fluorescent image or visible light fluorescent image).

Signal from the photodiode 101 for normal image is input to a normal image processing circuit 31J provided in the image generation device 4J. Signal from the photodiode 102 for fluorescent image is input to a fluorescent image processing circuit 32J provided in the image generation device 4J. Synchronizing with the signal from the photodiode 101 for normal image and photodiode 102 for fluorescent image, the scan mirror controller 105 sends mirror angle information of the X axis scanning mirror 103 and Y axis scanning mirror 104 to the normal image processing circuit 31J and fluorescent image processing circuit 32J.

The normal image processing circuit 31J and fluorescent image processing circuit 32J perform processing for generating a normal image and fluorescent image according to the mirror angle information of the X axis scanning mirror 103 and Y axis scanning mirror 104.

The image signal (video signal) of the normal image and image signal (video signal) of the fluorescent image, generated by the normal image processing circuit 31J and fluorescent image processing circuit 32J respectively, are output to the monitor 5J via the image synthesizing circuit 33J for synthesizing images. By this, a synthesized image of the normal image 34J and fluorescent image 35J, for example, is displayed on the display screen of the monitor 5J. The fluorescent image 35J and normal image 34J are images that are two-dimensionally scanned by the X axis scanning mirror 103 and Y axis scanning mirror 104, which are identical scanning means, scanning area and scanning timing thereof are identical. Therefore the image synthesizing circuit 33J can compose the normal image and fluorescent image at a same timing.

The image generation circuit 4J, by the select operation of the display select switch 36J, may switch a state where the normal image 34J is displayed on the display screen of the monitor 5J without image synthesis processing by the image synthesizing circuit 33J, a state where the fluorescent image 35J is displayed on the display screen of the monitor 5J without image synthesis processing by the image synthesizing circuit 33J, and a state where the image synthesizing circuit 33J performs image synthesis processing, and a synthesized image of the normal image 34J and fluorescent image 35J is displayed (or displayed side by side) on the display screen of the monitor 5J.

In the above description, the illumination light filter 52J is provided between the relay lens 47J and the X axis scanning mirror 103, but the present invention is not limited to this, but the illumination light filter 52J may be provided in another section if it is on the illumination light path and where the return lights from the subject do not pass. Therefore the illumination light filter 52J can be provided in any position between the light emitting end 8b of the light guide 8J and the light emitting face of the half mirror 111. For example, an optical thin film may be formed on the surface of the half mirror 111 at the Y axis scanning mirror 104 side, so that the half mirror 111 itself can also serve as the illumination light filter 52J.

In the optical imaging device 1J of Embodiment 8, the illumination light filter 52J is provided in a portion on the illumination light path where the return lights from the subject do not pass, so just like Embodiments 1 to 7, fluorescence or Raman scattering light from the illumination light path can be decreased, and the generation of light to be the source of noise can be suppressed even if this optical imaging device 1J is an optical scanning type.

Experiment Results

Figure 62:
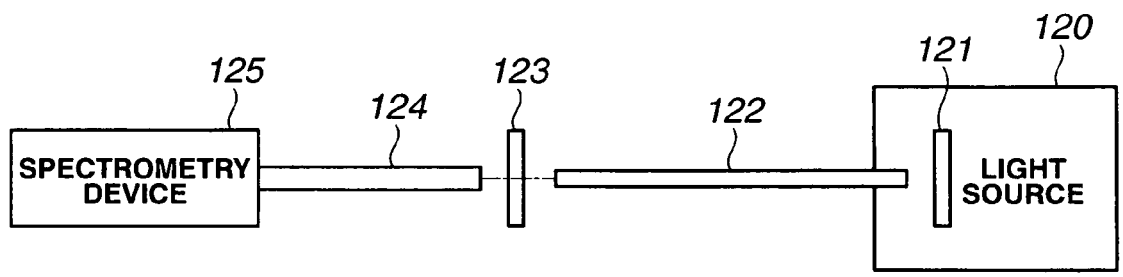
FIG. 62 is a diagram depicting the outline of the measurement system according to each embodiment.
Figure 64:
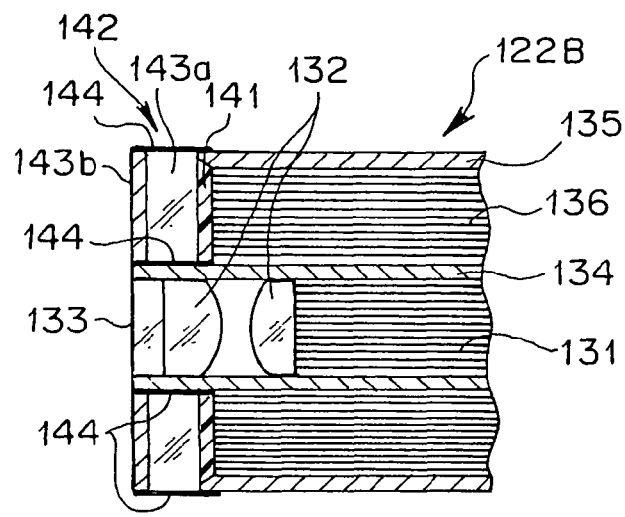
FIG. 64 is a sectional view depicting the configuration of the distal portion of the endoscope where the illumination light filter is installed according to each embodiment.
Figure 65:
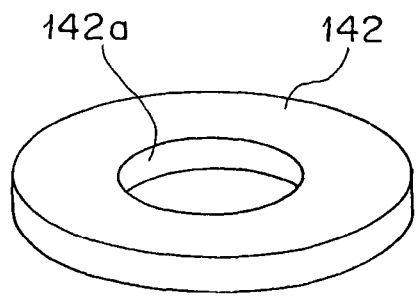
FIG. 65 is a perspective view depicting the configuration of the illumination light filter according to each embodiment.
Figure 66:
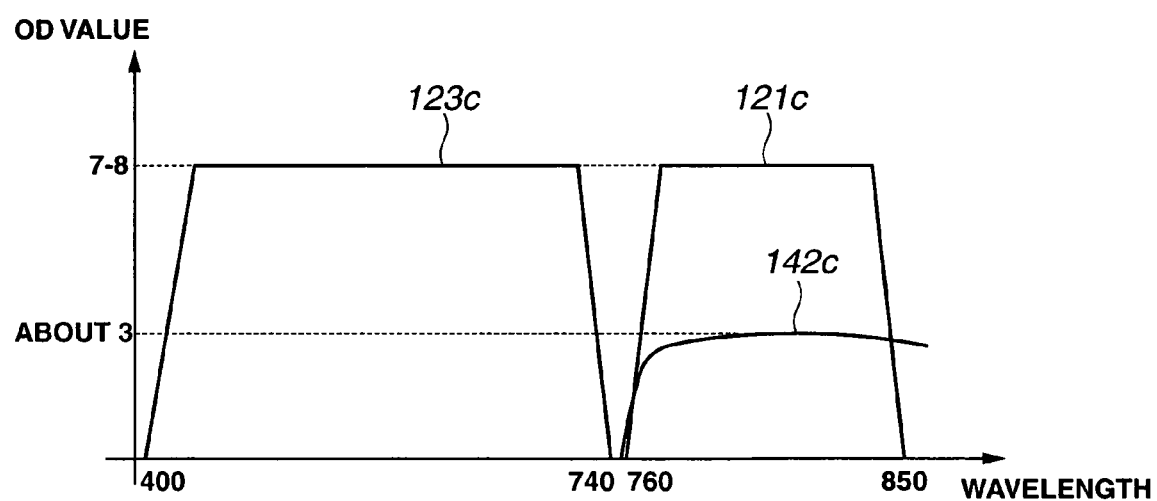
FIG. 66 is a graph depicting the filter characteristic of the illumination light filter, excitation light filter and excitation light cut filter according to each embodiment.
Figure 67:
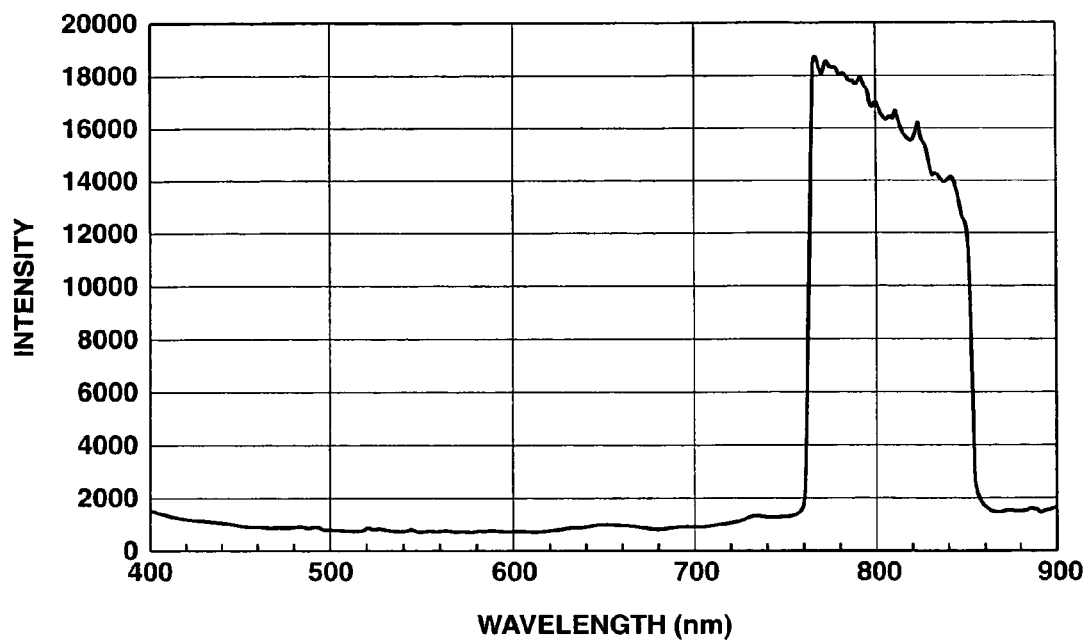
FIG. 67 is a diagram depicting the band characteristic of lights which have passed through the illumination light path of the endoscope where the illumination light filter is not installed according to the related art.
Figure 68:
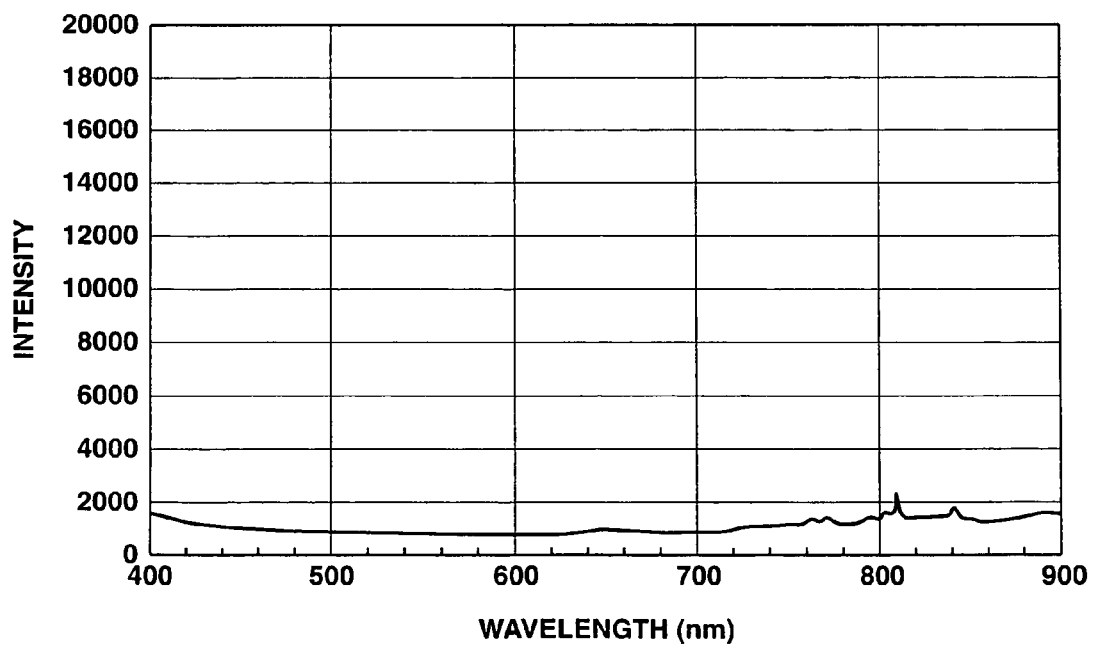
FIG. 68 is a diagram depicting the band characteristic of lights which have passed through the illumination light path of the endoscope where the illumination light filter is installed according to each embodiment.
Figure 69:
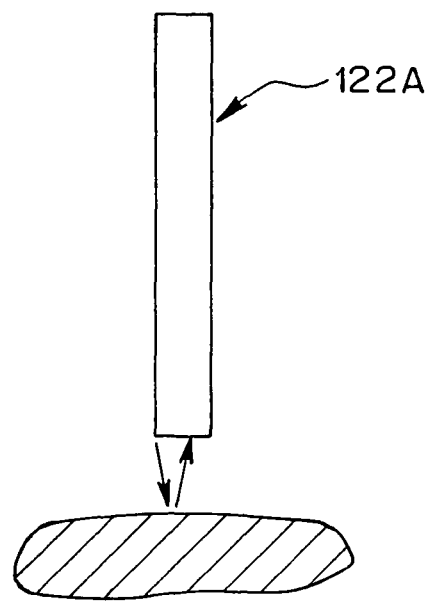
FIG. 69 is a diagram depicting the status when the subject is being illuminated and image thereof is being captured by the endoscope where the illumination light filter is not installed according to the related art.
Figure 70:
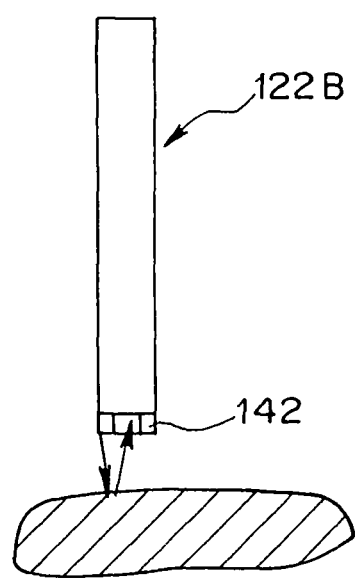
FIG. 70 is a diagram depicting the status where the subject is being illustrated and image thereof is being captured by the endoscope where the illumination light filter is installed according to each embodiment.
Figure 71:
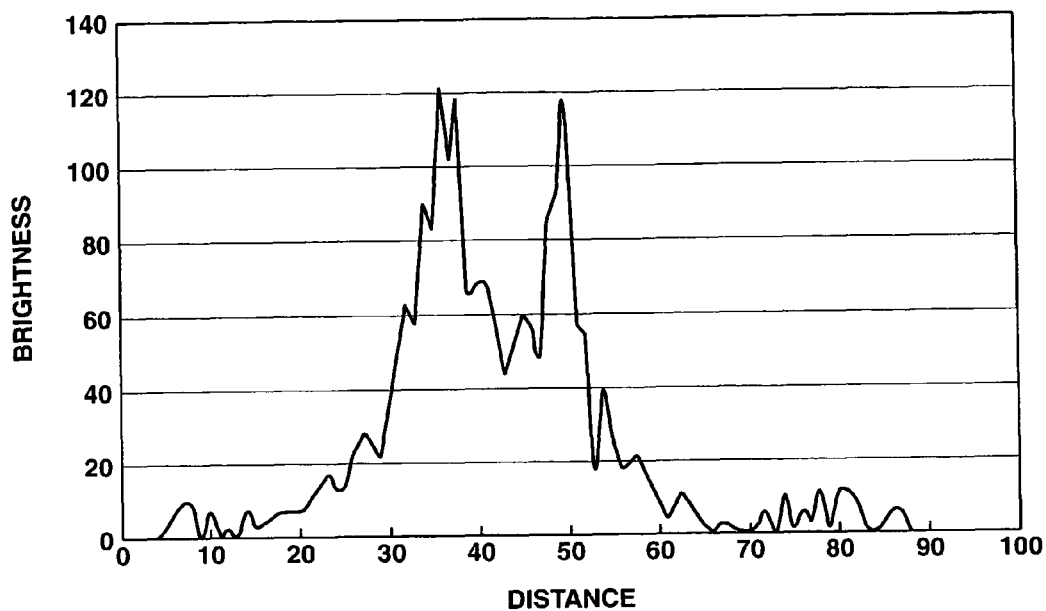
FIG. 71 is a diagram depicting the brightness distribution of one vertical line passing through the high brightness portion near the center in the image captured by irradiating the subject using the endoscope where the illumination light filter is not provided.
Figure 72:
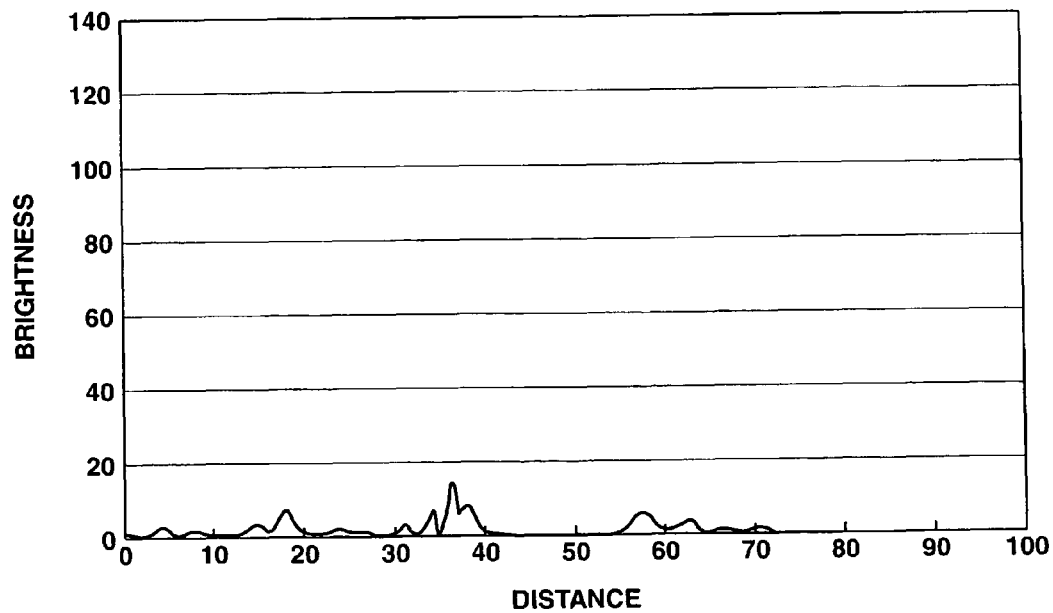
FIG. 72 is a diagram depicting the brightness distribution of the same line as FIG. 71 in the image captured by irradiating the subject using the endoscope where the illumination light filter is provided according to each embodiment.

Now the state of fluorescence or Raman scattering light generated on the illumination light path and reduction effect by using the illumination light filter will be described with reference to FIG. 62 to FIG. 72. Here FIG. 62 is a diagram depicting an outline of the configuration measurement system, FIG. 63 is a sectional view depicting the configuration of the distal portion of the endoscope where the illumination light filter is not provided, FIG. 64 is a sectional view depicting the configuration of the distal portion of the endoscope where the illumination light filter is provided, FIG. 65 is a perspective view depicting the configuration of the illumination light filter, FIG. 66 is a graph depicting the filter characteristic of the illumination light filter, excitation light filter and excitation light cut filter, FIG. 67 is a diagram depicting the band characteristic of light which is passed through the illumination light path of the endoscope where the illumination light filter is not provided, FIG. 68 is a diagram depicting the band characteristic of light which is passed through the illumination light path of the endoscope where the illumination light filter is provided, FIG. 69 is a diagram depicting the status when the subject is being illuminated and the image thereof is being captured by the endoscope where the illumination light filter is not provided, FIG. 70 is a diagram depicting the status where the subject is being illustrated and the image thereof is being captured by the endoscope where the illumination light filter is provided, FIG. 71 is a diagram depicting the brightness distribution of one vertical line passing through the high brightness portion near the center in the image captured by irradiating the subject using the endoscope where the illumination light filter is not provided, and FIG. 72 is a diagram depicting the brightness distribution of the same line as FIG. 71 in the image captured by irradiating the subject using the endoscope where the illumination light filter is provided.

Here the experiment result will be described using the endoscope as an example, but this experiment result can also be applied to an optical probe.

This measurement system comprises a light source 120 for supplying illumination light to an endoscope 122 in an inspection target, and a spectrometry device 125 for receiving illumination light irradiated from the endoscope 122 using a light receiving fiber 124 via an excitation light cut fiber 123 and performing spectrometry on the received light. In the light source 120, an excitation light filter 121 is provided.

Figure 63:
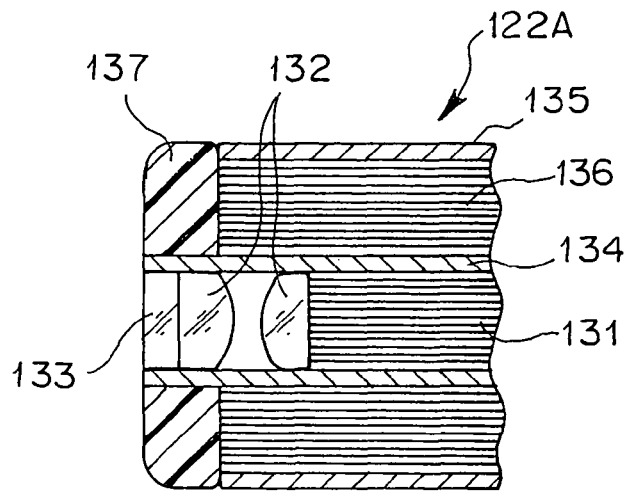
FIG. 63 is a sectional view depicting the configuration of the distal portion of the endoscope where the illumination light filter is not installed according to the related art.

A distal portion of the endoscope 122A, where the illumination light filter is not provided, is configured as shown in FIG. 63. In other words, the endoscope 122A is circular in a cross-section perpendicular to the insertion axis, and the image guide 131 is provided at the center of this cross-section. The image guide 131 is surrounded with a coating 134 made of light shielding material. At the tip of the image guide 131, an objective optical system 132 is provided. And at the tip of the objective optical system 132, a cover glass 133 is installed. A light guide 136 is provided outside the coating 134 so that the cross-section perpendicular to the insertion axis is a ring shape. The outside of the light guide 136 is coated with a light shielding outer shell 135, and the tip thereof is fixed by a transparent adhesive 137.

The distal portion of an endoscope 122B, where the illumination light filter is provided, on the other hand, is configured as shown in FIG. 64. The configuration of the image guide 131, objective optical system 132, cover glass 133, coating 134, outer shell 135 and light guide 136 is the same as that of the endoscope 122A shown in FIG. 63. At the tip of the light guide 136, an illumination light filter 142 is bonded with translucent adhesive 141. The illumination light filter 142 is comprised of a filter substrate 143a and an optical thin film 143b formed on the emitting side end face of the filter substrate 143a. The illumination light filter 142 is made up of a ring, where a circular hole 142a is formed for passing beams that is incident from the subject side to the objective optical system 132, as shown in FIG. 65. The inner circumference side and outer circumference side of the illumination light filter 142 are secured to the endoscope 122B with black adhesive for shielding light 144.

Now the characteristic of each optical filter provided in the measurement system shown in FIG. 62 will be described with reference to FIG. 66.

In FIG. 66, a reference symbol 121c indicates the filter characteristic of an excitation light filter 121 provided in the light source 120. The excitation light filter 121 has a filter characteristic to decrease the wavelength band 760 to 850 nm of near infrared by an OD value of about 7 to 8 (substantially shields light), as shown in FIG. 66. Therefore light that is incident on the endoscope 122 do not substantially include light in this wavelength band.

A reference symbol 123c indicates the filter characteristic of an excitation light cut filter 123 provided on an optical path from the endoscope 122 to the spectrometry device 125. This excitation light cut filter 123 has a filter characteristic to decrease the wavelength band 400 to 740 nm of visible light by an OD value of about 7 to 8 (substantially shields light), as shown in FIG. 66. Therefore light to be measured by the spectrometry device 125 do not substantially include the light in this wavelength band.

And the reference symbol 142c indicates the filter characteristic of the illumination light filter 142 provided at the distal portion of the endoscope 122. The illumination light filter 142 has a filter characteristic to decrease the wavelength band of 760 nm or more of infrared by an OD value of about 3 using the characteristic of the optical thin film 143b.

FIG. 67 shows the acquired result when the band characteristic of the light transmitted through the illumination light path of the endoscope 122A, where the illumination light filter shown in FIG. 63 is not installed, is measured using the measurement system having this configuration.

As FIG. 67 shows, in the wavelength band 760 to 850 nm of near infrared, the peaks of intensity of received light are seen. The light in this wavelength band has already been substantially shielded by the excitation light filter 121 in the light source 120, so the peaks shown in FIG. 67 are the fluorescence or Raman scattering light generated from the illumination light path.

FIG. 68, on the other hand, shows the acquired result when the band characteristic of the light transmitted through the illumination light path of the endoscope 122B, where the illumination light filter 142 shown in FIG. 64 and FIG. 65 is provided, is measured using the above mentioned measurement system.

The peaks of the intensity of the light in the wavelength band 760 to 850 nm of near infrared shown in FIG. 67 considerably drop in FIG. 68, and decrease to the level which does not substantially affect the measurement result. Therefore it is clear that by providing the illumination light filter 142, fluorescence or Raman scattering light from the illumination light path can be sufficiently decreased.

FIG. 69 shows a status of the image when a sample is irradiated by the endoscope 122A, where the illumination light filter shown in FIG. 63 is not provided, and the optical image of the sample is transmitted via the image guide 131 and is captured by the image capturing section.

FIG. 70 shows a status of the image when the sample is irradiated by the endoscope 122B, where the illumination light filter 142 shown in FIG. 64 and FIG. 65 is provided, and the optical image of the sample is transmitted via the image guide 131 and is captured by the image capturing section.

In the positional relationship of the endoscopes 122A and 122B and the sample when the image is captured in the arrangement shown in FIG. 69 and FIG. 70, the distance between the center of the solid portion of the ring shaped light guide 136 and the center of the image guide 131 is about 0.3 mm, and the distance between the distal end face of the endoscope 122A and 122B and the sample is about 1 to 1.5 mm. For the sample, a general flat portion of the surface inside the large intestines of a mouse, where fluorescence dye is not introduced, is used.

Since fluorescence dye has not been introduced into the sample, fluorescence is not supposed to be received by the image capturing section when the optical image of this sample is captured. However in the images captured via the endoscope 122A where the illumination light filter is not provided, shown in the configuration in FIG. 69, an image appears. This is because the above mentioned fluorescence or Raman scattering light from the illumination light are included in the illumination light, which are irradiated onto the sample, are reflected by the sample and received by the image capturing section. And a portion where brightness is particularly high in the image is a portion of regular reflection. FIG. 71 shows the brightness distribution along the vertical one line passing through the high brightness portion near the center in this image. As FIG. 71 shows, the brightness of the portion, which is presumed as regular reflection among the reflected lights from the sample, is particularly higher than the brightness of other portions of the reflected lights (e.g. about 60 to 120 in the brightness index in FIG. 71).

In the case of the image captured via the endoscope 122B where the illumination light filter 142 is provided, having the configuration in FIG. 70, on the other hand, the above mentioned fluorescence or Raman scattering light from the illumination light path are removed from the illumination light which are irradiated onto the sample. Therefore luminescent spots in the image are almost all gone in this image. FIG. 72 shows the brightness distribution along the same line as FIG. 71 in this image. As FIG. 72 shows, almost all the luminescent spots are gone in the image (e.g. less than 20 in the brightness index in FIG. 72).

In this way, it is clear that providing the illumination light filter 142 is very effective, particularly under the conditions where regular reflection could be generated.

Figure 73:
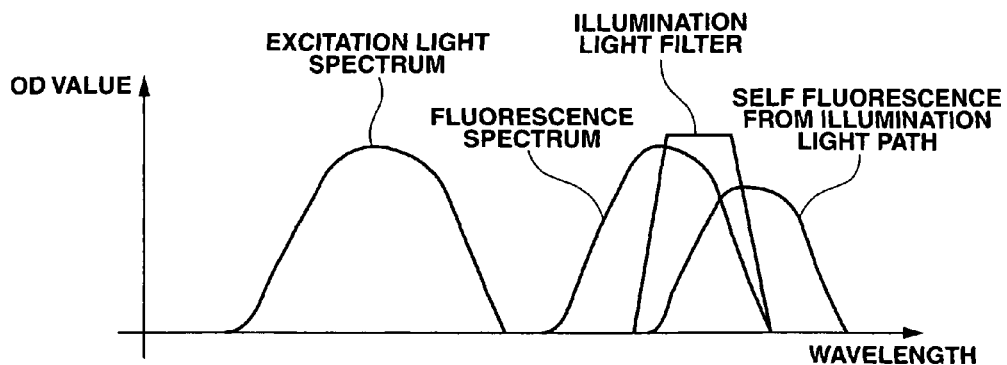
FIG. 73 is a graph depicting an example when the band characteristic of the illumination light filter is set so as to shield the overlapping portion of the fluorescence from the subject and self fluorescence according to each embodiment.

Now some examples of setting the band characteristic of the illumination light filter will be described with reference to FIG. 73 to FIG. 75. FIG. 73 is a graph depicting an example when the band characteristic of the illumination light filter is set so as to shield the overlapping portion of the fluorescence from the subject and self fluorescence, FIG. 74 is a graph depicting an example when the band characteristic of the illumination light filter is set so as to shield the overlapping portion of the transmission band of the excitation light cut filter and self fluorescence, and FIG. 75 is a graph depicting an example when the band characteristic of the illumination light filter is set so as to shield the overlapping portion of the transmission band of the excitation light cut filter and fluorescence from the subject.

In the illumination light filter shown in FIG. 73, the band characteristic is set so as to shield the overlapping portion of fluorescence of the subject and self fluorescence. If the optical imaging device is configured such that another filter shields the excitation light and self fluorescence, which cannot be shielded by the illumination light filter, then only fluorescence from the subject can be received, and the image can be captured without being affected by self fluorescence.

Figure 74:
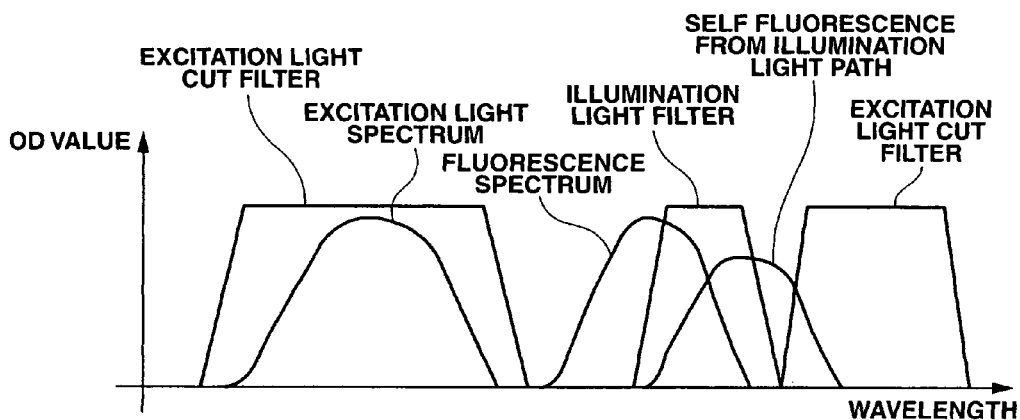
FIG. 74 is a graph depicting an example when the band characteristic of the illumination light filter is set so as to shield the overlapping portion of the transmission band of the excitation light cut filter and self fluorescence according to each embodiment.

In the illumination light filter shown in FIG. 74, the band characteristic is set so as to shield the overlapping portion of the transmission band of the excitation light cut filter and self fluorescence. By this, only the fluorescence from the subject in the transmission band of the excitation light cut filter can be received, and the image can be captured without being affected by the self fluorescence.

Figure 75:
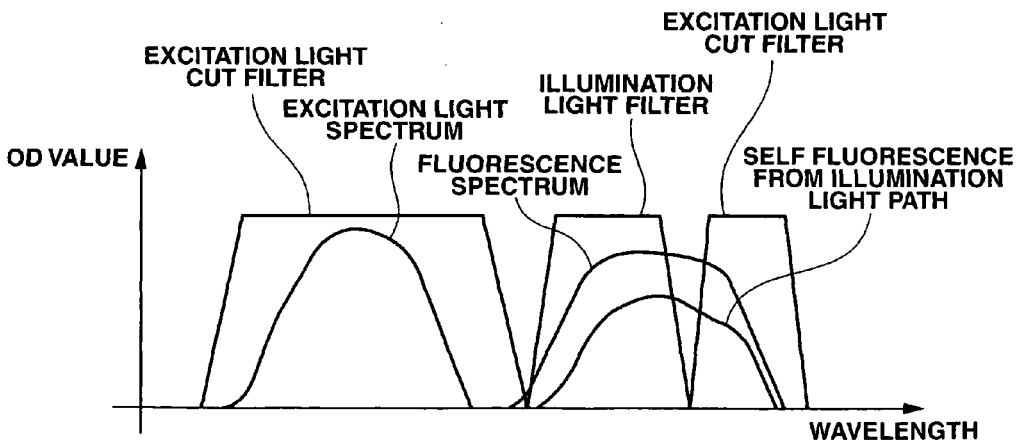
FIG. 75 is a graph depicting an example when the band characteristic of the illumination light filter is set so as to shield the overlapping portion of the transmission band of the excitation light cut filter and fluorescence from the subject according to each embodiment.

In the illumination light filter shown in FIG. 75, the band characteristic is set so as to shield the overlapping portion of the transmission band of the excitation light cut filter and fluorescence from the subject. By this, the light in the band captured by the image capturing section via the excitation light cut filter does not include light in the same band as the fluorescence from the subject. Therefore only the fluorescence from the subject can be received, and the image captured without being affected by light other than fluorescence from the subject.

As examples show, the illumination light filter is configured such that at lest light in the band overlapping the band of light captured by the image capturing section for capturing a fluorescent image is decreased from the light that is transmitted from the light source and is incident on the illumination light filter.

By constructing like this, fluorescence or Raman scattering light from the illumination light path affecting the fluorescent image captured by the image capturing section can be prevented.

The endoscope in the above mentioned embodiments may be either a so called flexible endoscope or a rigid endoscope. The above mentioned endoscope and optical probe may be for medical use, or may be for animals or industrial use.

The present invention is not limited to the above embodiments, but needles to say various modifications and applications are possible within the scope of the essential character of the invention. Embodiments implemented by partially combining each embodiment are therefore included in the present invention.

Additions

Addition 1

An optical imaging device, comprising: an insertion section that can be inserted into a body cavity; a light transmission section provided in the insertion section for guiding light from a light source including at least excitation light and light in a part of the visible light band into a subject in the body cavity; a light receiving optical system provided at a distal portion of the insertion section for receiving return lights from the subject; a light detection section for detecting the return lights received by the light receiving optical system; and an illumination light filter section secured in a path of the light transmission section or a light emitting end for at least decreasing fluorescence or Roman scattering light generated on an optical path of light which is transmitted from the light source and are emitted to the subject.

Addition 2

An optical imaging device, comprising: an insertion section that can be inserted into a body cavity; a light transmission section provided in the insertion section for guiding light from a light source into a subject in a the body cavity; a light receiving optical system provided at a distal portion of the insertion section for receiving return lights from the subject; light detection section for detecting the return lights received by the light receiving optical system; an illumination light guiding optical system for guiding light from the light source into the light transmission section; a guided light filter section provided in the illumination light guiding optical system for shielding lights in a predetermined wavelength band for the light from the light source; and an illumination light filter section provided in a path of the light transmission section or a light emitting end for shielding light in a predetermined wavelength band for light which is transmitted from the light source and are emitted to the subject.

Addition 3

An optical imaging device, comprising: an insertion section that can be inserted into a body cavity; a light transmission section provided in the insertion section for guiding light from a light source into a subject; a light receiving optical system provided at a distal portion of the insertion section for receiving return lights from the subject; a light detection section for detecting the return lights received by the light receiving optical system; a cap which is freely removably attached to the distal portion of the insertion section; an illumination light guiding optical system for guiding light from the light source into the light transmission section; a guided light filter section provided inside the illumination light guiding optical system for shielding light in a predetermined wavelength band for the light from the light source; and an illumination light filter section provided in the cap for shielding light in a predetermined wavelength band for light which is transmitted from the light source and are emitted to the subject.

Addition 4

The optical imaging device according to one of Additions 1 to 3, wherein the light transmission section further comprises a light guiding section provided inside the insertion section for guiding the light from the light source into the distal portion of the insertion section, and an illumination optical system installed at the distal portion of the insertion section for emitting light guided by the light guiding section from the distal portion of the insertion section.

Addition 5

The optical imaging device according to Addition 1, further comprising an illumination light guiding optical system for guiding the light from the light source into the light transmission section for shielding light in a predetermined wavelength band inside the illumination light guiding optical system.

Addition 6

The optical imaging system according to Additions 1 or 2, wherein the illumination light filter section is an optical thin film formed on at least one element face out of the elements constituting the light transmission section.

Addition 7

The optical imaging device according to Addition 1, wherein a light receiving filter section for shielding light in a predetermined wavelength band in the return lights from the subject is provided inside or in a light receiving end face of the light receiving optical system.

Addition 8

The optical imaging device according to Addition 2, wherein the illumination light filter section includes a visible light band in the transmission band.

Addition 9

The optical imaging device according to Addition 4, wherein the illumination light filter section constitutes at least a part of the illumination optical system and is a light absorbing element made up of a light absorbing material.

Added Additions

1. In Addition 1 or 4, the illumination light filter section transmits light in a fluorescence wavelength band for generating fluorescence from a substance inside the subject or a fluorescent substance injected into the subject.
2. In Addition 1 or 4, the illumination light filter section transmits light in a near infrared band.
3. In Addition 1 or 4, the illumination light filter section shields light in at least a part of the wavelength band of a visible light band.
4. In Addition 1 or 4, the image generation section further comprises a reflected light image generation section for generating a reflected light image based on signal from the reflected light image capturing section, and a fluorescent image generation section for generating a fluorescent image based on signal from the fluorescent image capturing section.
5. In Addition 2, wherein the transmission band of the illumination light filter section includes at least a visible light band.
6. In Addition 2, the illumination light filter section transmits light in a near infrared band.
7. In Addition 2, the illumination light filter section shields light in at least a part of the wavelength band of a visible light band.
8. In Addition 3, the cap has a light receiving filter section for shielding light in a predetermined wavelength band out of the return lights from the subject received by the light receiving optical system.
9. In one of Additions 1 to 4, the image capturing section further comprises a reflected light image capturing section for detecting reflected light in the return lights from the subject and a fluorescent image capturing section for detecting fluorescence from the subject.
10. In one of Additions 1 to 4, the insertion section is an optical probe that can be inserted into an endoscope or a channel for inserting a treatment tool of an endoscope.
11. In one of Additions 1 to 4, the illumination light filter section has a shielding filter to shield light from an illumination light path for shielding the wavelength bands of fluorescence or Raman scattering light which is generated by the light from the light source via the light guiding section in the illumination light path, from the light source to the end face of the illumination optical system.
12. In Addition 6, the wavelength band shielded by the guided light filter section is approximately the same as the wavelength band shielded by the illumination light filter section.
13. In Addition 6, the maximum OD value in the wavelength band shielded by the illumination light filter section is lower than the maximum OD value in the wavelength band shielded by the guided light filter section.
14. In Addition 6, the maximum OD value in the wavelength band shielded by the illumination light filter section is 4 or less.
15. In Addition 6, the wavelength band shielded by the illumination light filter section is narrower than the wavelength band shielded by the guided light filter section.
16. In Addition 6, the guided light filter section further comprises an excitation light transmission filter for transmitting excitation light for generating fluorescence from the subject, and a visible light transmission filter for transmitting light in at least a part of the wavelength band of a visible light band.
17. In Addition 6, the guided light filter section at least has an absorption filter for absorbing light in a predetermined wavelength band.
18. In Addition 7, the light guide section is an optical fiber bundle.
19. In Addition 7, the optical thin film includes a dielectric thin film layer formed by a plurality of layers.
20. In Addition 7, the optical thin film includes a metal thin film for absorbing light in a predetermined wavelength band.
21. In Addition 8, the transmission wavelength band of the light receiving filter section is longer than the transmission wavelength band of the illumination light filter section.
22. In Addition 8, the illumination light filter section and the light receiving filter section are installed on a same element.
23. In Addition 8, the light receiving filters section transmits only fluorescence generated by the subject.
24. In Addition 8, the light receiving filter section transmits light in a near infrared band.
25. In Addition 9, the illumination light filter section transmits light in a near infrared band.
26. In the added Addition 4, the image generation section has an image synthesizing section for composing the reflected light image and fluorescent image.
27. In the added Addition 4, the image generation section further comprises an illumination light filter information recording section for recording information on the wavelength characteristic shielded by the illumination light filter, and an image correction section for correcting a reflected light image generated by the reflected light image generation section based on information from the illumination light filter information recording section.
28. In the added Addition 6, the illumination light filter section transmits light in at least a part of a wavelength band out of 650 to 900 nm.
29. In the added Addition 10, the illumination light filter section is made up of a short wavelength transmission filter for transmitting light with a wavelength shorter than the fluorescence or Raman scattering light generated in the illumination light path.
30. In the added Addition 24, the light receiving filter section transmits light in at least a part of the wavelength band out of 700 to 900 nm.
31. In the added Addition 25, the illumination light filter section transmits light in at least a part of the wavelength band out of 650 to 900 nm.

32. In the added Addition 25, the illumination light filter section transmits light in at least a part of the wavelength band of a visible light band.

Having described the preferred embodiments of the invention referring to the accompanying drawings, it should be understood that the present invention is not limited to those precise embodiments, and various changes and modifications thereof could be made by one skilled in the art without departing from the spirit or scope of the invention as defined in the appended Claims.

What is claimed is:

1. An optical imaging device comprising:
    a light source in a light source device for emitting light including excitation light and light in at least a part of the visible light band;
    an insertion section that can be inserted into a body cavity;
    an excitation light filter in the light source device having a passband which is a band of the excitation light that is irradiated to a subject in the light from the light source;
    a light transmission section, which is provided at the insertion section and guides light that has passed the excitation light filter to a subject in the body cavity;
    a light receiving optical system, which is provided at a distal portion of the insertion section and receives return light from the subject, of the light guided to the subject by the light transmission section;
    a fluorescent image capturing section for acquiring a fluorescent image related to fluorescence in the return light received by the light receiving optical system; and
    an illumination light filter section including an optical thin film formed on a surface of at least one element of elements constituting the light transmission section for decreasing at least light in a band overlapping with the band of light for which the image is captured by the fluorescent image capturing section, from fluorescent light or Raman scattering light generated in a light path of the light transmission section by light transmitted by the light transmission section and guided to the subject, wherein a maximum optical density value of the illumination light filter section in a wavelength band blocked thereby is lower than a maximum optical density value of the excitation light filter in a wavelength band blocked thereby.

2. The optical imaging device according to claim 1, wherein the illumination light filter section is configured so as to include a visible light band as the transmission band.

3. The optical imaging device according to claim 1, wherein
    the light transmission section comprises:
        a light guide section, provided at the insertion section, for guiding light from the light source to the distal portion of the insertion section; and
        an illumination optical system, provided at the distal portion of the insertion section, for emitting the light guided by the light guide section from the distal portion of the insertion section, and
    the illumination light filter section is provided in the illustration illumination optical system.

4. The optical imaging device according to claim 3, wherein the illumination light filter section includes a light absorption element comprising a light absorption material.

5. The optical imaging device according to claim 1, wherein the light receiving optical system is configured to have a light receiving filter section for transmitting only light in bands required for acquiring a fluorescent image on an optical path for guiding received return light to the fluorescent image capturing section.

6. The optical imaging device according to claim 1, further comprising:
    a reflected light image capturing section for acquiring a reflected light image related to light in the visible light band in the return light received by the light receiving optical system.

7. The optical imaging device according to claim 6 wherein the acquisition of a reflected light image by the reflected light image capturing section and acquisition of a fluorescent image by the fluorescent image capturing section are performed simultaneously.

8. The optical imaging device according to claim 6 further comprising:
    an image synthesizing section for generating a synthesized image for simultaneously displaying the reflected light image and fluorescent image; and
    an image display section for displaying the synthesized image generated by the image synthesizing section.

9. The optical imaging device according to claim 1, further comprising:
    a freely removable cap at the distal portion of the insertion section, wherein the illumination light filter section is provided at the cap, and is set at the light emitting end side of the light transmission section by attaching the cap to the distal portion of the insertion section.

* * * * *